(12) United States Patent
Zhang et al.

(10) Patent No.: US 10,874,677 B2
(45) Date of Patent: Dec. 29, 2020

(54) SUBCUTANEOUSLY ADMINISTERED ANTI-IL-6 RECEPTOR ANTIBODY

(71) Applicants: Hoffmann-La Roche Inc., Little Falls, NJ (US); CHUGAI SEIYAKU KABUSHIKI KAISHA, Tokyo (JP)

(72) Inventors: Xiaoping Zhang, Wayne, NJ (US); Kimio Terao, Funabashi (JP)

(73) Assignees: Hoffmann-La Roche Inc., Litte Falls, NJ (US); CHUGAI SEIYAKU KABUSHIKI KAISHA, Tokyo (JP)

( * ) Notice: Subject to any disclaimer, the term of this patent is extended or adjusted under 35 U.S.C. 154(b) by 116 days.

(21) Appl. No.: 16/254,105

(22) Filed: Jan. 22, 2019

(65) Prior Publication Data

US 2019/0247403 A1 Aug. 15, 2019

Related U.S. Application Data

(62) Division of application No. 15/668,445, filed on Aug. 3, 2017, now Pat. No. 10,231,981, which is a division of application No. 14/062,026, filed on Oct. 24, 2013, now Pat. No. 9,750,752, which is a division of application No. 13/290,366, filed on Nov. 7, 2011, now Pat. No. 8,580,264.

(60) Provisional application No. 61/542,615, filed on Oct. 3, 2011, provisional application No. 61/411,015, filed on Nov. 8, 2010.

(51) Int. Cl.

| A61K 39/395 | (2006.01) |
|---|---|
| A61K 31/573 | (2006.01) |
| A61K 38/47 | (2006.01) |
| C07K 16/28 | (2006.01) |
| A61K 9/00 | (2006.01) |
| A61K 39/00 | (2006.01) |

(52) U.S. Cl.
CPC .......... *A61K 31/573* (2013.01); *A61K 9/0019* (2013.01); *A61K 38/47* (2013.01); *A61K 39/3955* (2013.01); *A61K 39/39533* (2013.01); *C07K 16/2866* (2013.01); *C12Y 302/01035* (2013.01); *A61K 2039/505* (2013.01); *A61K 2039/54* (2013.01); *A61K 2039/545* (2013.01); *A61K 2300/00* (2013.01); *C07K 2317/24* (2013.01); *C07K 2317/76* (2013.01); *C07K 2317/94* (2013.01)

(58) Field of Classification Search
CPC .................................................. A61K 39/395
See application file for complete search history.

(56) References Cited

U.S. PATENT DOCUMENTS

| 4,672,057 | A | 6/1987 | Bargiotti et al. |
|---|---|---|---|
| 4,824,674 | A | 4/1989 | Becker et al. |
| 5,126,250 | A | 6/1992 | McDonough et al. |
| 5,171,840 | A | 12/1992 | Kishimoto |
| 5,480,796 | A | 1/1996 | Kishimoto |
| 5,670,373 | A | 9/1997 | Kishimoto et al. |
| 5,795,965 | A | 8/1998 | Tsuchiya et al. |
| 5,817,790 | A | 10/1998 | Tsuchiya et al. |
| 5,851,793 | A | 12/1998 | Kishimoto |
| 5,888,510 | A | 3/1999 | Kishimoto et al. |
| 5,990,282 | A | 11/1999 | Kishimoto |
| 5,994,511 | A | 11/1999 | Lowman et al. |
| 6,086,874 | A | 7/2000 | Yoshida et al. |
| 6,242,200 | B1 * | 6/2001 | Wilkison ........... G01N 33/5008 435/7.1 |
| 6,261,560 | B1 | 7/2001 | Tsujinaka et al. |
| 6,365,154 | B1 | 4/2002 | Holmes et al. |
| 6,406,909 | B1 | 6/2002 | Shibuya et al. |
| 6,410,691 | B1 | 6/2002 | Kishimoto |
| 6,428,979 | B1 | 8/2002 | Kishimoto |
| 6,537,782 | B1 | 3/2003 | Shibuya et al. |
| 6,692,742 | B1 | 2/2004 | Nakamura et al. |
| 6,723,319 | B1 | 4/2004 | Ito et al. |
| 6,875,432 | B2 | 4/2005 | Liu et al. |
| 6,962,812 | B2 | 11/2005 | Shibuya et al. |
| 7,320,792 | B2 | 1/2008 | Ito et al. |
| 7,332,289 | B2 | 2/2008 | Takeda et al. |
| 7,479,543 | B2 | 1/2009 | Tsuchiya et al. |
| 7,498,031 | B2 | 3/2009 | Fujioka et al. |
| 7,521,052 | B2 | 4/2009 | Okuda et al. |
| 7,531,358 | B2 | 5/2009 | Kakuta et al. |
| 7,566,453 | B2 | 7/2009 | Nakamura et al. |
| 7,666,413 | B2 | 2/2010 | Liu et al. |
| 7,767,429 | B2 | 8/2010 | Bookbinder et al. |
| 7,771,723 | B2 | 8/2010 | Nakamura et al. |
| 7,824,674 | B2 | 11/2010 | Ito et al. |

(Continued)

FOREIGN PATENT DOCUMENTS

| EP | 0783893 | 7/1997 |
|---|---|---|
| EP | 0983767 | 3/2000 |

(Continued)

OTHER PUBLICATIONS

Adamczyk et al., "Complete sequencing of anti-vancomycin fab fragment by liquid chromatography-electrospray ion trap mass spectrometry with a combination of database searching and manual interpretation of the MS/MS spectra" Journal of Immunological Methods 2690:235-249 ( 2002).

(Continued)

*Primary Examiner* — Prema M Mertz
(74) *Attorney, Agent, or Firm* — Wendy M. Lee

(57) ABSTRACT

The present application discloses methods for treating an IL-6-mediated disorder such as rheumatoid arthritis (RA), juvenile idiopathic arthritis (JIA), systemic JIA (sJIA), polyarticular course JIA (pcJIA), systemic sclerosis, or giant cell arteritis (GCA), with subcutaneously administered antibody that binds interleukin-6 receptor (anti-IL-6R antibody). In particular, it relates to identification of a fixed dose of anti-IL-6R antibody, e.g. tocilizumab, which is safe and effective for subcutaneous administration in patients with IL-6-mediated disorders. In addition, formulations and devices useful for subcutaneous administration of an anti-IL-6R antibody are disclosed.

8 Claims, 22 Drawing Sheets

Specification includes a Sequence Listing.

(56) References Cited

U.S. PATENT DOCUMENTS

| | | |
|---|---|---|
| 7,927,815 B2 | 4/2011 | Takeda et al. |
| 7,955,598 B2 | 6/2011 | Yoshizaki et al. |
| 8,017,121 B2 | 9/2011 | Kishimoto et al. |
| 8,142,776 B2 | 3/2012 | Liu et al. |
| 8,173,126 B2 | 5/2012 | Yoshizaki et al. |
| 8,227,195 B2 | 7/2012 | Stubenrauch et al. |
| 8,398,980 B2 | 3/2013 | Kano et al. |
| 8,420,789 B2 | 4/2013 | Takeda et al. |
| 8,440,196 B1 | 5/2013 | Funakoshi et al. |
| 8,470,316 B2 | 6/2013 | Yasunami |
| 8,529,895 B2 | 9/2013 | Mihara et al. |
| 8,530,176 B2 | 9/2013 | Stubenrauch et al. |
| 8,562,990 B2 | 10/2013 | Ito et al. |
| 8,562,991 B2 | 10/2013 | Igawa et al. |
| 8,568,720 B2 | 10/2013 | Morichika et al. |
| 8,580,264 B2 | 12/2013 | Zhang et al. |
| 8,597,644 B2 | 12/2013 | Ito et al. |
| 8,617,550 B2 | 12/2013 | NIshimoto et al. |
| 8,623,355 B2 | 1/2014 | Okada et al. |
| 8,632,778 B2 | 1/2014 | Kakuta et al. |
| 8,703,126 B2 | 4/2014 | Liu et al. |
| 8,709,409 B2 | 4/2014 | Okuda et al. |
| 8,734,800 B2 | 5/2014 | Kano et al. |
| 8,771,686 B2 | 8/2014 | Ishida |
| 8,802,092 B2 | 8/2014 | Nishimoto et al. |
| 8,809,509 B2 | 8/2014 | Takeda et al. |
| 8,840,884 B2 | 9/2014 | Kakuta et al. |
| 8,921,527 B2 | 12/2014 | Mizushima et al. |
| 8,945,558 B2 | 2/2015 | Kobara |
| 8,961,964 B2 | 2/2015 | Liu et al. |
| 9,017,677 B2 | 4/2015 | Mihara |
| 9,051,384 B2 | 6/2015 | Kakuta et al. |
| 9,084,777 B2 | 7/2015 | Morichika et al. |
| 9,255,145 B2 | 2/2016 | Yoshizaki et al. |
| 9,260,516 B2 | 2/2016 | Nishimoto et al. |
| 9,422,329 B2 | 8/2016 | Falkenstein et al. |
| 9,539,263 B2 | 1/2017 | Zhang et al. |
| 9,539,322 B2 | 1/2017 | Nishimura |
| 9,630,988 B2 | 4/2017 | Lau et al. |
| 9,714,410 B2 | 7/2017 | Goto et al. |
| 9,725,514 B2 | 8/2017 | Takahashi et al. |
| 9,750,752 B2 | 9/2017 | Zhang et al. |
| 9,902,777 B2 | 2/2018 | Kano et al. |
| 10,022,319 B2 | 7/2018 | Igawa et al. |
| 10,034,940 B2 | 7/2018 | Liu et al. |
| 10,168,326 B2 | 1/2019 | Stubenrauch et al. |
| 10,231,981 B2 | 3/2019 | Zhang et al. |
| 10,316,096 B2 | 6/2019 | Morichika et al. |
| 10,377,794 B2 | 8/2019 | Falkenstein et al. |
| 10,501,769 B2 | 12/2019 | Franze et al. |
| 10,590,164 B2 | 3/2020 | Lau et al. |
| 10,654,888 B2 | 5/2020 | Takeda et al. |
| 10,662,245 B2 | 5/2020 | Igawa et al. |
| 10,717,781 B2 | 7/2020 | Mitsunaga et al. |
| 10,744,201 B2 | 8/2020 | Okuda et al. |
| 10,761,091 B2 | 9/2020 | Stubenrauch et al. |
| 2001/0001663 A1 | 5/2001 | Kishimoto et al. |
| 2002/0045571 A1 | 4/2002 | Liu et al. |
| 2002/0131967 A1 | 9/2002 | Nakamura et al. |
| 2002/0187150 A1 | 12/2002 | Mihara et al. |
| 2003/0096372 A1 | 5/2003 | Shibuya et al. |
| 2003/0190316 A1 | 10/2003 | Kakuta et al. |
| 2004/0028681 A1 | 2/2004 | Ito et al. |
| 2004/0071706 A1 | 4/2004 | Ito et al. |
| 2004/0115197 A1 | 6/2004 | Yoshizaki et al. |
| 2004/0138424 A1 | 7/2004 | Takeda et al. |
| 2004/0197324 A1 | 10/2004 | Liu et al. |
| 2004/0247621 A1 | 12/2004 | Nakamura et al. |
| 2005/0118163 A1 | 6/2005 | Mizushima et al. |
| 2005/0142635 A1 | 6/2005 | Tsuchiya et al. |
| 2005/0158303 A1 | 7/2005 | Liu et al. |
| 2005/0175603 A1 | 8/2005 | Liu et al. |
| 2005/0214278 A1 | 9/2005 | Kakuta et al. |
| 2005/0238644 A1 | 10/2005 | Mihara et al. |
| 2006/0127975 A1 | 6/2006 | Link et al. |
| 2006/0134113 A1 | 6/2006 | Mihara |
| 2006/0142549 A1 | 6/2006 | Takeda et al. |
| 2006/0165696 A1 | 7/2006 | Okano et al. |
| 2006/0251653 A1 | 11/2006 | Okuda et al. |
| 2006/0292147 A1 | 12/2006 | Yoshizaki et al. |
| 2007/0036785 A1 | 2/2007 | Kishimoto et al. |
| 2007/0053900 A1 | 3/2007 | Liu et al. |
| 2007/0086995 A1 | 4/2007 | Liu et al. |
| 2007/0098714 A1 | 5/2007 | Nishimoto et al. |
| 2007/0116700 A1 | 5/2007 | Liu et al. |
| 2007/0134242 A1 | 6/2007 | Nishimoto et al. |
| 2007/0148169 A1 | 6/2007 | Yoshizaki et al. |
| 2007/0243189 A1 | 10/2007 | Yoshizaki et al. |
| 2008/0124325 A1 | 5/2008 | Ito et al. |
| 2008/0124761 A1 | 5/2008 | Goto et al. |
| 2008/0255342 A1 | 10/2008 | Takeda et al. |
| 2008/0274106 A1 | 11/2008 | Nishimoto et al. |
| 2008/0299668 A1 | 12/2008 | Xue et al. |
| 2008/0306247 A1 | 12/2008 | Mizushima et al. |
| 2009/0022719 A1 | 1/2009 | Mihara et al. |
| 2009/0061466 A1 | 3/2009 | Hoesel et al. |
| 2009/0131639 A1 | 5/2009 | Kakuta et al. |
| 2009/0181029 A1 | 7/2009 | Okuda et al. |
| 2009/0220499 A1 | 9/2009 | Yasunami |
| 2009/0220500 A1 | 9/2009 | Kobara |
| 2009/0263384 A1 | 10/2009 | Okada et al. |
| 2009/0269335 A1 | 10/2009 | Nakashima et al. |
| 2009/0280129 A1 | 11/2009 | Liu et al. |
| 2009/0291076 A1 | 11/2009 | Morichika et al. |
| 2010/0008907 A1 | 1/2010 | Nishimoto et al. |
| 2010/0034811 A1 | 2/2010 | Ishida |
| 2010/0061986 A1 | 3/2010 | Takahashi et al. |
| 2010/0129355 A1 | 5/2010 | Ohguro et al. |
| 2010/0158898 A1 | 6/2010 | Liu et al. |
| 2010/0247523 A1 | 9/2010 | Kano et al. |
| 2010/0255007 A1 | 10/2010 | Mihara et al. |
| 2010/0285011 A1 | 11/2010 | Morichika et al. |
| 2010/0304400 A1 | 12/2010 | Stubenrauch et al. |
| 2011/0098450 A1 | 4/2011 | Igawa et al. |
| 2011/0117087 A1 | 5/2011 | Franze et al. |
| 2011/0150869 A1 | 6/2011 | Mitsunaga et al. |
| 2011/0206664 A1 | 8/2011 | Yoshizaki et al. |
| 2011/0245473 A1 | 10/2011 | Igawa et al. |
| 2011/0262462 A1 | 10/2011 | Platt et al. |
| 2011/0268734 A1 | 11/2011 | Ito et al. |
| 2012/0009177 A1 | 1/2012 | Platt et al. |
| 2012/0064086 A1 | 3/2012 | Liu et al. |
| 2012/0076783 A1 | 3/2012 | Liu et al. |
| 2012/0183539 A1 | 7/2012 | Maeda |
| 2012/0219974 A1 | 8/2012 | Stubenrauch et al. |
| 2012/0253016 A1 | 10/2012 | Igawa et al. |
| 2012/0301460 A1 | 11/2012 | Bao et al. |
| 2013/0149302 A1 | 6/2013 | Mitsunaga et al. |
| 2013/0202588 A1 | 8/2013 | Nishimura |
| 2013/0209456 A1 | 8/2013 | Kano et al. |
| 2013/0225796 A1 | 8/2013 | Takeda et al. |
| 2013/0317203 A1 | 11/2013 | Igawa et al. |
| 2014/0005367 A1 | 1/2014 | Morichika et al. |
| 2014/0017236 A1 | 1/2014 | Okuda et al. |
| 2014/0056883 A1 | 2/2014 | Zhang et al. |
| 2014/0056884 A1 | 2/2014 | Zhang et al. |
| 2014/0056885 A1 | 2/2014 | Zhang et al. |
| 2014/0079695 A1 | 3/2014 | Nishimoto et al. |
| 2014/0323695 A1 | 10/2014 | Takeda et al. |
| 2014/0329277 A1 | 11/2014 | Link et al. |
| 2014/0377254 A1 | 12/2014 | Kano et al. |
| 2015/0010554 A1 | 1/2015 | Okuda et al. |
| 2015/0037319 A1 | 2/2015 | Lau et al. |
| 2015/0044198 A1 | 2/2015 | Liu et al. |
| 2015/0166666 A1 | 6/2015 | Igawa et al. |
| 2015/0191540 A1 | 7/2015 | Mihara |
| 2015/0225485 A1 | 8/2015 | Liu et al. |
| 2015/0253338 A1 | 9/2015 | Hoesel et al. |
| 2015/0284466 A1 | 10/2015 | Morichika et al. |
| 2016/0022812 A1 | 1/2016 | Mitsunaga et al. |
| 2016/0186228 A1 | 6/2016 | Franze et al. |
| 2016/0194401 A1 | 7/2016 | Yoshizaki et al. |
| 2016/0313322 A1 | 10/2016 | Stubenrauch et al. |
| 2016/0326255 A1 | 11/2016 | Ohguro et al. |

(56) References Cited

U.S. PATENT DOCUMENTS

| | | |
|---|---|---|
| 2016/0367675 A1 | 12/2016 | Liu et al. |
| 2017/0022278 A1 | 1/2017 | Mihara et al. |
| 2017/0049888 A1 | 2/2017 | Liu et al. |
| 2017/0204135 A1 | 7/2017 | Lau et al. |
| 2017/0360807 A1 | 12/2017 | Zhang et al. |
| 2018/0051090 A1 | 2/2018 | Yamamoto et al. |
| 2018/0148509 A1 | 5/2018 | Kakehi et al. |
| 2018/0222986 A1 | 8/2018 | Maeda |
| 2018/0222988 A1 | 8/2018 | Yoshizaki et al. |
| 2018/0230222 A1 | 8/2018 | Kano et al. |
| 2018/0236068 A1 | 8/2018 | Mitsunaga et al. |
| 2019/0002572 A1 | 1/2019 | Mihara et al. |
| 2019/0054167 A1 | 2/2019 | Okuda et al. |
| 2019/0085085 A1 | 3/2019 | Igawa et al. |
| 2019/0094216 A1 | 3/2019 | Stubenrauch et al. |
| 2019/0170765 A1 | 6/2019 | Hoesel et al. |
| 2019/0358323 A1 | 11/2019 | Liu et al. |
| 2020/0079857 A1 | 3/2020 | Morichika et al. |
| 2020/0080125 A1 | 3/2020 | Franze et al. |
| 2020/0148775 A1 | 5/2020 | Kano et al. |
| 2020/0165297 A1 | 5/2020 | Falkenstein et al. |
| 2020/0172569 A1 | 6/2020 | Lau et al. |
| 2020/0181669 A1 | 6/2020 | Franze et al. |
| 2020/0231688 A1 | 7/2020 | Igawa et al. |

FOREIGN PATENT DOCUMENTS

| | | |
|---|---|---|
| JP | 7188056 A | 7/1995 |
| JP | 03630453 B2 | 3/2005 |
| JP | 03822137 B2 | 9/2006 |
| JP | 2009092508 A | 4/2009 |
| WO | 9618648 | 6/1996 |
| WO | 9813383 | 4/1998 |
| WO | 9948523 | 9/1999 |
| WO | 2000/10607 A1 | 3/2000 |
| WO | 2002/013859 A1 | 2/2002 |
| WO | 2008/016134 A1 | 2/2008 |
| WO | 2008/078715 A1 | 7/2008 |
| WO | 2010/065079 | 6/2010 |
| WO | 2010/106812 A1 | 9/2010 |
| WO | 2011/013786 A1 | 2/2011 |
| WO | 2011/149046 A1 | 12/2011 |
| WO | 2011/149051 A1 | 12/2011 |
| WO | 2012/064627 A2 | 5/2012 |

OTHER PUBLICATIONS

Arkachaisri et al., "Use of Biologies in the Treatment of Childhood Rheumatic Diseases" Current Rheumatology Reports 2:330-336 ( 2000).

Atamas, "Complex cytokine regulation of tissue fibrosis" Life Sci. 72(6):631-43 ( 2002).

Bathon et al., "A comparison of etanerecpt and methotrexate in patients with early rheumatoid arthritis" New Engl J Med 343(22): 1586-93 (Nov. 2000).

Bellomo et al., "The Cytokine Network in the Critically Ill" Anaesthesia and Intensive Care 20(3):288-302 (Aug. 1992).

Beyer et al., "Anti-interleukin 6 receptor therapy as rescue treatment for giant cell arteritis" Ann Rheum Dis. (doi:10.1136/ard.2010. 149351) 70(10):1874-5 ( 2011).

Bhat et al., "Giant cell arteritis. Midlife and Beyond" Rheumatology:071-079 (Feb. 2010).

Borchers et al., "Giant cell arteritis: reveiw of classification, pathophysiology, geoepidemiolody and treatment" Autoimmunity Reviews 11:A544-555 ( 2012).

Bosello et al., "B cell depletion in diffuse progressive systemic sclerosis: safety, skin score modification and IL-6 modulation in an up to thirty-six months follow-up open-label trial" Arthritis Res Ther. 12(2 Suppl R54):1-10 ( 2010).

Brewer et al., "Penicillamine and Hydroxychloroquine in the treatment of severe juvenile rheumatoid arthritis" The new England Journal of Medicine 314(20):1270-1276 (May 15, 1986).

Brooks, "Clinical management of rheumatoid arthritis" Lancet 341:286-90 ( 1993).

Carroll et al., "Antagonism of the IL-6 cytokine subfamily—a potential strategy for more effective therapy in more effective therapy in rheumatoid arthritis" Inflammation Research 47:1-7 ( 1998).

Christidis et al., "Successful use of tocilizumab in polymyalgic onset biopsy positive GCA with large vessel involvement" BMJ Case Reports (doi:10.1136/bcr.04.2011.4135),:1-4 ( 2011).

Chugai Pharmaceutical Co., Ltd., "An open label, intra-patients dose ascending, repeated administration study of subcutaneous injection of MRA in patients with rheumatoid arthritis" JAPIC Clinical Trials Information (JapicCTI-090713; Application date: Mar. 9, 2009; Revised dates Jun. 15, 2009 and Sep. 17, 2010; Printed May 14, 2014),:1-2 http://www.clinicaltrials.jp/user/showCteDetailE.jsp?japicId=JapicCTI-090713.

Chugai Pharmaceutical Co., Ltd., "Development Pipeline" (as of Feb. 3, 2010),:1-7.

Chugai Pharmaceutical Co., Ltd.,: 'Anti-Human IL-6 Receptor Monoclonal Antibody 'ACTEMRA®' Subcutaneous Injection Demonstrates Efficacy in Rheumatoid Arthritis in Phase III Clinical Study.' Retrieved from the Internet on Jan. 26, 2012: http://www.roche.com/investors/ir_update/inv-update-2011-07-19b.htm ( Jul. 19, 2011).

Clements et al., "Skin Thickness Score as a Predictor and Correlate of Outcome in Systemic Sclerosis" Arthritis Rheum. 43(11):2445-54 ( 2000).

Daoussis et al., "Experience with rituximab in scleroderma: results from a 1-year, proof-of-principle study" Rheumatology 49(2):271-80 ( 2010).

DeBenedetti et al., "Interleukin 6 causes growth impairment in transgenic mice through a decrease in insulin-like growth factor-I" J. Clin. Invest. 99(4):643-650 (Feb. 1997).

DeBenedetti et al., "Is systemic juvenile rheumatoid arthritis an interleukin 6 mediated disease?" The Journal of Rheumatology 25(2):203-207 ( 1998).

DeBenedetti et al., "Juvenile Idiopathic Arthritis Will Etanercept be an Improvement over Current Therapies?" BioDrugs 14(2):93-98 ( 2000).

Declaration 132 of Lehman, pp. 1-13 ( Sep. 4, 2015).

Distler et al., "Tocilizumab for systemic sclerosis: implications for future trials" The Lancet:1-2 (May 5, 2016) http://dx.doi.org/10.1016/S0140-6736(16)00622-X.

Duncan and Berman, "Stimulation of collagen and glycosaminoglycan production in cultured human adult dermal fibroblasts by recombinant human interleukin 6" J Invest Dermatol. 97(4):686-92 ( 1991).

Elhai et al., "Outcomes of patients with systemic sclerosis-associated polyarthritis and myopathy treated with tocilizumab or abatacept: a EUSTAR observational study" Ann Rheum Dis 72:1217-1220 ( 2013).

Elliott et al., "Suppression of fever and the acute-phase response in a patient with juvenile chronic arthritis treated with monoclonal antibody to tumour necrosis factor-a (cA2)" British Journal of Rheumatology 36:589-593 ( 1997).

Elliott et al., "Treatment of systemic juvenile chronic arthritis (JCA) with monoclonal anti-TNF-alpha: temporary control systemic but not articular features of disease" Arthritis & Rheumatism 37(9):S276 ( 1994).

EMA, Science Medicine Health, Type II variation EMEA/H/C/955/II/15 (2011).

Emery et al., "IL-6 receptor inhibition with tocilizumab improves treatment outcomes in patients with rheumatoid arthritis refractory to anti-tumour necrosis factor biologicals: results from a 24-week multicentre randomised placebo-controlled trial" Ann Rheum Dis. 67(11):1516-23 ( 2008).

"Fast Track, Breakthrough Therapy, Accelerated Approval, and Priority Review https://www.fda.gov/forpatients/approvals/fast/ucm405405.htm" ([retrieved Mar. 30, 2017]).

"Fast Track, Breakthrough Therapy, Accelerated Approval, and Priority Review https://www.fda.gov/forpatients/approvals/fast/ucm405397.htm" ([retrieved on Mar. 30, 2017]).

(56) References Cited

OTHER PUBLICATIONS

"FDA Grants Priority Review For Genentech's Actemra® (Tocilizumab) Supplemental Biologics License Application For Giant Cell Arteritis, a Form of Vasculitis https://www.gene.com/media/press-releases/14653/2017-01-23/fda-grants-priority-review-for-genentech" ([retrieved on Mar. 30, 2017]),:1-5 (Jan. 23, 2017).

FDA News Release ( Apr. 15, 2011).

Fishman et al., "The effect of novel polymorphisms in the interleukin-6 (IL-6) gene on IL-6 transcription and plasma IL-6 levels, and an association with systemic-onset juveline chronic arthritis" J. Clin. Invest. 102(7): 1369-1376 (Oct. 1998).

Fossiez et al., "T cell interleukin-17 induces stromal cells to produce proinflammatory and hematopoietic cytokines" J Exp Med. 183(6):2593-603 ( 1996).

Furst et al., "The Modified Rodnan Skin Score is an Accurate Reflection of Skin Biopsy Thickness in Systemic Sclerosis" J. Rheumatol. 25(1):84-88 ( 1998).

Gallagher et al., "Juvenile rhematoid arthritis" Current Opinion in Rheumatology 11:372-376 ( 1999).

Garcia-Martinez et al., "Clinical relevance of persistently elevated circulating cytokines (tumor necrosis factor alpha and interleukin-6) in the long-term followup of patients with giant cell arteritis" Arthritis Care Res (Hoboken) 62(6):835-841 (Jun. 2010).

Georgy et al., "A clinical study to assess the pharmacokinetics and pharmacodynamics of Tocilizumab after a single dose administration by subcutaneous and intravenous routes to healthy subjects" Journal of Clinical Pharmacology (39th Annual Meeting of the American College of Clinical Pharmacology; Baltimore, Maryland, USA; Sep. 12-14, 2010), 50(9):1084 (Sep. 2010).

Georgy et al., "A clinical study to assess the pharmacokinetics and pharmacodynamics of Tocilizumab after a single dose administration by subcutaneous and intravenous routes to healthy subjects" Clinical Pharmacology & Therapeutics (Abstract PII-65), 87( Suppl 1): S60 (Feb. 2010).

Georgy et al., "Poster 38 Pharmacokinetics and Pharmacodynamics of Tocilizumab After Single Subcutaneous and Intravenous Doses in Healthy Subjects—Presented at the 39th American College of Clinical Pharmacology (ACCP) Annual Meeting, Sep. 12-14, 2010, Baltimore, Maryland" pp. 1-6 (2010).

Giannini et al., "Effects of long-term etanercept treatment on growth in children with selected categories of juvenile idiopathic arthritis" Arthritis & Rheumatism 62(11):3259-3264 (Nov. 2010).

Heinhuis et al., "Tumour necrosis factor alpha-driven IL-32 expression in rheumatoid arthritis synovial tissue amplifies an inflammatory cascade" Ann Rheum Dis. 70(4):660-7 ( 2011).

Hirano et al., "Excessive production of interleukin 6/B cell stimulatory factor-2 in rheumatoid arthritis" Eur J Immunol. 18(11):1797-801 ( 1988).

Hirano, "The biology of interleukin-6" Chem Immunol. 51:153-80 ( 1992).

Hoffmann-La Roche, "A Study of Administration of RoActemra/Actemra (Tocilizumab) by Auto-injector Vs. Pre-filled Syringe in Healthy Volunteers" (ClinicalTrials. gov Identifier: NCT01418989, First received: Aug. 16, 2011; Last updated: Aug. 15, 2012, Retrieved: Feb. 12, 2013),:1-2 http://www.clinicaltrials.gov/ct2/show/NCT01418989.

Hoffmann-La Roche, "A Study of RoActemra/Actemra (Tocilizumab) Given Subcutaneously in Combination With Traditional DMARDs in Patients With Moderate to Severe Active Rheumatoid Arthritis" (ClinicalTrials.gov Identifier: NCT01232569; First received: Nov. 1, 2010; Last updated: Dec. 3, 2012; Retrieved: Feb. 12, 2013),:1-3 http://www.clinicaltrials.gov/ct2/show/NCT01232569.

Hoffmann-La Roche, "A Study of RoAtemra/Actemra (tocilizumab) in Patients with Giant Cell Arteritis" (ClinicalTrials.gov identifier NCT01791153; First received Feb. 12, 2013; Last updated Aug. 17, 2015; Last verified Aug. 2015; Retrieved on Aug. 26, 2015),:1-4 http://www.clinicaltrials.gov/ct2/show/NCT01791153.

Hoffmann-La Roche, "A Study of RoActemra/Actemra (Tocilizumab) Versus Placebo in Patients with Systemic Sclerosis" (ClinicalTrials. gov identifier: NCT01532869; First received Feb. 10, 2012; Last updated Oct. 8, 2015; Last verified Oct. 2015; Retrieved Nov. 13, 2015),:1-4 http://clinicaltrials.gov/ct2/show/NCT01532869.

Hoffmann-La Roche, "A Study of Subcutaneously Administered RoActemra/Actemra (Tocilizumab) in Patients with Polyarticular-Course Juvenile Idiopathic Arthritis" (ClinicalTrials.gov identifier NCT01904279; First received Jun. 14, 2013; Last updated Nov. 3, 2014; Last verified Nov. 2014; Retrieved Nov. 6, 2014),:1-4 http://clinicaltrials.gov/ct2/show/record/NCT01904279.

Hoffmann-La Roche, "A Study of Subcutaneously Administered RoActemra/Actemra (Tocilizumab) in Patients with Systemic Juvenile Idiopathic Arthritis" (ClinicalTrials.gov identifier NCT01904292; First received Jun. 14, 2013; Last updated Nov. 3, 2014; Last verified Nov. 2014; Retrieved Nov. 6, 2014),:1-3 http://clinicaltrials.gov/ct2/show/record/NCT01904292.

Hoffmann-La Roche, "A Study of Subcutaneously Administered Tocilizumab in Patients With Rheumatoid Arthritis" (ClinicalTrials.gov Identifier:NCT00965653; First received: August 18, 2009; Last updated: Dec. 7, 2011; Retrieved: Feb. 12, 2013),:1-3 http://www.clinicaltrials.gov/ct2/show/NCT00965653.

Hoffmann-La Roche, "A Study of the Efficacy and Safety of Tocilizumab in Participants With Systemic Sclerosis (SSc) [focuSSced]" (ClinicalTrials.gov identifier: NCT02453256; First received May 21, 2015; Last updated Sep. 9, 2015; Last verified Sep. 2015; Retrieved Nov. 13, 2015),:1-3 http://clinicaltrials.gov/ct2/show/NCT02453256.

Hoffmann-La Roche, "A Study to Compare Subcutaneous Versus Intravenous Administration of RoActemra/Actemra (Tocilizumab) in Patients With Moderate to Severe Active Rheumatoid Arthritis" (ClinicalTrials.gov Identifier: NCT01194414; First received: Sep. 1, 2010; Last updated: Jan. 7, 2013; Retrieved: Feb. 12, 2013),:1-4 http://www.clinicaltrials.gov/ct2/show/NCT01194414.

Hotchkiss et al., "Is decreasing inflammation or increasing the host immune response the better approach?" Science 347(6227):1201-1202 (Mar. 13, 2015).

Houssiau et al., "Interleukin-6 in synovial fluid and serum of patients with rheumatoid arthritis and other inflammatory arthritides" Arthritis Rheum. 31(6):784-8 ( 1988).

Imagawa et al., "Safety and efficacy of tocilizumab, an anti-IL-6-receptor monoclonal antibody, in patients with polyarticular-course juvenile idiopathic arthritis" Mod Rheumatol. 22(1): 109-115 (Feb. 2012).

Kadono et al., "Increased production of interleukin 6 and interleukin 8 in scleroderma fibroblasts" J Rheumatol. 25(2):296-301 ( 1998).

Katsicas et al., "Use of infliximab in patients with systemic juvenile idiopathic arthritis refractory to etanercept" Clinical and Experimental Rheumatology 22:545-548 ( 2004).

Kaufman, "Tocilizumab Designated as Breakthrough Therapy for GCA http://www.the-rheumatologist.org/article/tocilizumab-designated-breakthrough-therapy-gca" ([retrieved on Apr. 3, 2017]), (Oct. 26, 2016).

Kavanaugh et al., "Golimumab, a new human tumor necrosis factor alpha antibody, administered every four weeks as a subcutaneous injection in psoriatic arthritis: Twenty-four-week efficacy and safety results of a randomized, placebo-controlled study" Arthritis Rheum. 60(4):976-86 ( 2009).

Keller et al., "Molecular and cellular biology of interleukin-6 and its receptor" Frontiers Biosci 1:d340-57 (Dec. 1, 1996).

Keul et al., "A possible role for soluble IL-6 receptor in the pathogenesis of systemic onset juvenile chronic arthritis" Cytokine 10(9):729-734 (Sep. 1998).

Khanna and Merkel, "Outcome Measures in Systemic Sclerosis: An Update on Instruments and Current Research" Curr. Rheumatol. Rep. 9(2):151-7 ( 2007).

Khanna et al., "Safety and Efficacy of Subcutaneous Tocilizumab in Systemic Sclerosis: Results from the Open-Label Period of the faSScinate Trial" Ann Rheum Dis (Abstract No. FRI0268) 75( SUPPL 2):531 ( 2016).

Khanna et al., "Safety and Efficacy of Subcutaneous Tocilizumab (TCZ) in Adults with Systemic Sclerosis (SSc): Week 48 Data From the faSScinate Trial" Slides (Slides) EULAR 2015, pp. 1-23 ( Jun. 2015).

Khanna et al., "Safety and Efficacy of Subcutaneous Tocilizumab in Systemic Sclerosis: Results from the Open-Label Period of the faSScinate Trial (Slides)" Ann Rheum Dis EULAR Slides ( 2016).

(56) References Cited

OTHER PUBLICATIONS

Khanna et al., "Safety and Efficacy of Subcutaneous Tocilizumab in Adults with Systemic Sclerosis: Week 48 Data from the Fasscinate Trial" Ann Rheum Dis (Abstract No. OP0054), 74( Suppl 2):87 (2015).

Khanna et al., "Safety and efficacy of subcutaneous tocilizumab in adults with systemic sclerosis (faSScinate): a phase 2, randomised, controlled trial" The Lancet:1-12 (May 5, 2016) http://dx.doi.org/10.1016/S0140-6736(16)00232-4.

King et al., "Monoclonal antibody conjugates of doxorubicin prepared with branched peptide linkers: Inhibition of aggregation by methoxytriethyleneglycol chains" Journal of Medical Chemistry 45:4336-4343 ( 2002).

Kishimoto et al., "Interleukin-6: From basic science to medicine-40 years in immunology" Annu. Rev. Immunol. 23:1-21 ( 2005).

Koch et al., "In situ expression of cytokines and cellular adhesion molecules in the skin of patients with systemic sclerosis. Their role in early and late disease" Pathobiology 61:239-46 ( 1993).

Kurasawa et al., "Increased interleukin-17 production in patients with systemic sclerosis" Arthritis Rheum. 43(11):2455-2463 ( 2000).

Lafyatis et al., "B cell depletion with rituximab inpatients with diffuse cutaneous systemic sclerosis" Arthritis Rheum. 60(2):578-83 ( 2009).

Lepore et al., "Study of IL-2, IL-6 TNFa, IFNy and B in the serum and synovial fluid of patients with juvenile chronic arthritis" Clinical and Experimental Rheumatology 12:561-565 ( 1994).

Lovell et al., "Etanercept in children with polyarticular juvenile rheumatoid arthritis" The new England Journal of Medicine 342(11):763-769 ( 2000).

Madhok et al., "The relationship of sulfoxidation status to efficacy and toxicity of penicillamine in the treatment of rheumatoid arthritis" Arthritis Rheum. 33(4):574-7 ( 1990)

Madson et al., "Cytokine levels in serum and synovial fluid of patients with juvenile rheumatoid arthritis" The Journal of Rheumatology 21(12):2359-2363 ( 1994).

Maini et al., "Therapeutic efficacy of multiple intravenous infusions of anti-tumor necrosis factor alpha monoclonal antibody combined with low-dose weekly methotrexate in rheumatoid arthritis" Arthritis Rheum. 41(9):1552-63 ( 1998).

Mangge et al., "Cytokines in juvenile rheumatoid arthritis (JRA)" Cytokine 10(6):471-480 (Jun. 1998).

Mangge et al., "Long-term follow-up of cytokines and soluble cytokine receptors in peripheral blood of patients with juvenile rheumatoid arthritis" Journal of Interferon and Cytokine Research 19:1005-1010 ( 1999).

Metzger et al., "Reduced body fat and increased hepatic lipid synthesis in mice bearing interleukin-6-secreting tumor" Am J Physiol Endocrinol Metab. 281:E957-E965 ( 2001).

Meunier et al., "Abstract [2011] [SAT0424] Outcomes of systemic sclerosis associated polyarthritis patients treated by biotherapies Tocilizumab or Abatacept: a EUSTAR observational study" Ann Rheum Dis 70( Suppl 3):660 ( 2011).

Meunier et al., "Outcomes of Systemic Sclerosis Associated Polyarthritis Patients Treated by Biotherapies Tocilizumab or Abatacept: A EUSTAR Observational Study." Arthritis & Rheumatism (Abstract 1462; 75th Annual Scientific Meeting of the American College of Rheumatology/46th Annual Scientific Meeting; Chicago, IL, USA), 63(10 Suppl 1):S572 (Oct. 2011).

Meunier M et al., Arthritis&Rheumatism, vol. 63,S572.

Mihara et al., "Humanized antibody to human interleukin-6 receptor inhibits the development of collagen arthritis in cynomolgus monkeys" Clinical Immunology 98(3):319-326 (Mar. 2001).

Morcos et al., "PII-61 Pharmacokinetics (PK) and pharmacodynamics (PD) of single subcutaneous (SC) doses of Tocilizumab (TCZ) administered with and without rHuPH20, a recombinant human hyaluronidase, in healthy volunteers" Clinical Pharmacology and Therapeutics—112th Annual Meeting of the American Society for Clinical Pharmacology and Therapeutics; Dallas, TX, Mar. 2-5, 2011 89(Suppl. 1): S57 (Feb. 2011).

Mukaida et al., "Theme of the month: Cytokines and Hematopoietic Factors" Clinical Test (English Translation), 35:447-452 ( 1991).

NCT01209689, pp. 1-5 ( Dec. 2012).

New Hope for Children who suffer from juvenile arthritis, American College of Rheumatology (2003).

Nishimoto et al., "[2008] [FRI0153] Three-year extension of the samurai study confirms tocilizumab to prevent joint destruction in patients with rheumatoid arthritis" Annals of the Rheumatic Diseases 67(Suppl II):335 ( 2008).

Nishimoto et al., "Long-term safety and efficacy of tocilizumab, an anti-IL-6 receptor monoclonal antibody, in monotherapy, in patients with rheumatoid arthritis (the STREAM study): evidence of safety and efficacy in a 5-year extension study" Ann Rheum Dis 68(10):1580-1584 (Oct. 2009).

Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease" Blood 112(10):3959-64 ( 2008).

Nishimoto et al., "Study of active controlled monotherapy used for rheumatoid arthritis, an IL-6 inhibitor (SAMURAI): evidence of clinical and radiographic benefit from an x ray reader-blinded randomised controlled trial of tocilizumab" Ann Rheum Dis. 66(9):1162-7 ( 2007).

Oen et al., "Interleukin 6 and Autoantibodies in Juvenile Rheumatoid Arthritis" The Journal of Rheumatology 20:1949-1956( 1993).

Ogata et al., "Anti-IL-6 receptor antibody does not ameliorate radiation pheumonia in mice" Experimental and Therapeutic Medicine 4:273-276 ( 2012).

Ogata et al., "Early administration of IL-6RA does not prevent radiation-induced lung injury in mice" Radiation Oncology 5(26):1-6 ( 2010).

Ohta et al., "A Phase I/II Study Evaluating the Safety, Pharmacokinetics and Clinical Response of Tocilizumab for Subcutaneous Administration in Patients With Rheumatoid Arthritis" Ann Rheum Dis (Abstract SAT0168), 69( Suppl 3):543 (Jun. 2010).

Ohta et al., "How change in tender and swollen joint counts in patients who switched to intravenous infusion after completing a clinical study of subcutaneous tocilizumab?" Ann Rheum Dis (Abstract SAT0297), 70( Suppl 3):619 (2011).

Ohta et al., "Mechanism-based approach using a biomarker response to evaluate tocilizumab subcutaneous injection in patients with rheumatoid arthritis with an inadequate response to synthetic DMARDs (Matsuri study)" Journal of Clinical Pharmacology 54(1):109-119 ( 2014).

Ohta et al., "Optimal Dose Prediction by Pharmacokinetic and Biomarker Response of Subcutaneous Tocilizumab Treatment A Phase I/II Study Evaluating the Safety, Pharmacokinetics and Clinical Response in Patients with Rheumatoid Arthritis. Abstract:1115 DOI: 10.1002/art.28882 Retrieved from the Internet on Jan. 30, 2012:URL:http://www.blackwellpublishing.com/acrmeeting/abstract.asp?MeetingID=774&id=89764" Arthritis Rheum. 62(Suppl 10) (Oct. 2010).

Ong and Denton, "Innovative therapies for systemic sclerosis" Curr Opin Rheumatol. 22(3):264-72 ( 2010).

Pascual et al., "Role of interleukin-1 (IL-1) in the pathogenesis of systemic onset juvenile idiopathic arthritis and clinical response to IL-1 blockade" The Journal of Experimental Medicine 201(9):1479-1486 (May 2, 2005).

PharmaTimes ( Jul 15, 2015).

Ponte et al., "Giant cell arteritis: Current treatment and management" World J. Clin Cases 3(6):484-494 ( 2015).

Prevoo et al., "Modified disease activity scores that include twenty-eight-joint counts; Development and validation in a prospective longitudinal study of patients with rheumatoid arthritis" Arthritis Rheum 38(1):44-48 (Jan. 1995).

Quartier et al., "Efficacy of etanercept for the treatment of juvenile idiopathic arthritis according to the onset type" Arthritis & Rheumatism 48(4):1093-1101 (Apr. 2003).

Quintieri et al., "Formation and antitumor activity of PNU-159682, a major metabolite of nemorubiein in human liver microsomes" Clin Cancer Res 11:1608-17 (Feb. 15, 2005).

(56) References Cited

OTHER PUBLICATIONS

Radstake et al., "The pronounced Th17 profile in systemic sclerosis (SSc) together with intracellular expression of TGFbeta and IFNgamma distinguishes SSc phenotypes" PLoS One 4(6 Suppl e5903):1-9 (2009).
Richard-Miceli et al., "Tumour necrosis factor-a blockers in rheumatoid arthritis" BioDrugs 15(4):251-259 ( 2001).
Rooney et al., "Inflammatory Cytokine Responses in Juvenile Chronic Arthritis" British Journal of Rheumatology 34:454-460 (1995).
Rubio-Rivas et al., "Mortality and survival in systemic sclerosis: Systematic review and meta-analysis" Seminars in Arthritis Rheum. 44:208-219 ( 2014).
Russo et al., "Etanercept in systemic juvenile idiopathic arthritis" Clinical and Experimental Rheumatology 20:723-726 ( 2002).
Saito et al., "Role of interleukin-6 in bleomycin-induced lung inflammatory changes in mice" Am J Respir Cell Mol Biol. 38(5):566-571 (May 2008).
Salvarani et al., "Primary central nervous system vasculitis presenting with intracranial hemorrhage" Arthritis Rheum. 63(11):3598-606 ( 2011).
Salvarani et al., "Tocilizumab: a novel therapy for patients with large-vessel vasculitis" Arthritis and Rheumatism; Manuscript ID:ar-11-0531; Date Submitted by the Author Apr. 5, 2011, 15 pages.
Sato et al., "Reshaping a human antibody to inhibit the interleukin 6-dependent tumor cell growth" Cancer Research 53:851-856 (Feb. 15, 1993).
Sato et al., "Serum levels of interleukin-6 and interleukin-10 correlate with total skin thickness score in with systemic sclerosis" J Dermatol Sci. 27(2):140-146 (Oct. 2001).
Schlesselman et al., "Tocilizumab: A humanized anti-IL-6 receptor monoclonal antibody for the treatment of rheumatoid arthritis" Formulary (Retrieved from the Internet onJan. 26, 2012:URL: http://license.icopyright.net/user/vie wFreeUse.act?fuid=MTU1NzIyNTA%3D), (Aug 1, 2008).
Schmeling et al., "A combination of etanercept and methotrexate for the treatment of refractory juvenile idiopathic arthritis: a pilot study" Ann. Rheum. Dis. 60:410-412 ( 2001).
Seitz et al., "Rapid induction of remission in large vessel vasculitis by IL-6 blockade. A case series" Swiss Med Wkly. (141:w13156. doi: 10.4414/smw.2011.13156. www.smw.ch),:E1-E4 (Jan. 17, 2011).
Shima et al., "The skin of patients with systemic sclerosis softened during the treatment with anti-IL-6 receptor antibody tocilizumab" Rheumatology (doi:10.1093/rheumatology/keq275) 49(12):2408-12 ( 2010).
Silman, Oxford Textbook of Rheumatology "Epidemiology and the rheumatic diseases" P. J. Maddison, David A. Isenberg, Patricia Woo, David N. Glass and Ferdinand Breedveld,Oxford University Press,:499-513 ( 1993).
Steen and Medsger, "Changes in causes of death in systemic sclerosis, 1972-2002" Ann Rheum Dis. 66:940-944 ( 2007).
Stone et al., "Efficacy and Safety of Tocilizumab in Patients with Giant Cell Arteritis: Primary and Secondary Outcomes from a Phase 3, Randomized, Double-Blind, Placebo-Controlled Trial [abstract]" Arthritis Rheumatol (http://acrabstracts.org/abstract/efficacy-and-safety-of-tocilizumab-in-patients-with-giant-cell-arteritis-primary-and-secondary-outcomes-from-a-phase-3-randomized-double-blind-placebo-controlled-trial/ [Accessed on Mar. 30, 2017]),(68 Suppl 10) ( 2016).
Stone et al., "The GiACTA Trial Tocilizumab for Sustained Glucocorticoid-Free Remission in Giant Cell Arteritis [Slides]" Slides American College of Rheumatology Annual Meeting, Washington, DC, pp. 21 (2016).
Stone et al., "The GiACTA Trial What is the Optimal Dose of Tocilizumab for Giant Cell Arteritis?" Slides International ANCA/Vasculitis Workshop, Tokyo, Japan, pp. 27 ( Mar. 27, 2017).
Take et al., "Successful Treatment with Auranofin in a Patient with Elderly-onset Still's disease" Journal of Medicine 25(6) ( 1994).

Takei et al., "Safety and efficacy of high dose etanercept in treatment of juvenile rheumatoid arthritis" The Journal of Rheumatology 28(7):1677-1680 ( 2001).
Tamura et al., "Soluble interleukin-6 receptor triggers osteoelast formation by interleukin 6" Proc Natl Acad Sci U S A. 90(24):11924-8 ( 1993).
Tanaka et al., "Anti-interleukin-6 receptor antibody, tocilizumab, for the treatment of autoimmune diseases" FEBS Lett. 585(23):3699-3709 (Dec. 1, 2011).
Tashkin et al., "Cyclophosphamide versus Placebo in Scleroderma Lung Disease" N. Engl. J. Med. 354(25):2655-66 ( 2006).
Taub et al., "Hepatoprotection via the IL-6/Stat3 pathway" J Clin Invest. 112(7):978-80 ( 2003).
Tilg et al., "Interleukin-6 (IL-6) as an anti-inflammatory cytokine: induction of circulating IL-1 receptor antagonist and soluble tumor necrosis factor receptor p55" Blood 83(1):113-118 ( 1994).
Ulich et al., "Intratracheal injection of endotoxin and cytokines" American Journal of Pathology 138(5):1097-1101 (May 1991).
University Hospital Inselspital, Berne, "Tocilizumab for Patients with Giant Cell Arteritis" (ClinicalTrials.gov identifier: NCT01450137; First received Oct. 3, 2011; Last updated Jun. 19, 2014; Last verified Jun. 2014; Retrieved Aug. 26, 2015),:1-4 http://www.clinicaltrials.gov/ct2/show/NCT01450137.
Unizony et al., "Tocilizumab For the Treatment of Large Vessel Vasculitis (Giant Cell Arteritis, Takayasu Arteritis) and Polymyalgia Rheumatica: A Case Series" Arthritis & Rheumatism (Abstracts of the 75th Annual Scientific Meeting of the American College of Rheumatology/46th Annual Scientific Meeting; Chicago, Illinois Nov. 4-9, 2011), 63( Suppl 10):S589 (Nov. 2011).
US Package Insert (USPI) for ACTEMRA® (tocilizumab) revised copy from GRASS, PID2011-02647), pp. 1-32 ( Apr. 2011).
van der Heijde, "How to read radiographs according to the Sharp/van der Heijde method" J Rheumatol 27:261-3 ( 2000).
van Gestel et al., "Validation of Rheumatoid Arthritis Improvement Criteria that Include Simplified Joint Counts" Arthritis Rheum. 41:1845-1850 ( 1998).
Weinblatt et al., "Adalimumab, a fully human anti-tumor necrosis factor alpha monoclonal antibody, for the treatment of rheumatoid arthritis in patients taking concomitant methotrexate: the ARMADA trial" Arthritis Rheum. 48(1):35-45 (2003).
Wendling et al., "Treatment of severe rheumatoid arthritis by anti-interleukin 6 monoclonal antibody" J. Rheumatol 20:259-262 ( 1993).
Weyand et al., "Treatment of giant cell arteritis: interleukin-6 as a biologic marker of disease activity" Arthritis & Rheumatism 43(5):1041-1048 (May 2000).
Yilmaz et al., "Cytokine levels in serum of patients with juvenile rheumatoid arthritis" Clin Rheumatol 20:30-35 ( 2001).
Yokota et al., "Efficacy and safety of tocilizumab in patients with systemic-onset juvenile idiopathic arthritis: a randomised, double-blind, placebo-controlled, withdrawal phase III trial" Lancet 371(9617):998-1006 (Mar. 22, 2008).
Yokota et al., "Therapeutic efficacy of humanized recombinant anti-interleukin-6 receptor antibody in children with systemic-onset juvenile idiopathic arthritis" Arthritis & Rheumatism 52(3):818-825 (Mar. 2005).
Yokota et al., "Tocilizumab: molecular intervention therapy in children with systemic juvenile idiopathic arthritis" Expert Rev Clin Immunol. 6(5):735-743 (Sep. 2010).
Yoshizaki et al., "Therapy of rheumatoid arthritis by blocking IL-6 signal transduction with a humanized anti-IL-6 receptor antibody" Springer Seminars Immunopathology 20:247-259 ( 1998).
Herlin, T., et al., "Tocilizumab: The evidence for its place in the treatment of juvenile idiopathic arthritis" Core Evid 4:181-189 (Aug. 6, 2009).
McKain, S., et al., Email Communication re: Ohta et al., "Optimal Dose Prediction by Pharmacokinetic and Biomarker Response of Subcutaneous Tocilizumab Treatment A Phase I/II Study Evaluating the Safety, Pharmacokinetics and Clinical Response in Patients with Rheumatoid Arthritis. Abstract: 1115 62(Suppl 10) was posted to Arthritis and Rheum. on Sep. 28, 2010":1 (Aug. 18, 2020).

(56) References Cited

OTHER PUBLICATIONS

Nagafuchi, H., et al., "Monoclonal antibody therapy in systemic vasculitis" Jap J Clin Exp Med (In Japanese with Eng. Translation), 238(6):682-686 (Aug. 6, 2011).

Yamada, H., et al., "Evolving medical care for autoimmune diseases and issues thereof: Vasculitis syndrome" Jap J Clin Exp Med (In Japanese with Eng. Translation), 230(9):746-749 (Aug. 29, 2009).

* cited by examiner

```
  1  DIQMTQSPSS  LSASVGDRVT  ITCRASQDIS  SYLNWYQQKP  GKAPKLLIYY   50
 51  TSRLHSGVPS  RFSGSGSGTD  FTFTISSLQP  EDIATYYCQQ  GNTLPYTFGQ  100
101  GTKVEIKRTV  AAPSVFIFPP  SDEQLKSGTA  SVVCLLNNFY  PREAKVQWKV  150
151  DNALQSGNSQ  ESVTEQDSKD  STYSLSSTLT  LSKADYEKHK  VYACEVTHQG  200
201  LSSPVTKSFN  RGEC  SEQ ID NO. 1                              214
```

FIG. 7A

```
  1  pEVQLQESGPG  LVRPSQTLSL  TCTVSGYSIT  SDHAWSWVRQ  PPGRGLEWIG   50
 51  YISYSGITTY   NPSLKSRVTM  LRDTSKNQFS  LRLSSVTAAD  TAVYYCARSL  100
101  ARTTAMDYWG   QGSLVTVSSA  STKGPSVFPL  APSSKSTSGG  TAALGCLVKD  150
151  YFPEPVTVSW   NSGALTSGVH  TFPAVLQSSG  LYSLSSVVTV  PSSSLGTQTY  200
201  ICNVNHKPSN   TKVDKKVEPK  SCDKTHTCPP  CPAPELLGGP  SVFLFPPKPK  250
251  DTLMISRTPE   VTCVVVDVSH  EDPEVKFNWY  VDGVEVHNAK  TKPREEQYNS  300
301  TYRVVSVLTV   LHQDWLNGKE  YKCKVSNKAL  PAPIEKTISK  AKGQPREPQV  350
351  YTLPPSRDEL   TKNQVSLTCL  VKGFYPSDIA  VEWESNGQPE  NNYKTTPPVL  400
401  DSDGSFFLYS   KLTVDKSRWQ  QGNVFSCSVM  HEALHNHYTQ  KSLSLSPG    448
     SEQ ID NO. 2
```

FIG. 7B

SEQUENCE LISTING

```
<160> NUMBER OF SEQ ID NOS: 8

<210> SEQ ID NO 1
<211> LENGTH: 214
<212> TYPE: PRT
<213> ORGANISM: Artificial sequence
<220> FEATURE:
<223> OTHER INFORMATION: Sequence is synthesized.

<400> SEQUENCE: 1

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Ile Ser
                 20                  25                  30

Ser Tyr Leu Asn Trp Tyr Gln Gln Lys Pro Gly Lys Ala Pro Lys
                 35                  40                  45

Leu Leu Ile Tyr Tyr Thr Ser Arg Leu His Ser Gly Val Pro Ser
                 50                  55                  60

Arg Phe Ser Gly Ser Gly Ser Gly Thr Asp Phe Thr Phe Thr Ile
                 65                  70                  75

Ser Ser Leu Gln Pro Glu Asp Ile Ala Thr Tyr Tyr Cys Gln Gln
                 80                  85                  90

Gly Asn Thr Leu Pro Tyr Thr Phe Gly Gln Gly Thr Lys Val Glu
                 95                 100                 105
```

```
Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 2
<211> LENGTH: 448
<212> TYPE: PRT
<213> ORGANISM: Artificial sequence
<220> FEATURE:
<223> OTHER INFORMATION: sequence is synthesized
<220> FEATURE:
<221> NAME/KEY: Xaa
<222> LOCATION: 1
<223> OTHER INFORMATION: Predominantly pyroglutamic acid (pE)

<400> SEQUENCE: 2

Xaa Val Gln Leu Gln Glu Ser Gly Pro Gly Leu Val Arg Pro Ser
  1               5                  10                  15

Gln Thr Leu Ser Leu Thr Cys Thr Val Ser Gly Tyr Ser Ile Thr
            20                  25                  30

Ser Asp His Ala Trp Ser Trp Val Arg Gln Pro Pro Gly Arg Gly
            35                  40                  45

Leu Glu Trp Ile Gly Tyr Ile Ser Tyr Ser Gly Ile Thr Thr Tyr
            50                  55                  60

Asn Pro Ser Leu Lys Ser Arg Val Thr Met Leu Arg Asp Thr Ser
            65                  70                  75

Lys Asn Gln Phe Ser Leu Arg Leu Ser Ser Val Thr Ala Ala Asp
            80                  85                  90

Thr Ala Val Tyr Tyr Cys Ala Arg Ser Leu Ala Arg Thr Thr Ala
            95                 100                 105

Met Asp Tyr Trp Gly Gln Gly Ser Leu Val Thr Val Ser Ser Ala
            110                 115                 120

Ser Thr Lys Gly Pro Ser Val Phe Pro Leu Ala Pro Ser Ser Lys
            125                 130                 135

Ser Thr Ser Gly Gly Thr Ala Ala Leu Gly Cys Leu Val Lys Asp
            140                 145                 150

Tyr Phe Pro Glu Pro Val Thr Val Ser Trp Asn Ser Gly Ala Leu
            155                 160                 165

Thr Ser Gly Val His Thr Phe Pro Ala Val Leu Gln Ser Ser Gly
            170                 175                 180

Leu Tyr Ser Leu Ser Ser Val Val Thr Val Pro Ser Ser Ser Leu
            185                 190                 195

Gly Thr Gln Thr Tyr Ile Cys Asn Val Asn His Lys Pro Ser Asn
            200                 205                 210
```

```
Thr Lys Val Asp Lys Lys Val Glu Pro Lys Ser Cys Asp Lys Thr
            215                 220                 225

His Thr Cys Pro Pro Cys Pro Ala Pro Glu Leu Leu Gly Gly Pro
            230                 235                 240

Ser Val Phe Leu Phe Pro Pro Lys Pro Lys Asp Thr Leu Met Ile
            245                 250                 255

Ser Arg Thr Pro Glu Val Thr Cys Val Val Asp Val Ser His
            260                 265                 270

Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp
            305                 310                 315

Leu Asn Gly Lys Glu Tyr Lys Cys Lys Val Ser Asn Lys Ala Leu
            320                 325                 330

Pro Ala Pro Ile Glu Lys Thr Ile Ser Lys Ala Lys Gly Gln Pro
            335                 340                 345

Arg Glu Pro Gln Val Tyr Thr Leu Pro Pro Ser Arg Asp Glu Leu
            350                 355                 360

Thr Lys Asn Gln Val Ser Leu Thr Cys Leu Val Lys Gly Phe Tyr
            365                 370                 375

Pro Ser Asp Ile Ala Val Glu Trp Glu Ser Asn Gly Gln Pro Glu
            380                 385                 390

Asn Asn Tyr Lys Thr Thr Pro Pro Val Leu Asp Ser Asp Gly Ser
            395                 400                 405

Phe Phe Leu Tyr Ser Lys Leu Thr Val Asp Lys Ser Arg Trp Gln
            410                 415                 420

Gln Gly Asn Val Phe Ser Cys Ser Val Met His Glu Ala Leu His
            425                 430                 435

Asn His Tyr Thr Gln Lys Ser Leu Ser Leu Ser Pro Gly
            440                 445

<210> SEQ ID NO 3
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 3

Arg Ala Ser Gln Asp Ile Ser Ser Tyr Leu Asn
 1               5                  10

<210> SEQ ID NO 4
<211> LENGTH: 7
<212> TYPE: PRT
<213> ORGANISM: Artificial sequence
<220> FEATURE:
<223> OTHER INFORMATION: Sequence is synthesized.

<400> SEQUENCE: 4

Tyr Thr Ser Arg Leu His Ser
 1               5

<210> SEQ ID NO 5
<211> LENGTH: 9
<212> TYPE: PRT
<213> ORGANISM: Artificial sequence
```

```
<220> FEATURE:
<223> OTHER INFORMATION: Sequence is synthesized.

<400> SEQUENCE: 5

Gln Gln Gly Asn Thr Leu Pro Tyr Thr
 1               5

<210> SEQ ID NO 6
<211> LENGTH: 6
<212> TYPE: PRT
<213> ORGANISM: Artificial sequence
<220> FEATURE:
<223> OTHER INFORMATION: Sequence is synthesized.

<400> SEQUENCE: 6

Ser Asp His Ala Trp Ser
 1               5

<210> SEQ ID NO 7
<211> LENGTH: 16
<212> TYPE: PRT
<213> ORGANISM: Artificial sequence
<220> FEATURE:
<223> OTHER INFORMATION: Sequence is synthesized.

<400> SEQUENCE: 7

Tyr Ile Ser Tyr Ser Gly Ile Thr Thr Tyr Asn Pro Ser Leu Lys
 1               5                  10                  15

Ser

<210> SEQ ID NO 8
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 8

Ser Leu Ala Arg Thr Thr Ala Met Asp Tyr
 1               5                  10
```

SUBCUTANEOUSLY ADMINISTERED ANTI-IL-6 RECEPTOR ANTIBODY

CROSS REFERENCE TO RELATED APPLICATIONS

This is a divisional application which claims priority under 35 USC § 120 to divisional application Ser. No. 15/668,445, filed Aug. 3, 2017 which claims priority under 35 USC § 120 to divisional application Ser. No. 14/062,026, filed Oct. 24, 2013 (now U.S. Pat. No. 9,750,752), which is a divisional of Non-provisional application Ser. No. 13/290,366, filed Nov. 7, 2011 (now U.S. Pat. No. 8,580,264), which claims priority under 35 USC § 119(e) to U.S. Provisional Application Ser. No. 61/411,015, filed on Nov. 8, 2010 and U.S. Provisional Application Ser. No. 61/542,615, filed on Oct. 3, 2011, which are incorporated by reference in entirety.

SEQUENCE LISTING

The instant application contains a Sequence Listing submitted via EFS-Web and is hereby incorporated by reference in its entirety. Said ASCII copy, created Dec. 21, 2018, is named P04494US7_SeqList.txt, and is 7,470 bytes in size.

FIELD OF THE INVENTION

The present application concerns methods for treating an IL-6-mediated disorder such as rheumatoid arthritis (RA), juvenile idiopathic arthritis (JIA), systemic JIA (sJIA), polyarticular course JIA (pcJIA), systemic sclerosis, or giant cell arteritis (GCA), with subcutaneously administered antibody that binds interleukin-6 receptor (anti-IL-6R antibody). In particular, it relates to identification of a fixed dose of anti-IL-6R antibody, e.g. tocilizumab, which is safe and effective for subcutaneous administration in patients with IL-6-mediated disorders. In addition, formulations and devices useful for subcutaneous administration of an anti-IL-6R antibody are disclosed.

BACKGROUND OF THE INVENTION

Rheumatoid arthritis is a progressive, systemic autoimmune disease characterized by synovitis that damages diarthroidal joints and is accompanied by fatigue, anemia, and osteopenia. Rheumatoid arthritis has a prevalence of 0.5% to 1.0% (Silman, A. J. "Epidemiology and the rheumatic diseases." In: Maddison P J, Isenberg D A, Woo P, Glass D N, eds. Oxford Textbook of Rheumatology: Oxford University Press: 499-513 (1993)) and a peak incidence between 40 and 60 years of age and affects primarily women. The cause of RA is not known; however, certain histocompatibility antigens are associated with poorer outcomes. Nonsteroidal anti-inflammatory drugs (NSAIDs) provide only symptomatic relief. Disease-modifying antirheumatic drugs (DMARDs), the cornerstone of RA treatment throughout all stages of the disease (Maddison et al., supra), maintain or improve physical function and retard radiographic joint damage (Brooks, P. M. "Clinical Management of rheumatoid arthritis." Lancet 341: 286-290 (1993)). More recently, biological compounds that target tumor necrosis factor alpha (TNF-α), B-cells, or T-cells have been used successfully to treat RA, but ~30% to 40% of patients fail to respond to these therapies (Bathon et al. New Eng. J. Med. 343: 1586-1592 (2000); Maini et al. Arthritis & Rheumatism 41: 1552-1563 (1998)).

Interleukin-6 (IL-6) is a proinflammatory, multifunctional cytokine produced by a variety of cell types. IL-6 is involved in such diverse processes as T-cell activation, B-cell differentiation, induction of acute phase proteins, stimulation of hematopoietic precursor cell growth and differentiation, promotion of osteoclast differentiation from precursor cells, proliferation of hepatic, dermal and neural cells, bone metabolism, and lipid metabolism (Hirano T. Chem Immunol. 51:153-180 (1992); Keller et al. Frontiers Biosci. 1: 340-357 (1996); Metzger et al. Am J Physiol Endocrinol Metab. 281: E597-E965 (2001); Tamura et al. Proc Natl Acad Sci USA. 90:11924-11928 (1993); Taub R. J Clin Invest 112: 978-980 (2003)). IL-6 has been implicated in the pathogenesis of a variety of diseases including autoimmune diseases, osteoporosis, neoplasia, and aging (Hirano, T. (1992), supra; and Keller et al., supra). IL-6 exerts its effects through a ligand-specific receptor (IL-6R) present both in soluble and membrane-expressed forms.

Elevated IL-6 levels have been reported in the serum and synovial fluid of RA patients, indicative of production of IL-6 by the synovium (Irano et al. Eur J Immunol. 18:1797-1801 (1988); and Houssiau et al. Arthritis Rheum. 1988; 31:784-788 (1988)). IL-6 levels correlate with disease activity in RA (Hirano et al. (1988), supra), and clinical efficacy is accompanied by a reduction in serum IL-6 levels (Madhok et al. Arthritis Rheum. 33:S154. Abstract (1990)).

Tocilizumab (TCZ) is a recombinant humanized monoclonal antibody of the immunoglobulin IgG1 subclass which binds to human IL-6R. Clinical efficacy and safety studies of intravenous (IV) TCZ have been completed or are conducted by Roche and Chugai in various disease areas, including adult-onset RA, systemic juvenile idiopathic arthritis and polyarticular juvenile idiopathic arthritis.

TCZ 8 mg/kg IV has been approved in over 70 countries for use in RA, including Japan and Europe. In the United States, TCZ IV (4 mg/kg and 8 mg/kg) has been approved in RA patients who have had an inadequate response to anti-TNF agents. Additionally, TCZ was approved for use in Castleman's disease in India and Japan.

On Apr. 15, 2011, the U.S. Food and Drug Administration approved TCZ, given alone or in combination with methotrexate, for the treatment of active systemic juvenile idiopathic arthritis (sJIA) (US Package Insert (USPI) for TCZ ACTEMRA®, April 2011). On Aug. 1, 2011, TCZ was also approved in the EU for the treatment of active sJIA who have responded inadequately to previous therapy with NSAIDs and systemic corticosteroids (CS), and TCZ can be given as monotherapy (in case of intolerance to MTX or where treatment with MTX is inappropriate) or in combination with MTX in patients 2 years of age and older (Summary of Product Characteristics (SmPC) for RoACTEMRA, Roche Registration Limited 6 Falcon Way Shire Park, Welwyn Garden City, AL7 1TW, United Kingdom, 4 Jun. 2010). The approved TCZ dose for sJIA patients weighing <30 kg is 12 mg/kg TCZ, and for patients weighing ≥30 kg is 8 mg/kg IV infusion every 2 weeks.

TCZ has been approved for treatment of polyarticular course juvenile idiopathic arthritis (pcJIA) in Japan based on the phase 3 study MRA318JP conducted in Japanese patients. WA19977 is an ongoing pivotal phase 3 study investigating the efficacy, safety, PK and PD of TCZ in children with pcJIA age of 2 to 17 years old.

TCZ has been intravenously administered to 2 Japanese patients with diffuse cutaneous systemic sclerosis (SSc) (Shima et al. Rheumatology 49:2408-12 (2010), doi: 10.1093/rheumatology/keq275)), and to 5 patients with SSC (Meunier et al. Ann. Rheum. Dis. 70 (Suppl 3):660 (2011)).

In patients with SSc, elevated levels of circulating IL-6 have been reported, particularly in patients with early disease. IL-6 is overexpressed in endothelial cells and fibroblasts of involved skin in patients with SSC (Koch et al. *Pathobiology* 61:239-46 (1993)). Elevated IL-6 levels have been detected in the bronchioalveolar lavage of patients with SSc. Dermal fibroblasts from patients with SSC have been reported to constitutively express higher levels of IL-6 compared with those of healthy controls (Kadono et al. *J. Rheumatol.* 25:296-301 (1998)). In addition, serum IL-6 levels correlate positively with skin sclerosis and acute-phase proteins (Ong and Denton, *Curr. Opin. Rheumatol.* 22:264-72 (2010)).

IL-6 has first been described as a potent growth and maturation factor for developing human plasma cells. IL-6 induces B-cell proliferation, antibody secretion, and survival of plasmablasts. Activated B cells produce IL-6 and other cytokines. In patients with SSc, polyclonal B-cell activation, presence of highly specific autoantibodies, and B-lymphocyte infiltration in diseased skin of patients have been detected. However, open-label trials of B cell-depleting antibodies in patients with SSC have resulted in inconclusive data to date (Bosello et al. *Arthritis Res. Therapy* 12:R54 (2010); Layfatis et al. *Arthritis Rheum.* 60; 578-83 (2009); Daoussis et al. *Rheumatology* 49:271-80 (2010)). Bosello et al. (2010) reported beneficial effects of B-cell depletion for patients with SSC that were associated with a reduction of serum IL-6 levels. In addition to its effects on B-cell function, IL-6 has specific effects on T cells. IL-6 promotes T-cell survival and Th17-lymphocyte differentiation and inhibits development of regulatory T cells. Th17 cells produce IL-17 and have been linked to development of autoimmune diseases. In an autocrine loop, IL-17 may induce IL-6 synthesis in human fibroblasts (Fossiez et al. *J. Exp. Med.* 813:2593-2603 (1996)). Increased circulating Th17 cells have also recently been reported in patients with SSC (Radstake et al. *PLoS ONE* 4(6):e5903. doi:10.1371/journal.pone.0005903. Atamas S P *Life Sci* 72:631-43 (2009)), whereas serum and bronchoalveolar lavage levels of IL-17 were found to be increased in patients with SSC and ILD (Kurasawa et al. *Arthritis Rheum* 43: 2455-63 (2000)).

Fibrosis gradually replaces the inflammatory phase of SSc. In vitro experiments with human dermal fibroblast cultures showed that IL-6 increased collagen type I, glycosaminoglycans, hyaluronic acid, and chondroitin sulfate production (Duncan and Berman *J. Invest. Dermatol.* 97:686-92 (1991)).

Giant cell arteritis (GCA) is a primary vasculitis involving large and medium sized arteries which is typically diagnosed by temporal artery biopsy. Signs and symptoms of GCA include elevated erythrocyte sedimentation rate (ESR) or new headaches. Adverse sequelae include: irreversible blindness (bilateral retinal or optic nerve ischemia), infarcation of brain, tongue, upper limb, or aortic aneurysm. GCA is an unmet medical need. High dose corticosteroids (CS) are the current standard of care, but more durable remissions are needed (50% of patients relapse), and steroid sparing treatment options are needed in view of steroid-related complications). Case studies reporting the use of TCZ in giant cell arteritis are: Seitz et al. *Swiss Med Wkly* 141: w13156 pgs. E1-E4 (2011); Salvarani et al. *Arth. and Rheum.* (April 2011); and Beyer et al. *Ann. Rheum. Dis.* pgs. 1-2 (2011), doi:10.1136/ard.2010.149351. In each of these studies TCZ was administered intravenously.

Patents and patent publications related to anti-IL-6R antibodies include: U.S. Pat. No. 5,171,840 (Kishimoto), U.S. Pat. No. 5,480,796 (Kishimoto), U.S. Pat. No. 5,670,373 (Kishimoto), U.S. Pat. No. 5,851,793 (Kishimoto), U.S. Pat. No. 5,990,282 (Kishimoto), U.S. Pat. No. 6,410,691 (Kishimoto), U.S. Pat. No. 6,428,979 (Kishimoto), U.S. Pat. No. 5,795,965 (Tsuchiya et al.), U.S. Pat. No. 5,817,790 (Tsuchiya et al.), U.S. Pat. No. 7,479,543 (Tsuchiya et al.), US 2005/0142635 (Tsuchiya et al.), U.S. Pat. No. 5,888,510 (Kishimoto et al.), US 2001/0001663 (Kishimoto et al.), US 2007/0036785 (Kishimoto et al.), U.S. Pat. No. 6,086,874 (Yoshida et al.), U.S. Pat. No. 6,261,560 (Tsujinaka et al.), U.S. Pat. No. 6,692,742 (Nakamura et al.), U.S. Pat. No. 7,566,453 (Nakamura et al.), U.S. Pat. No. 7,771,723 (Nakamura et al.), US 2002/0131967 (Nakamura et al.), US 2004/0247621 (Nakamura et al.), US 2002/0187150 (Mihara et al.), US 2005/0238644 (Mihara et al.), US 2009/0022719 (Mihara et al.), US 2006/0134113 (Mihara), U.S. Pat. No. 6,723,319 (Ito et al.), U.S. Pat. No. 7,824,674 (Ito et al.), US 2004/0071706 (Ito et al.), U.S. Pat. No. 6,537,782 (Shibuya et al.), U.S. Pat. No. 6,962,812 (Shibuya et al.), WO 00/10607 (Akihiro et al.), US 2003/0190316 (Kakuta et al.), US 2003/0096372 (Shibuya et al.), U.S. Pat. No. 7,320,792 (Ito et al.), US 2008/0124325 (Ito et al.), US 2004/0028681 (Ito et al.), US 2008/0124325 (Ito et al.), US 2006/0292147 (Yoshizaki et al.), US 2007/0243189 (Yoshizaki et al.), US 2004/0115197 (Yoshizaki et al.), US 2007/0148169 (Yoshizaki et al.), U.S. Pat. No. 7,332,289 (Takeda et al.), U.S. Pat. No. 7,927,815 (Takeda et al.), U.S. Pat. No. 7,955,598 (Yoshizaki et al.), US 2004/0138424 (Takeda et al.), US 2008/0255342 (Takeda et al.), US 2005/0118163 (Mizushima et al.), US 2005/0214278 (Kakuta et al.), US 2008/0306247 (Mizushima et al.), US 2009/0131639 (Kakuta et al.), US 2006/0142549 (Takeda et al.), U.S. Pat. No. 7,521,052 (Okuda et al.), US 2009/0181029 (Okuda et al.), US 2006/0251653 (Okuda et al.), US 2009/0181029 (Okuda et al.), US 2007/0134242 (Nishimoto et al.), US 2008/0274106 (Nishimoto et al.), US 2007/0098714 (Nishimoto et al.), US 2010/0247523 (Kano et al.), US 2006/0165696 (Okano et al.), US 2008/0124761 (Goto et al.), US 2009/0220499 (Yasunami), US 2009/0220500 (Kobara), US 2009/0263384 (Okada et al.), US 2009/0291076 (Morichika et al.), US 2009/0269335 (Nakashima et al.), US 2010/0034811 (Ishida), US 2010/0008907 (Nishimoto et al.), US 2010/0061986 (Takahashi et al.), US 2010/0129355 (Ohguro et al.), US 2010/0255007 (Mihara et al.), US 2010/0304400 (Stubenrach et al.), US 2010/0285011 (Imaeda et al.), US 2011/0150869 (Mitsunaga et al.), WO 2011/013786 (Maeda) and US 2011/0117087 (Franze et al.).

SUMMARY OF THE INVENTION

In a first aspect, the invention concerns a method of treating an IL-6-mediated disorder in a patient comprising subcutaneously administering an anti-IL-6 receptor (IL-6R) antibody to the patient, wherein the anti-IL-6R antibody is administered as a fixed dose of 162 mg per dose (e.g. administered every week or every two weeks). Embodiments of the disorder include: rheumatoid arthritis (RA), juvenile idiopathic arthritis (JIA), psoriatic arthritis, and Castleman's disease. Preferably, the anti-IL-6R antibody is tocilizumab.

The invention also concerns a method of treating rheumatoid arthritis in a patient comprising subcutaneously administering tocilizumab to the patient, wherein the tocilizumab is administered as a fixed dose of 162 mg per dose every week or every two weeks.

In another embodiment, the invention provides an article of manufacture comprising a subcutaneous administration device, which delivers to a patient a fixed dose of an anti-IL-6 receptor (IL-6R) antibody, wherein the fixed dose is selected from the group consisting of 162 mg, 324 mg, and 648 mg of the anti-IL-6R antibody.

The invention, in another aspect, concerns a method of inhibiting progression of structural joint damage in a rheumatoid arthritis patient comprising subcutaneously administering a fixed dose of 162 mg of an anti-IL-6R antibody to the patient every two weeks, wherein structural joint damage at week 24 or week 48 is found to be inhibited.

In addition, the invention provides a pharmaceutical composition comprising: an anti-IL-6R antibody in an amount from about 100 mg/mL to about 300 mg/mL, and hyaluronidase enzyme in an amount from about 1,400 to about 1,600 U/mL.

In further aspects, a method of treating an IL-6-mediated disorder in a patient is provided comprising subcutaneously administering such pharmaceutical composition to the patient, wherein the anti-IL-6R antibody is administered as a fixed dose of 324 mg per dose or 648 mg per dose, e.g. where the fixed dose is administered every four weeks or once every month.

The invention also concerns a method of treating an IL-6-mediated disorder in a patient comprising subcutaneously administering an anti-IL-6R antibody and a hyaluronidase enzyme to a patient, wherein the anti-IL-6R antibody is administered as a fixed dose of 324 mg per dose or 648 mg per dose (e.g. every four weeks or once every month).

The invention also concerns subcutaneously administering an anti-IL-6R antibody (e.g. tociluzumab) to a patient with an IL-6-mediated disorder. Examples of such disorders include: autoimmune diseases, osteoporosis, neoplasia, aging, rheumatoid arthritis (RA), juvenile idiopathic arthritis (JIA), systemic JIA (sJIA), polyarticular course JIA (pcJIA), psoriatic arthritis, Castleman's disease, Crohn's disease, multiple myeloma, polymyalgia rheumatica, glomerulonephritis, plasmacytoma or plasmacytosis, myeloma (including multiple myeloma), hyperimmunoglobulinemia, anemia, nephritis (such as mesangium proliferative nephritis), cachexia (including cancerous cachexia), tumors, T cell mediated disease (e.g. uveitis, chronic thyroiditis, delayed hypersensitivity, contact dermatitis, or atopic dermatitis), lupus (including lupus nephritis and systemic lupus erythmatosus), inflammatory bowel disease (including Crohn's disease and ulcerative colitis), pancreatitis, psoriasis, osteoarthritis, adult-onset Still's disease, mesothelioma, vasculitis, islet transplantation (e.g. pancreatic islet transplantation), myocardial infarction (heart failure, ischemia-induced severe arrhythmia), heart transplantation, prostate cancer, choroidal neovascularization (e.g. age-related macular degeneration, idiopathic choroidal neovascularization, cyopic choroidal neovascularization, idiopathic choroidal neovascularization), muscle atrophy, chronic rejection, ocular inflammatory disease (e.g. panuveitis, anterior aveitis, intermediate uveitis, scleritis, keratitis, orbital inflammation, optic neuritis, dry eye, diabetic retinopathy, proliferative vitreoretinopathy, postoperative inflammation), graft versus host disease (GVHD), fibrotic disorders (such as systemic sclerosis), giant cell arteritis (GCA), Takayasu's arteritis (TA), arteritis nodosa, ankylosing spondylitis, etc.

Optionally, the disorder is rheumatoid arthritis, juvenile idiopathic arthritis (JIA), systemic JIA (sJIA), polyarticular course JIA (pcJIA), giant cell arteritis (GCA), or systemic sclerosis.

In one embodiment, the anti-IL-6R antibody is subcutaneously administered to the patient with the IL-6-mediated disorder as a fixed dose of 162 mg per dose, wherein the fixed dose is subcutaneously administered every week, every two weeks, or every 10 days.

In a further aspect, the invention concerns a method of treating juvenile idiopathic arthritis (JIA) in a patient comprising subcutaneously administering an anti-IL-6 receptor (IL-6R) antibody to the patient in an amount effective to treat the JIA.

Additionally, a method of treating a fibrotic disease (e.g. systemic sclerosis) in a patient is provided which comprises subcutaneously administering an anti-IL-6 receptor (IL-6R) antibody to the patient in an amount effective to treat the fibrotic disease.

Moreover, the invention concerns a method of treating giant cell arteritis (GCA) in a patient comprising subcutaneously administering an anti-IL-6 receptor (IL-6R) antibody to the patient in an amount effective to treat the GCA.

Group 3 (162 mg QW, N=12): patients received 162 mg QW dosing for 15 weeks until the data-cut. Caucasian SC Study in RA patients (NP22623): N=13 for the 162 mg Q2W group+methotrexate (MTX) QW and N=14 for the 162 mg QW+MTX QW group. PK profiles from 4 and 8 mg/kg IV infusion every 4 weeks in RA patients in the Phase 2 dose-finding study LRO301 are illustrated for comparison. LRO301 was selected for comparison as PK from phase 2 and phase 3 studies were similar and Phase 3 had infrequent PK sampling (an observed mean PK profile could not be constructed appropriately).

Figure 5:
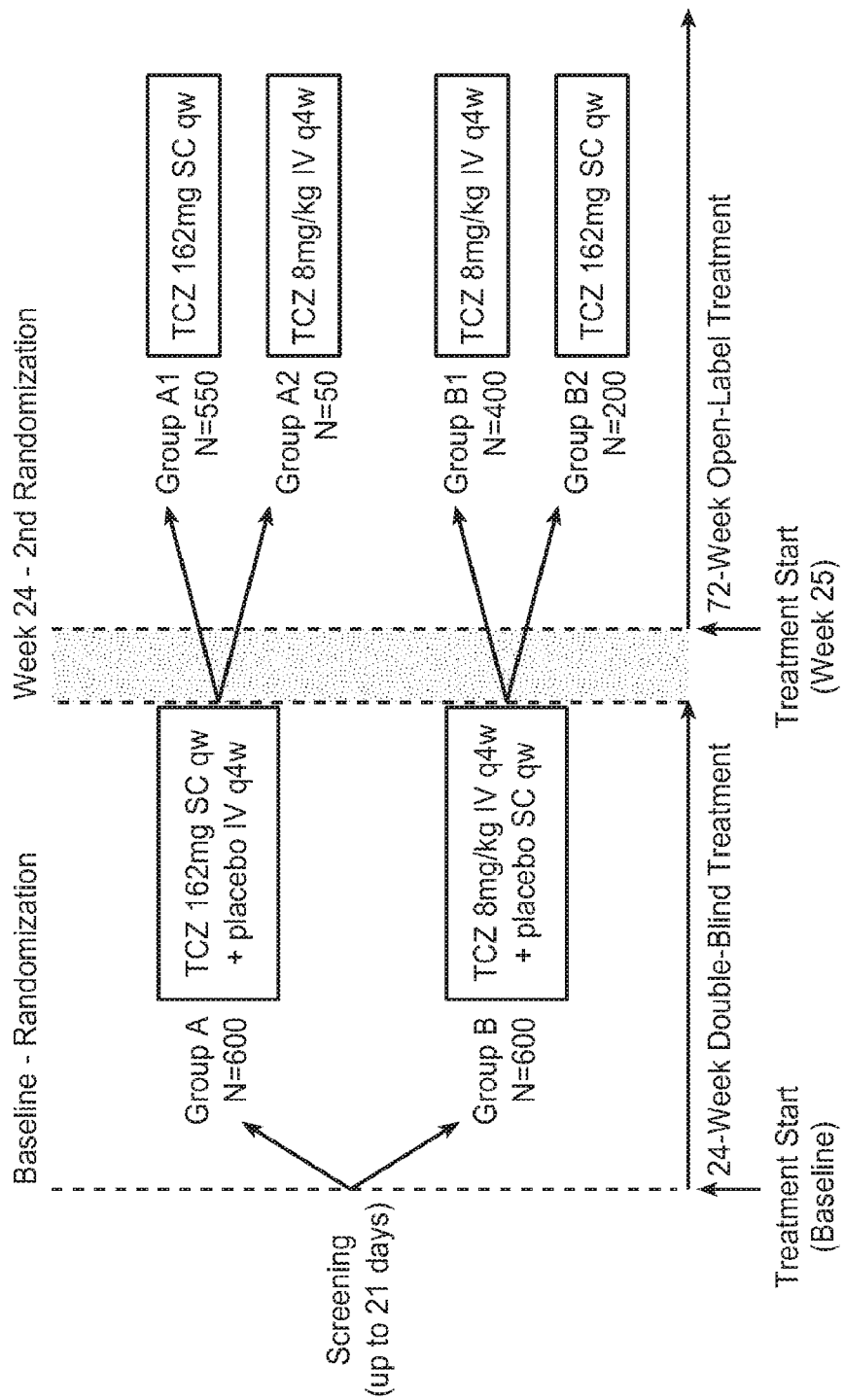

FIG. 5 depicts WA22762 Study Design as in Example 2.

Figure 6:
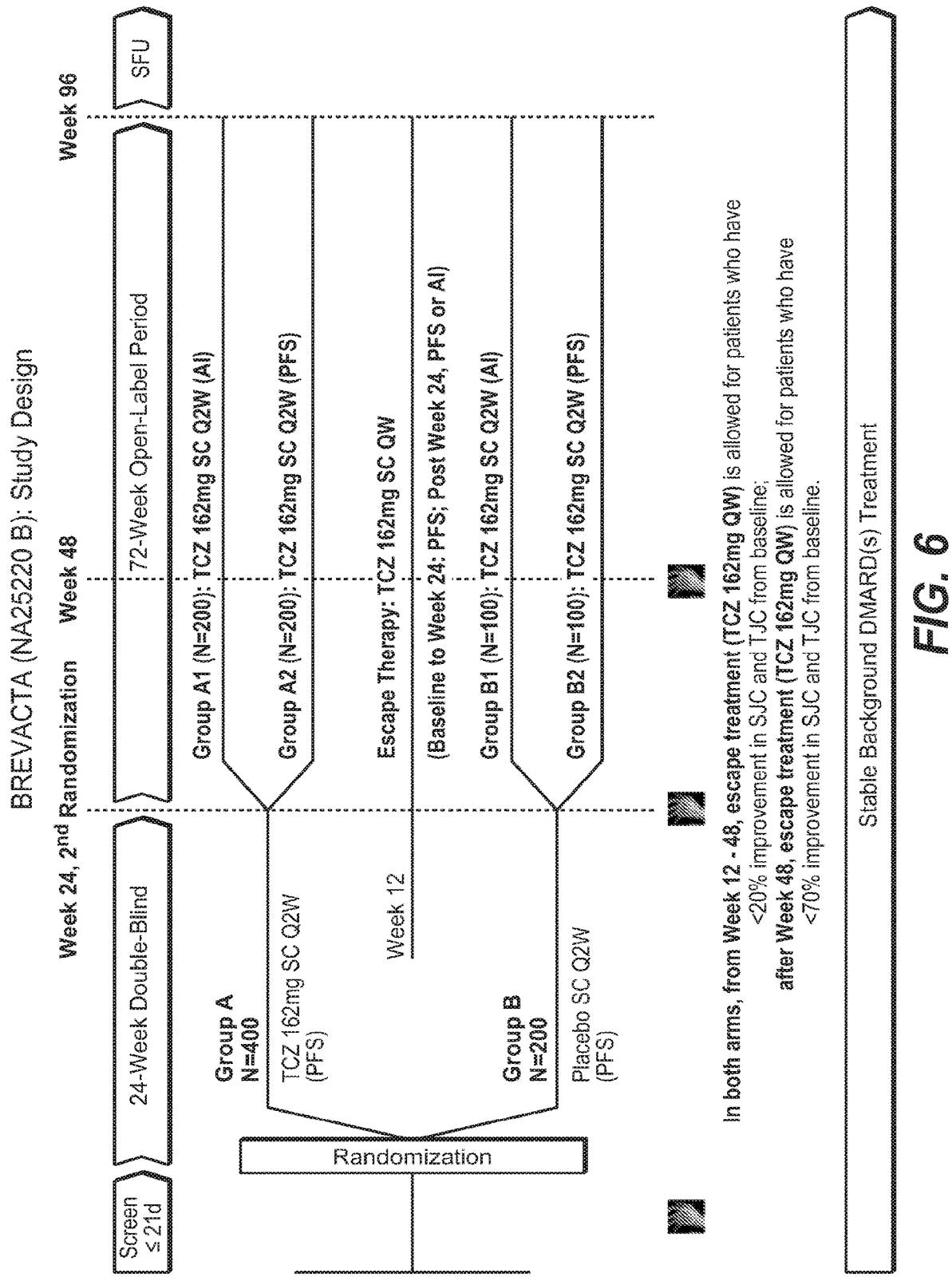

FIG. 6 depicts NA25220B Study Design as in Example 3.

FIGS. 7A and 7B depict the amino acid sequences of the light chain (FIG. 7A; SEQ ID NO:1) and heavy chain (FIG. 7B; SEQ ID NO:2) of Tocilizumab.

Figure 8A:
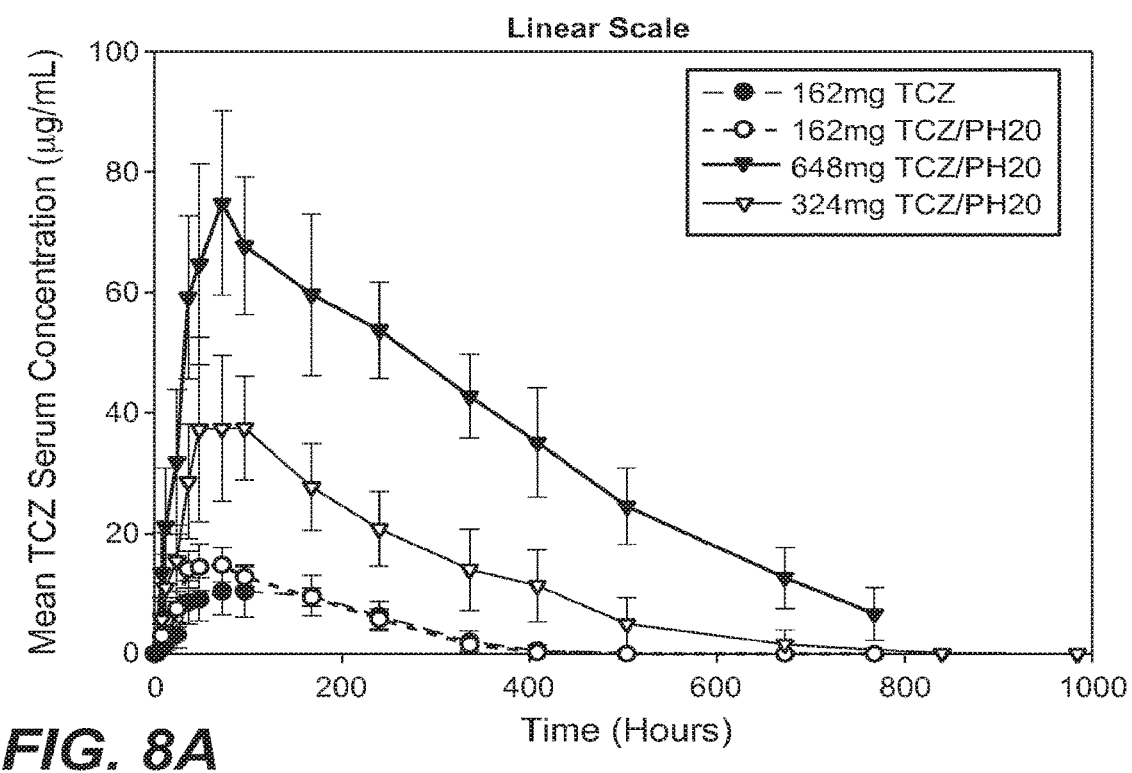
Figure 8B:
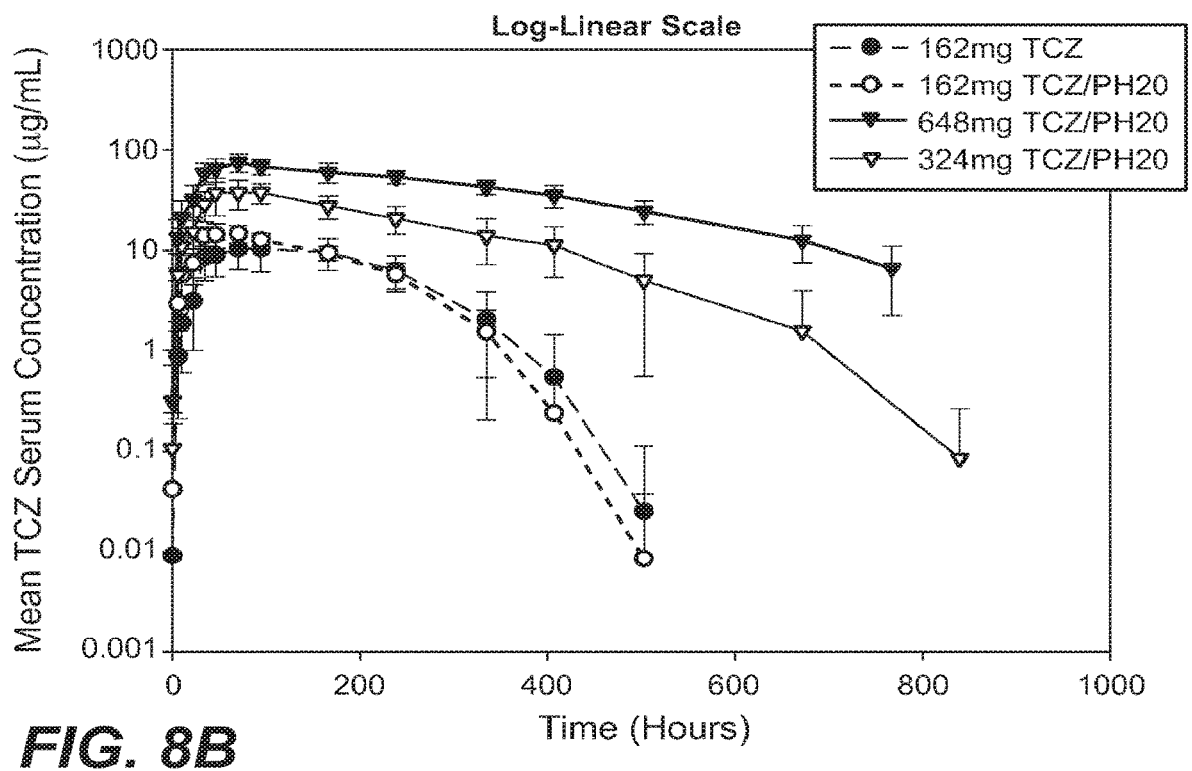

FIGS. 8A and 8B depict mean (±SD) Tocilizumab concentration-time profile by cohort for the study in Example 5. FIG. 8A provides linear scale; FIG. 8B provides log-linear scale. TCZ=tocilizumab; TCZ/PH20=tocilizumab co-formulated with rHuPH20.

Figure 9A:
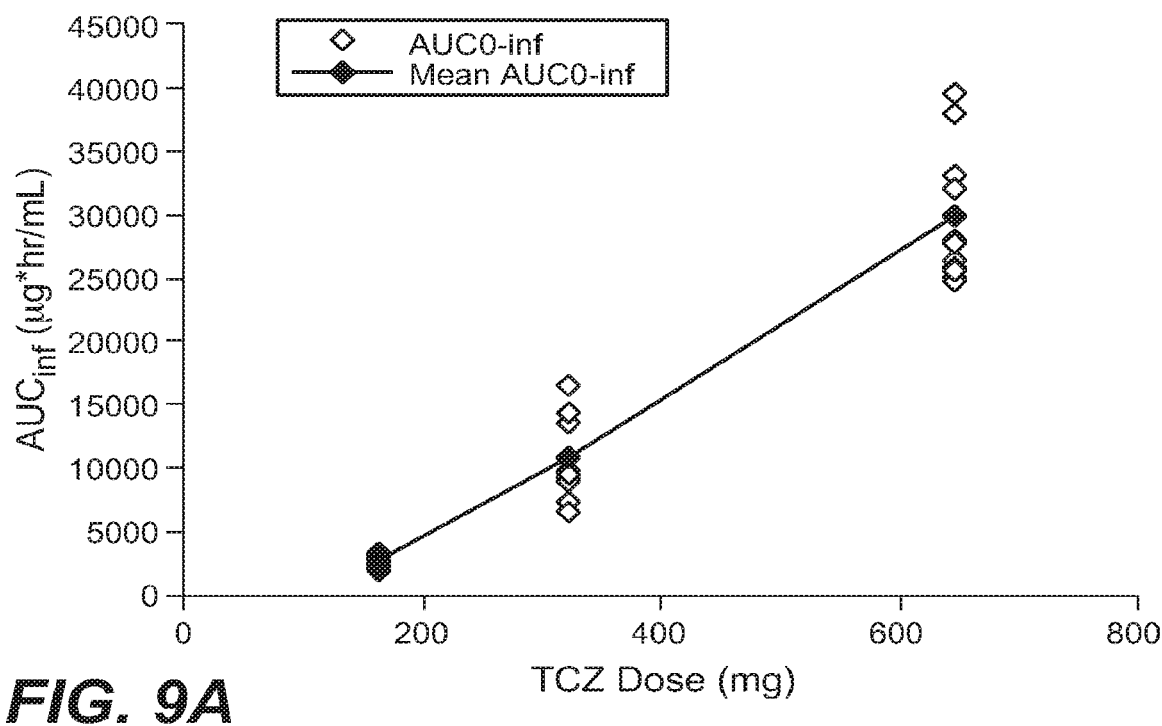
Figure 9B:
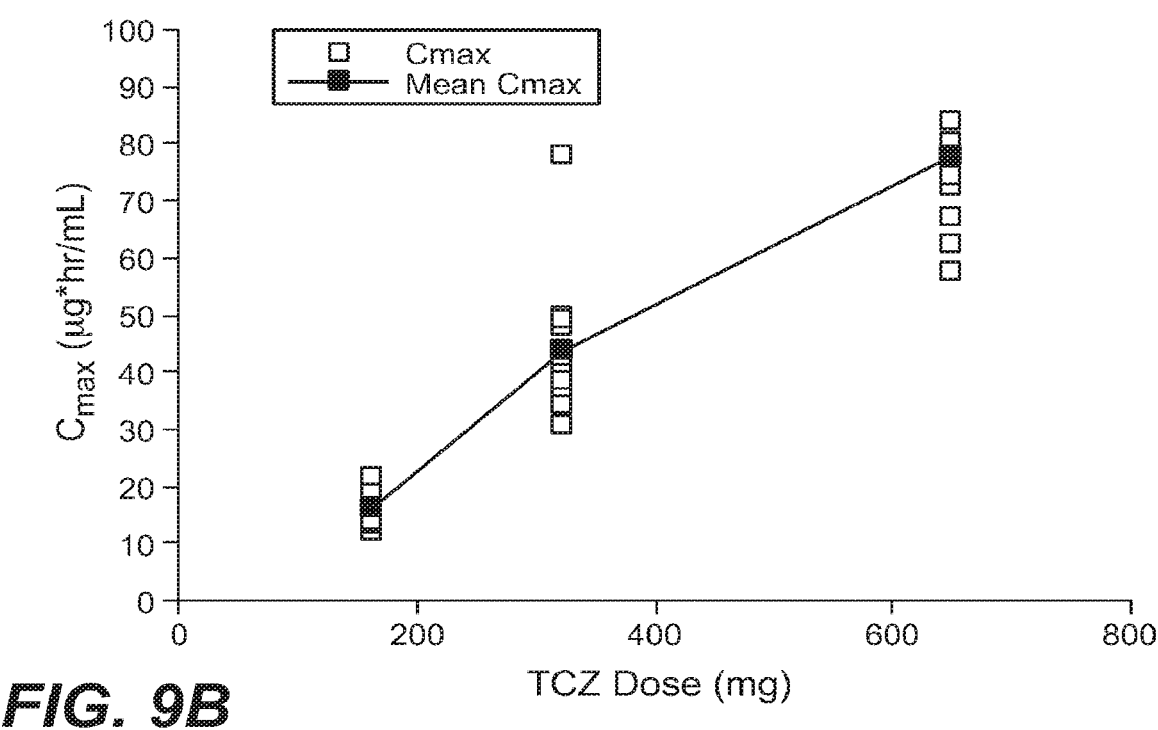

FIGS. 9A and 9B depict dose proportionality for Tocilizumab/rHuPH20 $AUC_{0-inf}$ (FIG. 9A) and $C_{max}$ (FIG. 9B).

Figure 10:
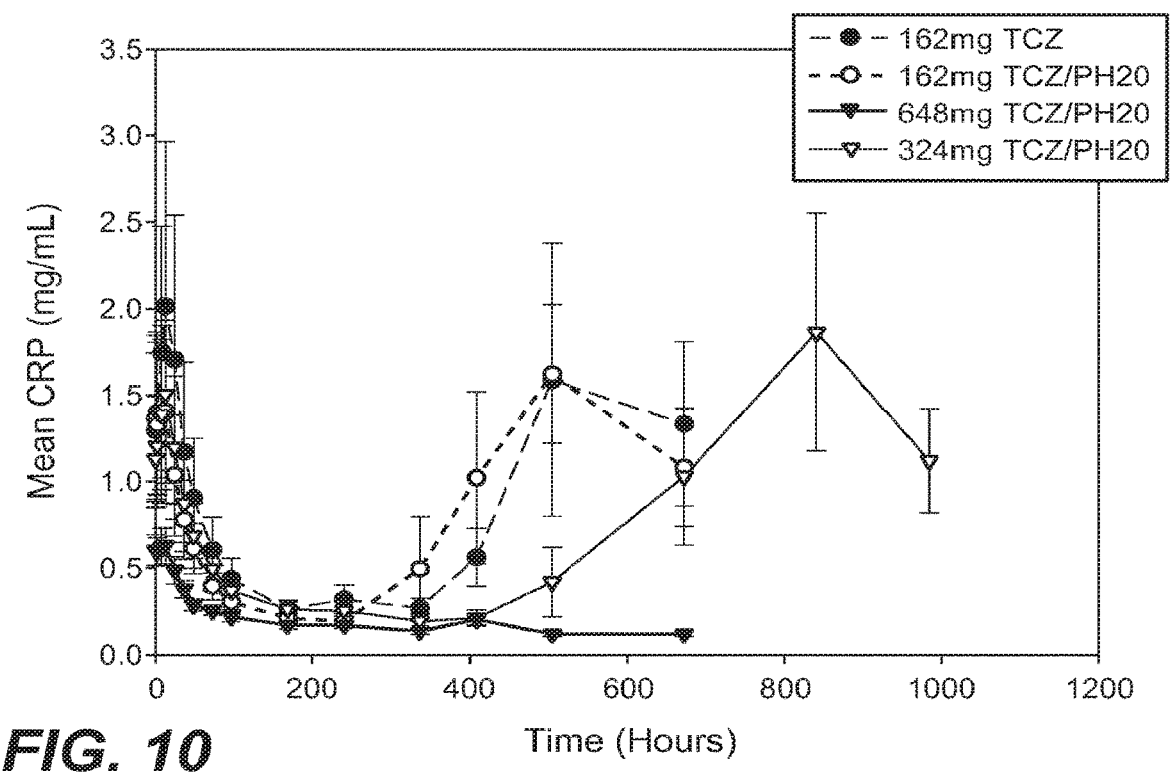

FIG. 10 depicts mean (±SEM) CRP concentration-time plot by cohort. TCZ=tocilizumab; TCZ/PH20=tocilizumab co-formulated with rHuPH20.

Figure 11:
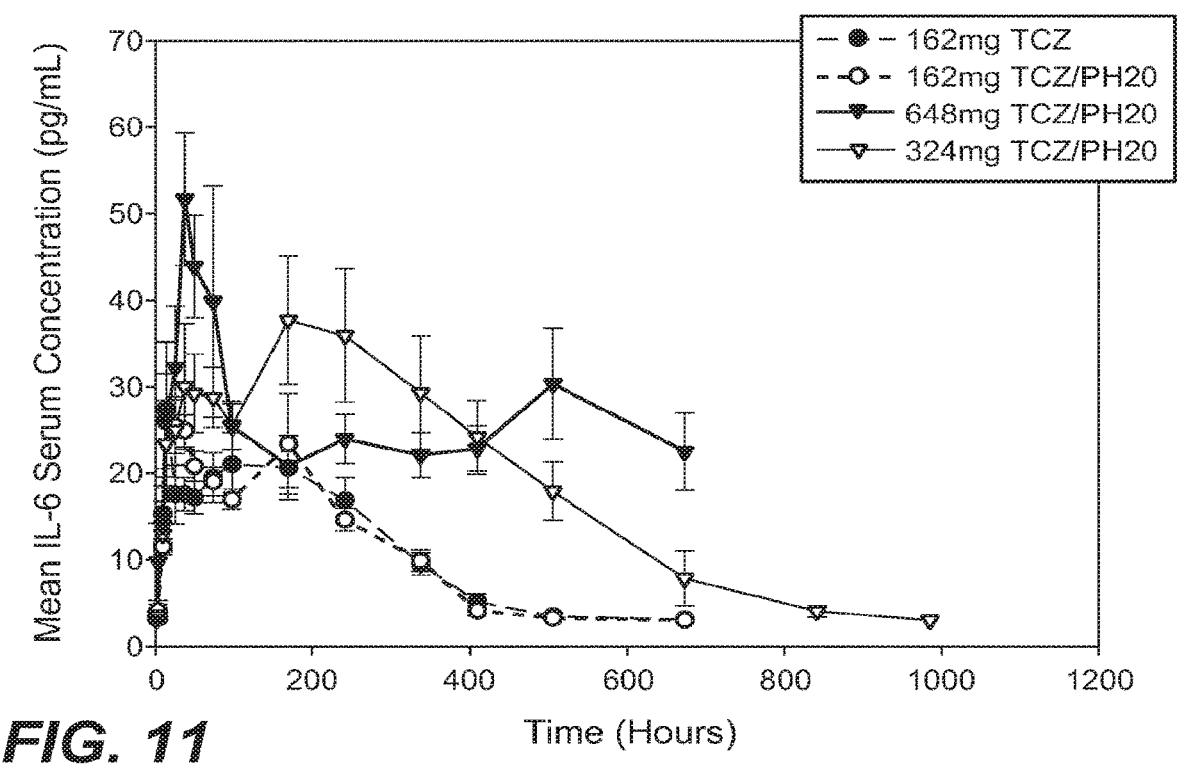

FIG. 11 depicts mean (±SEM) IL-6 concentration-time plot by cohort. TCZ=tocilizumab; TCZ/PH20=tocilizumab co-formulated with rHuPH20.

Figure 12:
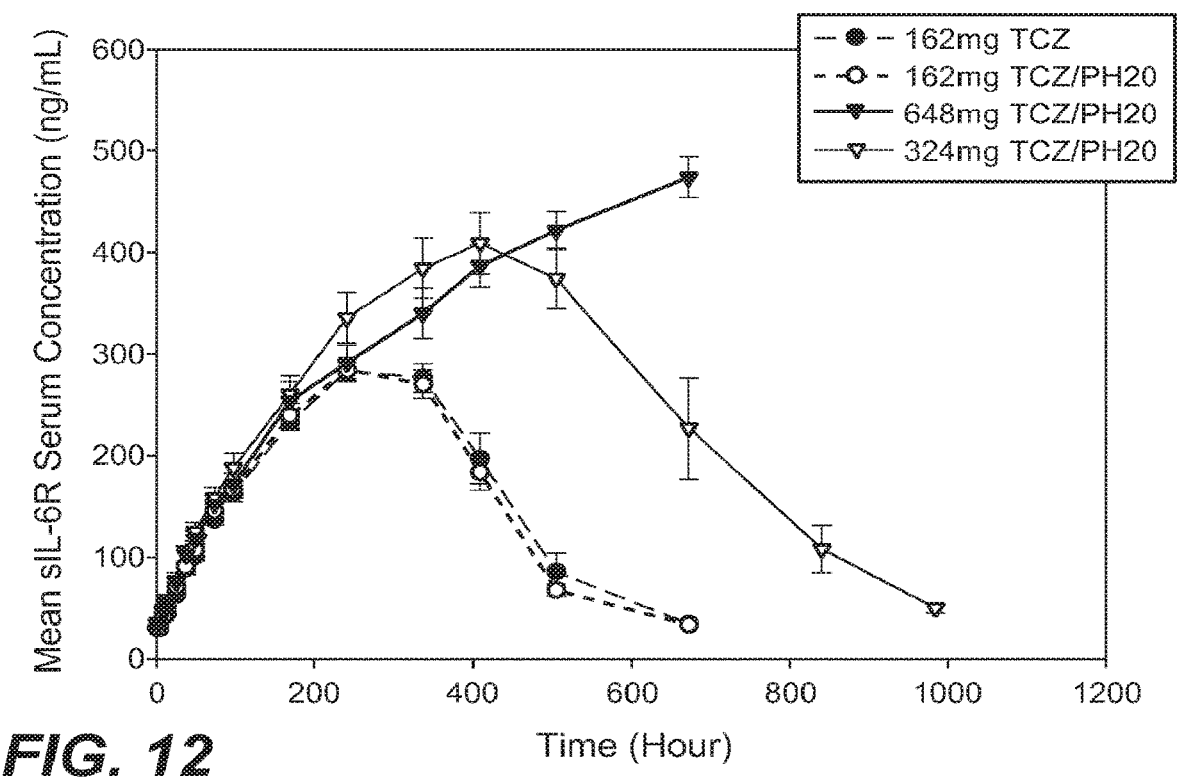

FIG. 12 depicts mean (±SEM) sIL-6R concentration-time plot by cohort. TCZ=tocilizumab; TCZ/PH20=tocilizumab co-formulated with rHuPH20.

Figure 13:
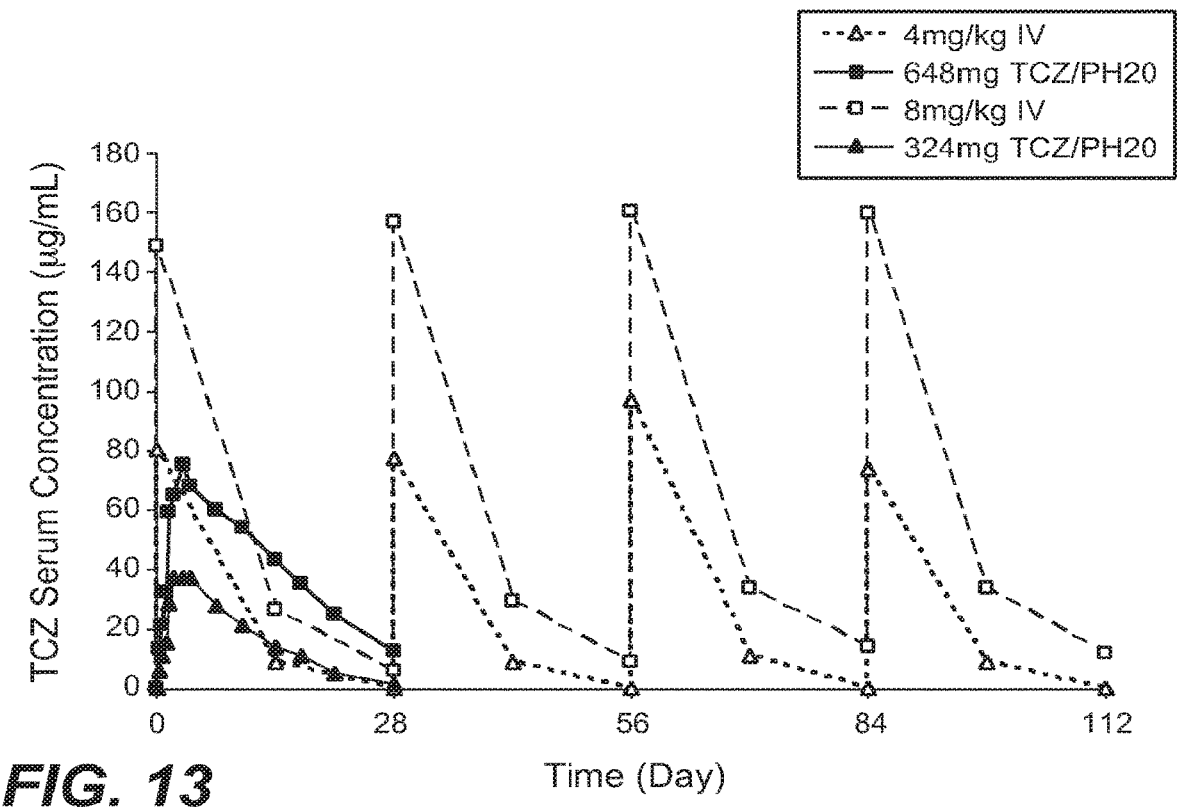

FIG. 13 compares IV PK profiles following 4 and 8 mg/kg every 4 Weeks with SC PK profiles following 324 mg TCZ/rHuPH20 and 648 mg TCZ/rHuPH20 Administration (The IV data for 4 and 8 mg/kg are from study LRO320). TCZ=tocilizumab; TCZ/PH20=tocilizumab co-formulated with rHuPH20.

Figure 14A:
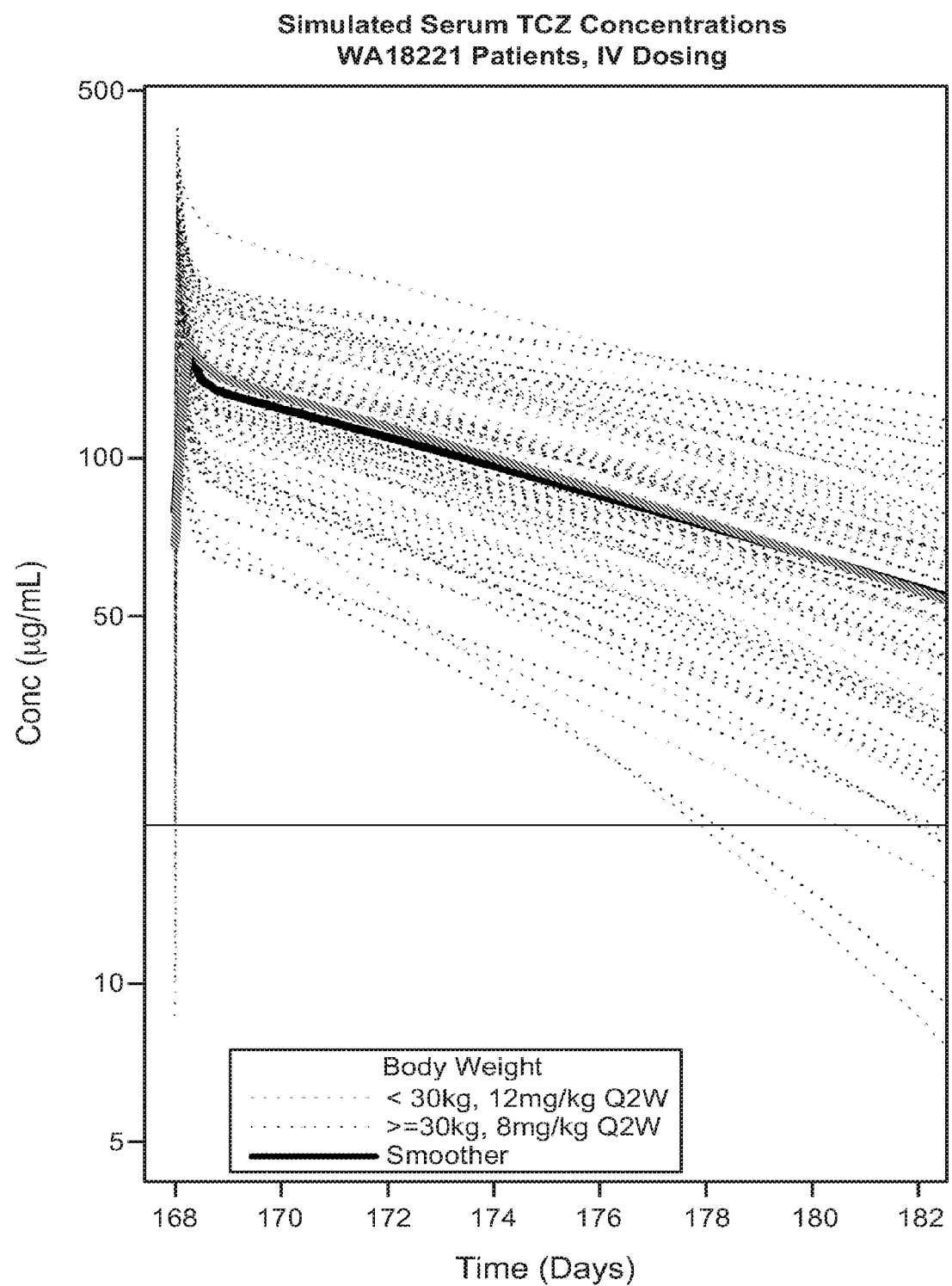
Figure 14B:
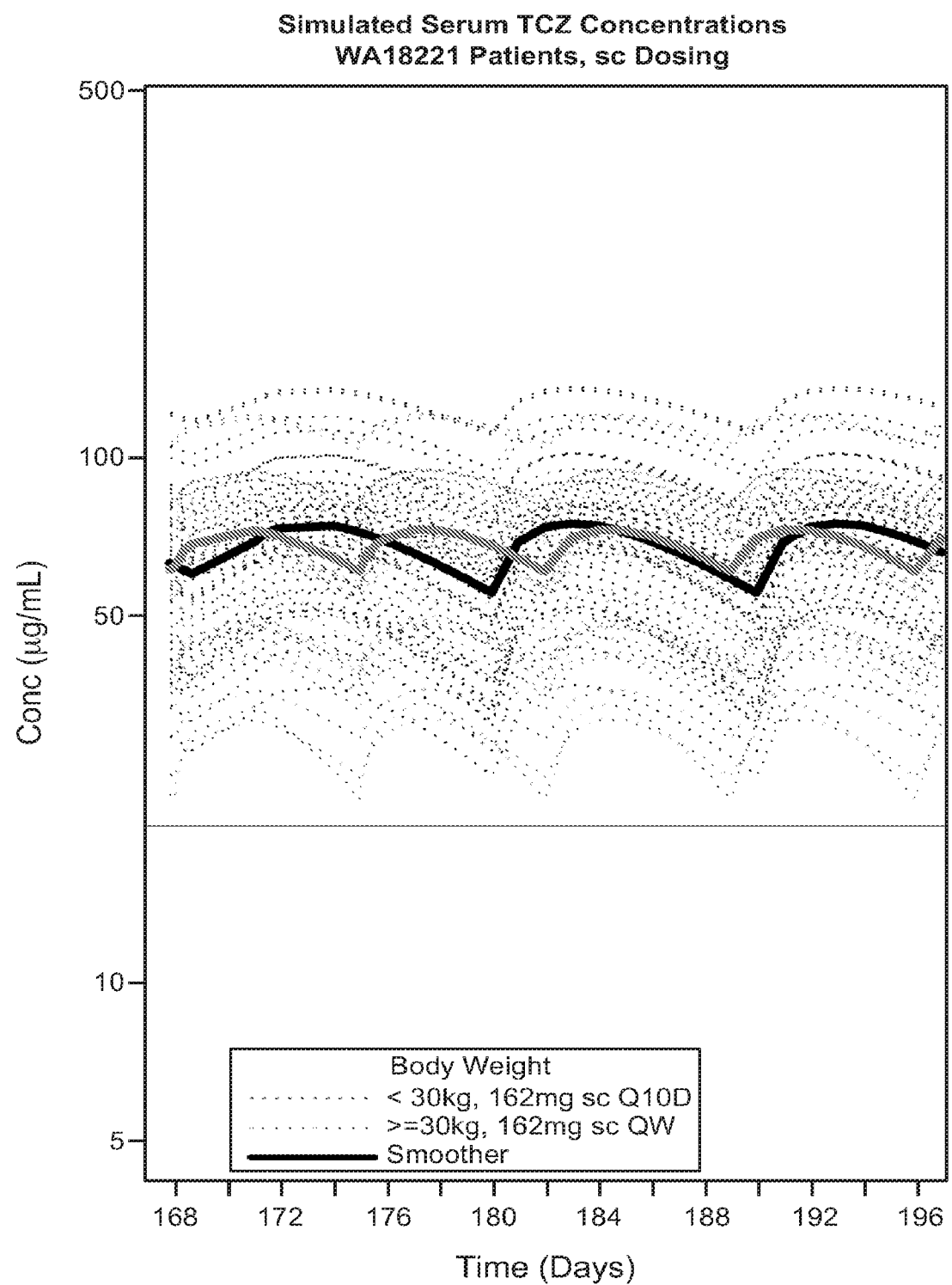

FIGS. 14A and 14B depict PK profiles following intravenous (IV) (simulated for WA18221 FIG. 14A) and subcutaneous (SC) administration (simulated for the patients from WA18221, FIG. 14B).

Figure 15:
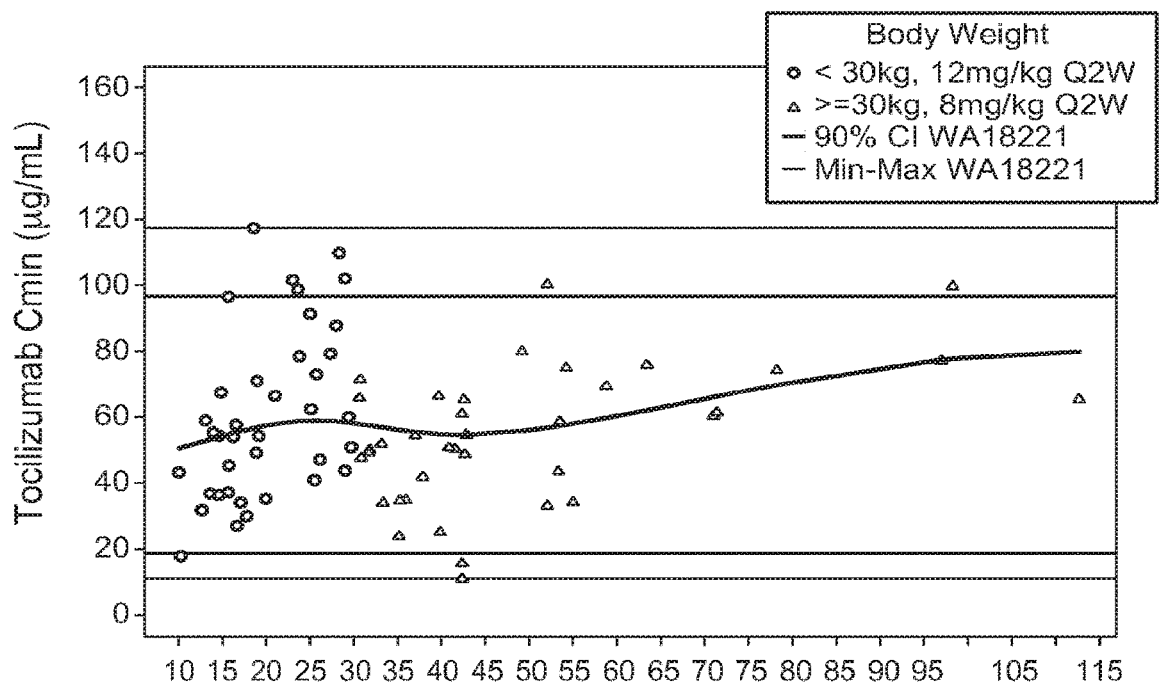

FIG. 15 model predicted Cmin for study WA18221 (12 mg/kg for body weight (BW)<30 kg and 8 mg/kg for BW≥30 kg).

Figure 16:
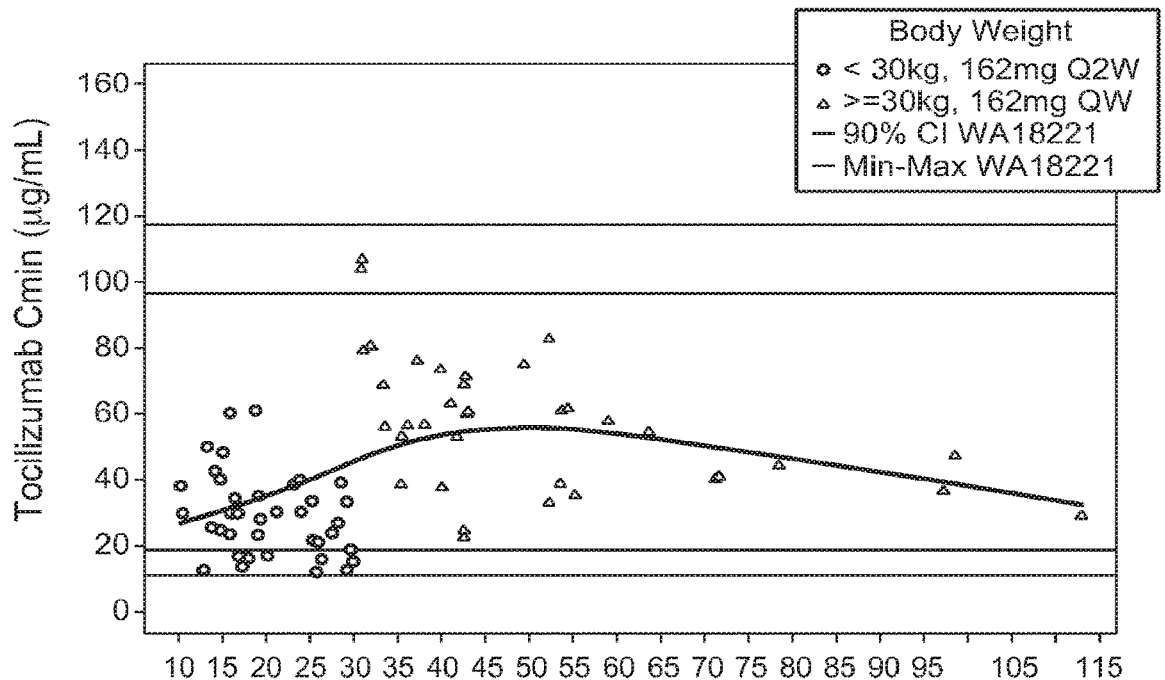

FIG. 16 model simulated TCZ Cmin for sJIA patients (162 mg Q2W for BW<30 kg and 162 mg QW for BW≥30 kg).

Figure 17:
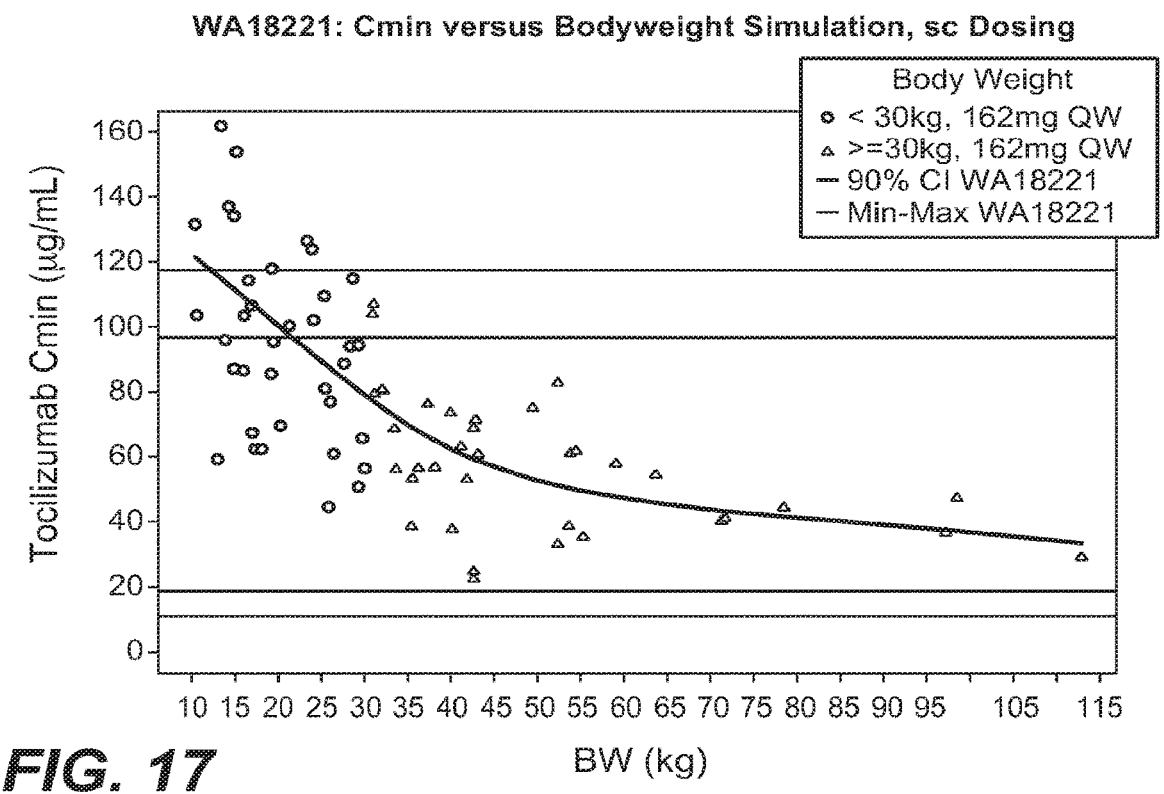

FIG. 17 model simulated TCZ Cmin for sJIA patients (162 mg QW for BW<30 kg and 162 mg QW for BW≥30 kg).

Figure 18:
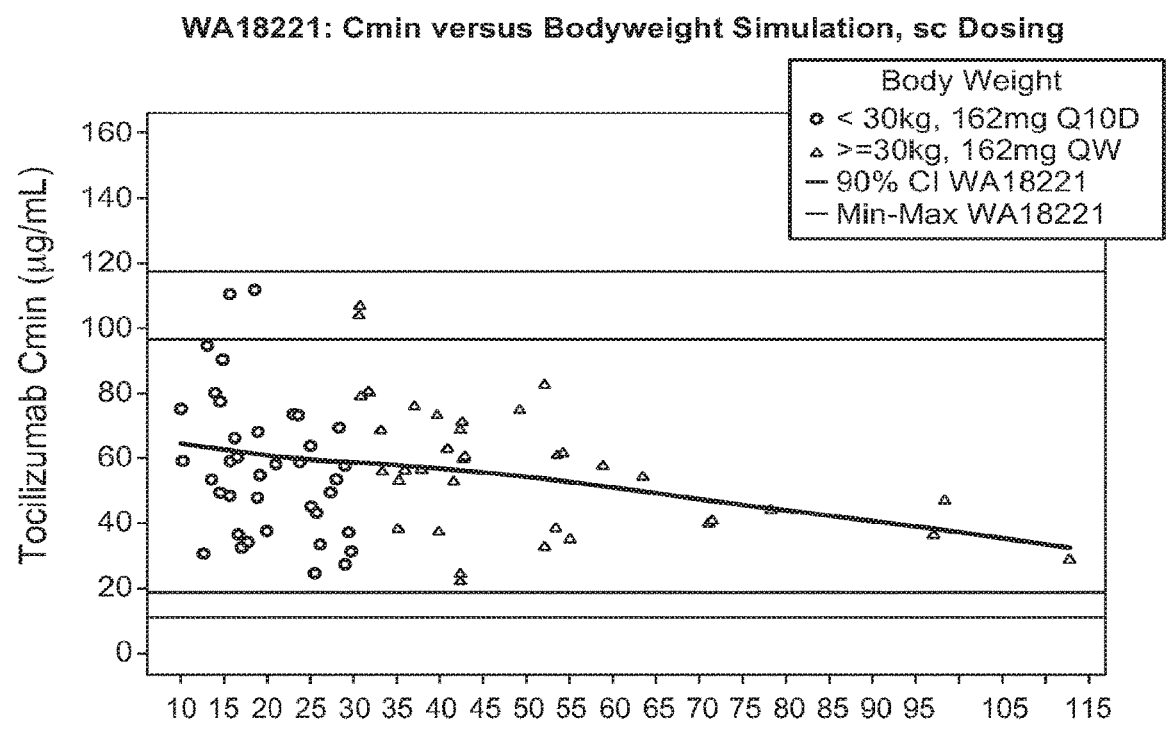

FIG. 18 model simulated TCZ Cmin for sJIA patients (162 mg Q10D for BW<30 kg and 162 QW for BW≥30 kg).

Figure 19A:
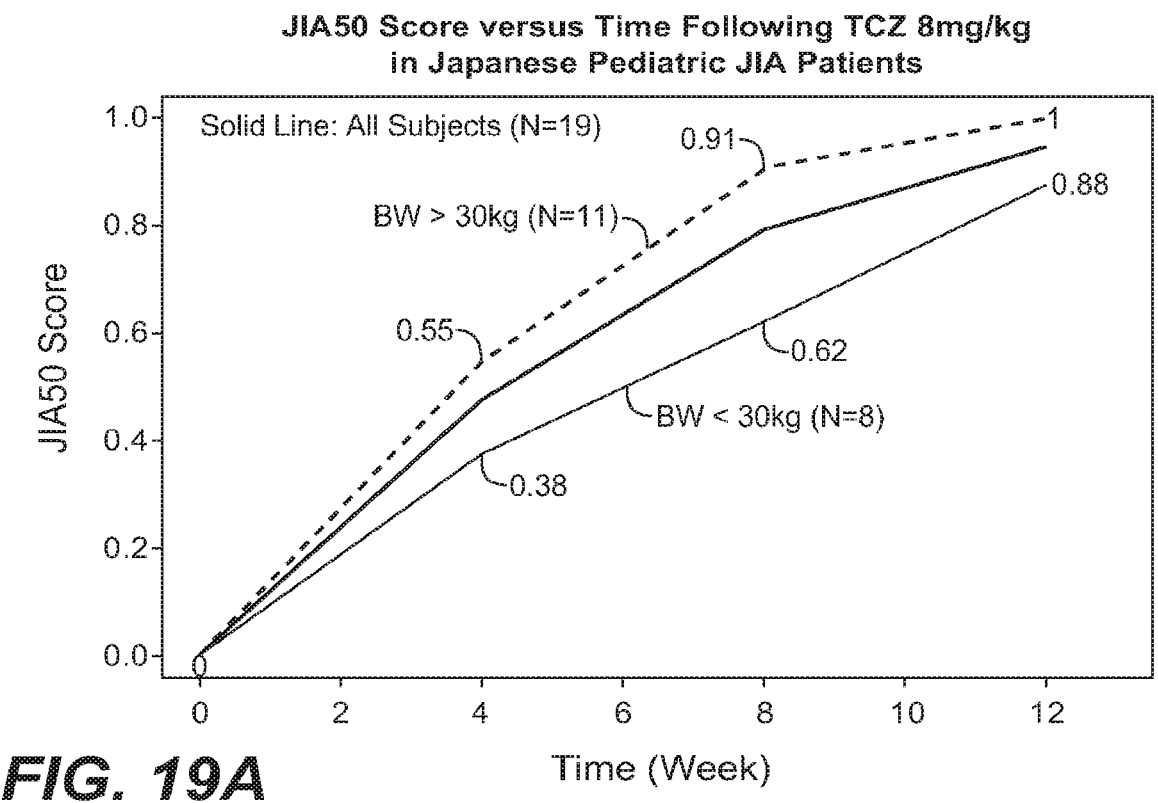
Figure 19B:
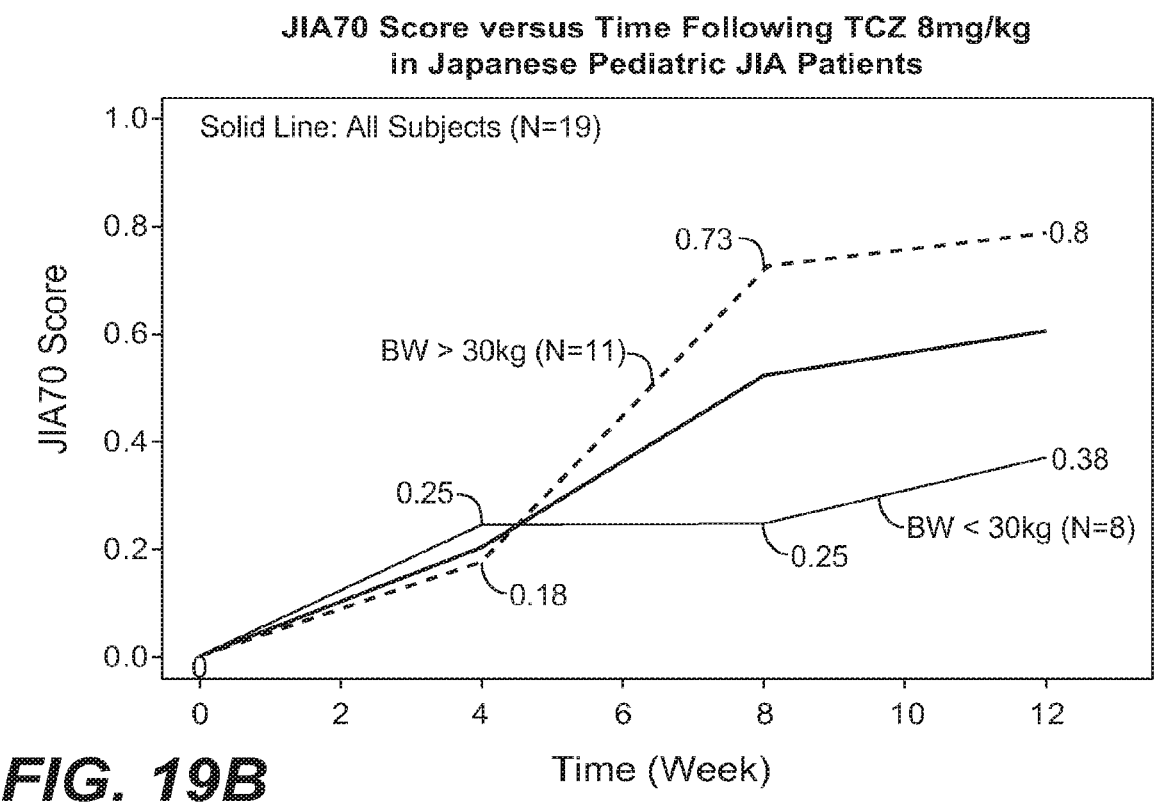

FIGS. 19A and 19B depict probability to reach pcJIA50 score (FIG. 19A) and pcJIA70 score (FIG. 19B) in study MRA318JP (8 mg/kg TCZ) in different body weight categories. Numbers on dotted lines indicate the probability to reach pcJIA50 or pcJIA70 score.

Figure 20A:
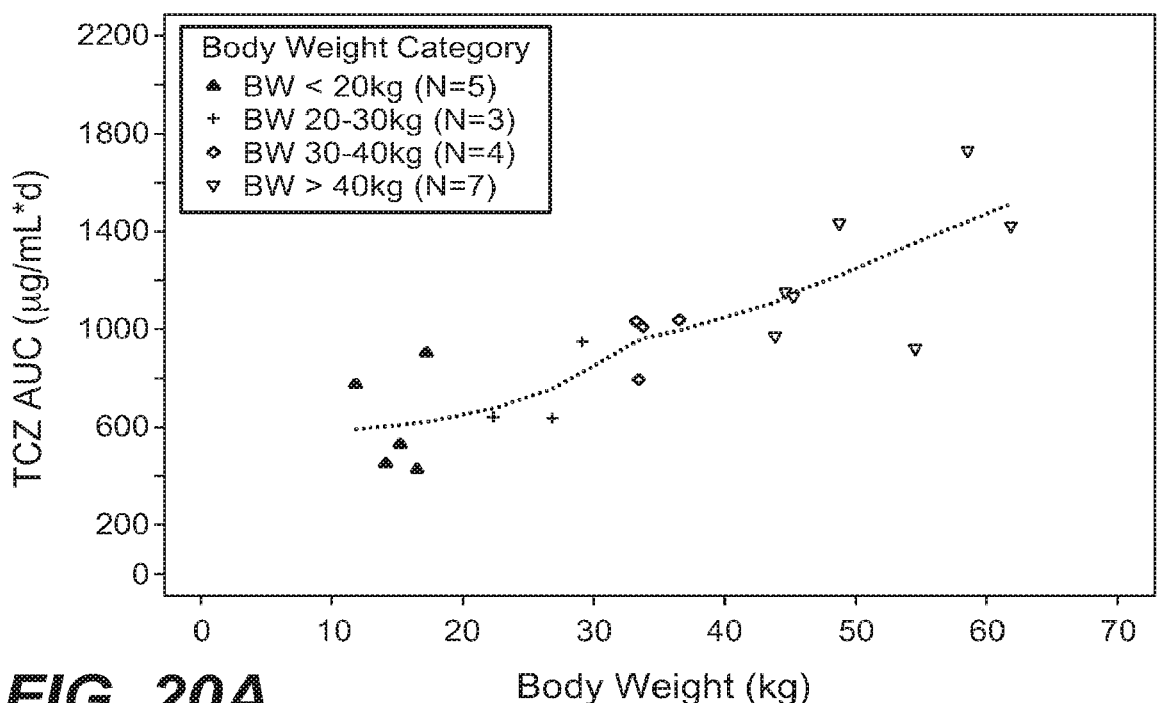
Figure 20B:
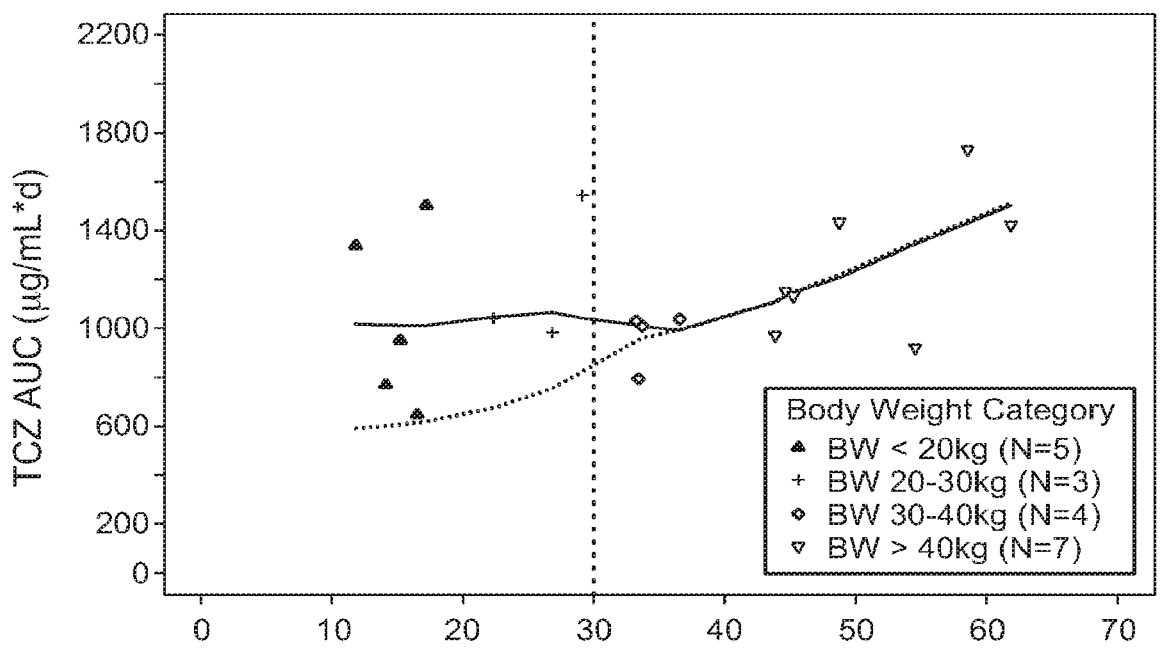

FIGS. 20A and 20B depict simulated area under curve (AUC) vs body weight (BW) in Japanese Pediatric pcJIA patients (MRA318JP) after 6 months. TCZ 8 mg/kg every 4 weeks in both body weight categories (n=19) (FIG. 20A); 10 mg/kg and 8 mg/kg every 4 weeks in children with body weight <30 kg and ≥30 kg (n=19) (FIG. 20B). The full line represents a smoothed spline through the data. The dotted line (FIG. 20B) is a smoothed spline indicating the reference trend in the data without any change in mg/kg dose in children with a body weight lower than 30 kg.

Figure 21A:
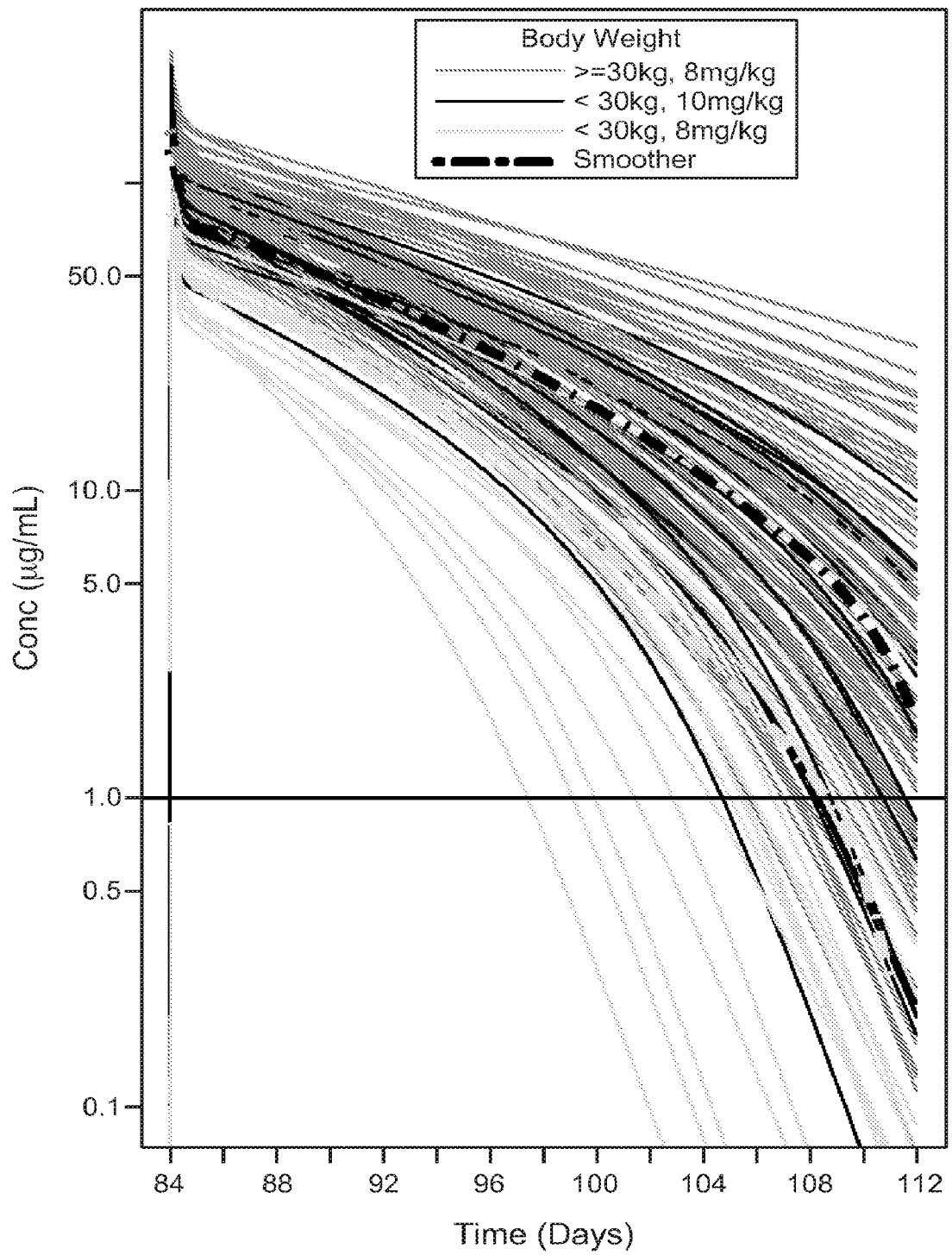
Figure 21B:
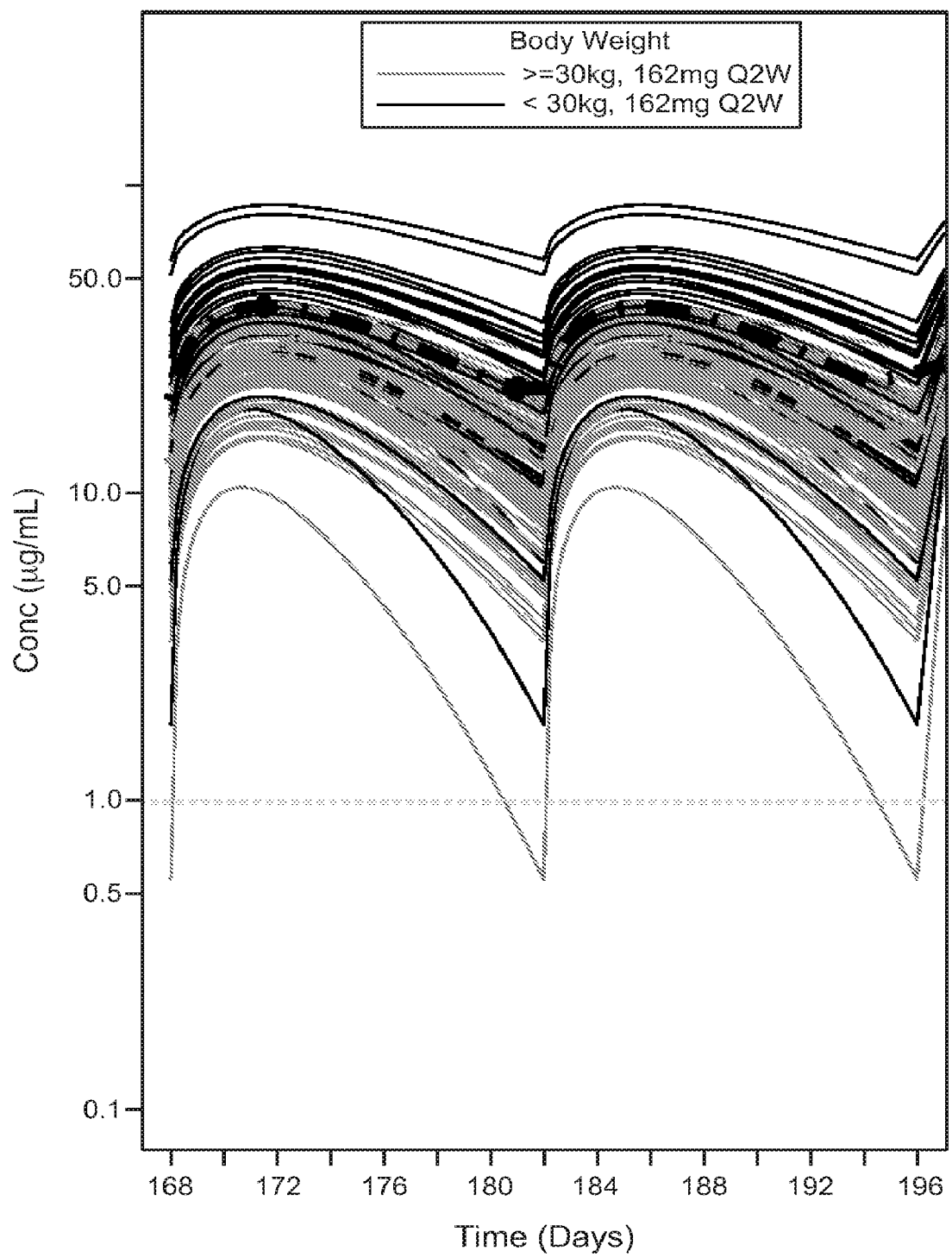

FIGS. 21A and 21B depict PK profiles following IV administration every 4 weeks (simulated for WA19977, FIG. 21A) and 162 mg SC administration every 2 weeks (simulated for patients from WA19977, FIG. 21B).

Figure 22:
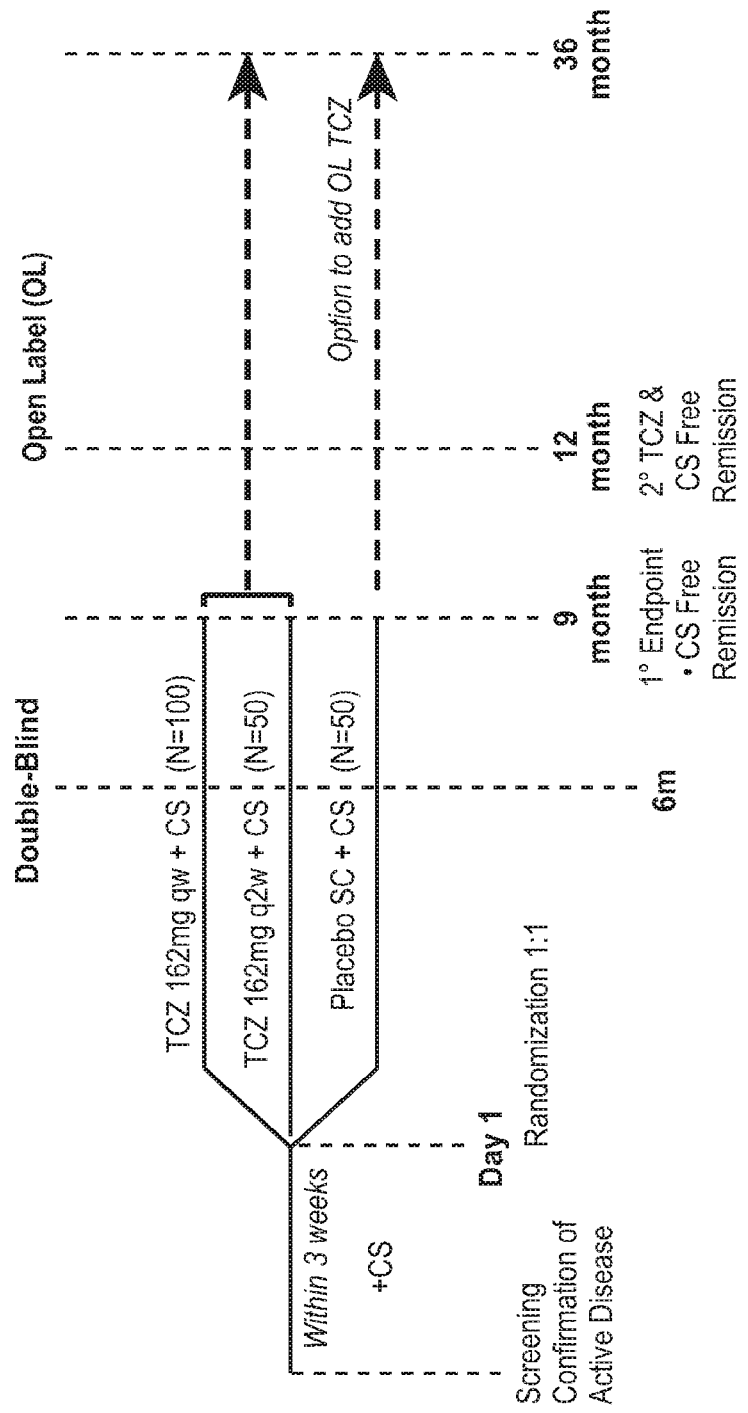

FIG. 22 is a schematic of subcutaneously administered anti-IL-6R antibody (TCZ) in giant cell arteritis (GCA).

FIGS. 23A-23D show concentration-time profiles for TCZ (FIG. 23A), sIL-6R/TCZ complex (FIG. 23B), CRP (FIG. 23C), and ESR (FIG. 23D) for two body weight groups through week 16 in WA18221 study FIGS. 24A-24D show concentration-time profiles for TCZ (FIG. 24A), sIL-6R (FIG. 24B), CRP (FIG. 24C) and ESR (FIG. 24D) for pcJIA patients from the MRA318JP study.

DETAILED DESCRIPTION OF THE PREFERRED EMBODIMENTS

I. Definitions

Some abbreviations used herein: adverse event (AE), auto-injector (AI), area under curve (AUC), body weight (BW), corticosteroids (CS), C-reactive protein (CRP), every 10 days (Q10D), every week (QW), every 2 weeks (Q2W), every 4 weeks (Q4W), giant cell arteritis (GCA), interleukin 6 (IL-6), interleukin 6 receptor (IL-6R), intravenous (IV), juvenile idiopathic arthritis (JIA), methotrexate (MTX), non-steroidal anti-inflammatory drugs (NSAIDs), pharmacodynamic (PD), pharmacokinetic (PK), polyarticular course juvenile idiopathic arthritis (pcJIA), pre-filled syringe (PFS), rheumatoid arthritis (RA), rheumatoid factor (RF), serious adverse event (SAE), soluble interleukin 6 receptor (sIL-6R), subcutaneous (SC), systemic juvenile idiopathic arthritis (sJIA), tocilizumab (TCZ), and water for injection (WFI).

Herein "human interleukin 6" (abbreviated as "IL-6") is a cytokine also known as B cell-stimulating factor 2 (BSF-2), or interferon beta-2 (IFNB2), hybridoma growth factor, and CTL differentiation factor. IL-6 was discovered as a differentiation factor contributing to activation of B cells (Hirano et al., *Nature* 324: 73-76 (1986)), and was later found to be a multifunction cytokine which influences the functioning of a variety of different cell types (Akira et al., *Adv. in Immunology* 54: 1-78 (1993)). Naturally occurring human IL-6 variants are known and included in this definition Human IL-6 amino acid sequence information has been disclosed, see for example, www.uniprot.org/uniprot/P05231.

For the purposes herein "human interleukin 6 receptor" (abbreviated as "IL-6R") refers to the receptor which binds IL-6, including both membrane-bound IL-6R (mIL-6R) and soluble IL-6R (sIL-6R). IL-6R can combine with interleukin 6 signal transducer glycoprotein 130 to form an active receptor complex. Alternatively spliced transcript variants encoding distinct isoforms of IL-6 have been reported and are included in this definition. The amino acid sequence structure of human IL-6R and its extracellular domain have been described; see, for example, Yamasaki et al., *Science,* 241: 825 (1988).

A "neutralizing" anti-IL-6R antibody herein is one which binds to IL-6R and is able to inhibit, to a measurable extent, the ability of IL-6 to bind to and/or active IL-6R. Toclizumab is an example of a neutralizing anti-IL-6R antibody.

"Tocilizumab" or "TCZ" is a recombinant humanized monoclonal antibody that binds to human interleukin-6 receptor (IL-6R). It is an IgG1κ (gamma 1, kappa) antibody with a two heavy chains and two light chains forming two antigen-binding sites. In a preferred embodiment, the light chain and heavy chain amino acid sequences of Tocilizumab comprise SEQ ID NOs. 1 and 2, respectively (see FIGS. 7A-B).

A "native sequence" protein herein refers to a protein comprising the amino acid sequence of a protein found in nature, including naturally occurring variants of the protein. The term as used herein includes the protein as isolated from a natural source thereof or as recombinantly produced.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

"Antibody fragments" herein comprise a portion of an intact antibody which retains the ability to bind antigen. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example. Specific examples of monoclonal antibodies herein include chimeric antibodies, humanized antibodies, and human antibodies, including antigen-binding fragments thereof.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992). Humanized antibodies herein specifically include "reshaped" IL-6R antibodies as described in U.S. Pat. No. 5,795,965, expressly incorporated herein by reference.

A "human antibody" herein is one comprising an amino acid sequence structure that corresponds with the amino acid sequence structure of an antibody obtainable from a human B-cell, and includes antigen-binding fragments of human antibodies. Such antibodies can be identified or made by a variety of techniques, including, but not limited to: production by transgenic animals (e.g., mice) that are capable, upon immunization, of producing human antibodies in the absence of endogenous immunoglobulin production (see, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and U.S. Pat. Nos. 5,591,669, 5,589,369 and 5,545,807)); selection from phage display libraries expressing human antibodies or human antibody fragments (see, for example, McCafferty et al., *Nature* 348:552-553 (1990); Johnson et al., *Current Opinion in Structural Biology* 3:564-571 (1993); Clackson et al., *Nature,* 352:624-628 (1991); Marks et al., *J. Mol. Biol.* 222:581-597 (1991); Griffith et al., *EVIBO J.* 12:725-734 (1993); U.S. Pat. Nos. 5,565,332 and 5,573,905); generation via in vitro activated B cells (see U.S. Pat. Nos. 5,567,610 and 5,229,275); and isolation from human antibody producing hybridomas.

A "multispecific antibody" herein is an antibody having binding specificities for at least two different epitopes. Exemplary multispecific antibodies may bind to two different epitopes of IL-6R. Alternatively, an anti-IL-6R binding arm may be combined with an arm that binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the receptor. Multispecific antibodies can be prepared as full-length antibodies or antibody fragments (e.g. F(ab')$_2$ bispecific antibodies). Engineered antibodies with three or more (preferably four)

functional antigen binding sites are also contemplated (see, e.g., US Appln No. US 2002/0004587 A1, Miller et al.).

Antibodies herein include "amino acid sequence variants" with altered antigen-binding or biological activity. Examples of such amino acid alterations include antibodies with enhanced affinity for antigen (e.g. "affinity matured" antibodies), and antibodies with altered Fc region, if present, e.g. with altered (increased or diminished) antibody dependent cellular cytotoxicity (ADCC) and/or complement dependent cytotoxicity (CDC) (see, for example, WO 00/42072, Presta, L. and WO 99/51642, Iduosogie et al.); and/or increased or diminished serum half-life (see, for example, WO00/42072, Presta, L.).

An "affinity matured variant" has one or more substituted hypervariable region residues of a parent antibody (e.g. of a parent chimeric, humanized, or human antibody). Generally, the resulting variant(s) selected for further development will have improved antigen-binding affinity relative to the parent antibody from which they are generated. A convenient way for generating such substitutional variants involves "affinity maturation" using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity). In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human IL-2R. Such contact residues and neighboring residues are candidates for substitution according to the techniques elaborated herein. Once such variants are generated, the panel of variants is subjected to screening and antibodies with improved affinity may be selected for further development.

The antibody herein may be conjugated with a "heterologous molecule" for example to increase half-life or stability or otherwise improve the antibody. For example, the antibody may be linked to one of a variety of non-proteinaceous polymers, e.g., polyethylene glycol (PEG), polypropylene glycol, polyoxyalkylenes, or copolymers of polyethylene glycol and polypropylene glycol. Antibody fragments, such as Fab', linked to one or more PEG molecules are an exemplary embodiment of the invention.

The antibody herein may be a "glycosylation variant" such that any carbohydrate attached to the Fc region, if present, is altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) describing antibodies with modified glycosylation.

The term "hypervariable region" when used herein refers to the amino acid residues of an antibody that are responsible for antigen binding. The hypervariable region comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework" or "FR" residues are those variable domain residues other than the hypervariable region residues as herein defined. The hypervariable regions of Tocilizumab comprise:

```
                                              (SEQ ID NO: 3)
L1-Arg Ala Ser Gln Asp Ile Ser Ser Tyr Leu Asn;

(SEQ ID NO: 4)
L2-Tyr Thr Ser Arg Leu His Ser;

(SEQ ID NO: 5)
L3-Gln Gln Gly Asn Thr Leu Pro Tyr Thr;

(SEQ ID NO: 6)
H1-Ser Asp His Ala Trp Ser;

(SEQ ID NO: 7)
H2-Tyr Ile Ser Tyr Ser Gly Ile Thr Thr Tyr Asn Pro

Ser Leu Lys Ser;
and (SEQ ID NO: 8)
H3-Ser Leu Ala Arg Thr Thr Ala Met Asp Tyr.
```

In one embodiment herein, the IL-6R antibody comprises the hypervariable regions of Tocilizumab.

A "full length antibody" is one which comprises an antigen-binding variable region as well as a light chain constant domain (CL) and heavy chain constant domains, CH1, CH2 and CH3. The constant domains may be native sequence constant domains (e.g. human native sequence constant domains) or amino acid sequence variants thereof. Preferably, the full length antibody has one or more effector functions. Tocilizumab is an example of a full-length antibody.

A "naked antibody" is an antibody (as herein defined) that is not conjugated to a heterologous molecule, such as a cytotoxic moiety, polymer, or radiolabel.

Antibody "effector functions" refer to those biological activities attributable to the Fc region (a native sequence Fc region or amino acid sequence variant Fc region) of an antibody. Examples of antibody effector functions include C1q binding, complement dependent cytotoxicity (CDC), Fc receptor binding, antibody-dependent cell-mediated cytotoxicity (ADCC), etc.

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

The term "recombinant antibody", as used herein, refers to an antibody (e.g. a chimeric, humanized, or human antibody or antigen-binding fragment thereof) that is expressed by a recombinant host cell comprising nucleic acid encoding the antibody. Examples of "host cells" for producing recombinant antibodies include: (1) mammalian cells, for example, Chinese Hamster Ovary (CHO), COS, myeloma cells (including YO and NSO cells), baby hamster kidney (BHK), Hela and Vero cells; (2) insect cells, for example, sf9, sf21 and Tn5; (3) plant cells, for example plants belonging to the genus *Nicotiana* (e.g. *Nicotiana tabacum*); (4) yeast cells, for example, those belonging to the genus *Saccharomyces* (e.g. *Saccharomyces cerevisiae*) or the genus *Aspergillus* (e.g. *Aspergillus niger*); (5) bacterial cells, for example *Escherichia. coli* cells or *Bacillus subtilis* cells, etc.

As used herein, "specifically binding" or "binds specifically to" refers to an antibody selectively or preferentially binding to IL-6R antigen. Preferably the binding affinity for antigen is of Kd value of $10^{-9}$ mol/l or lower (e.g. $10^{-10}$ mol/l), preferably with a Kd value of $10^{10}$ mol/l or lower (e.g. $10^{-12}$ mol/l). The binding affinity is determined with a standard binding assay, such as surface plasmon resonance technique (BIACORE®).

For the purposes herein, the term "IL-6-mediated disorder" refers to a disease or disorder in which activation of IL-6R by IL-6 results in the disorder and/or treatment with an anti-IL-6R antibody can be used to treat the disease or disorder. Examples of such disorders include: autoimmune diseases, osteoporosis, neoplasia, aging, rheumatoid arthritis (RA), juvenile idiopathic arthritis (JIA) (including systemic JIA and polyarticular course JIA), psoriatic arthritis, Castleman's disease, Crohn's disease, multiple myeloma, polymyalgia rheumatica, glomerulonephritis, plasmacytoma or plasmacytosis, myeloma (including multiple myeloma), hyperimmunoglobulinemia, anemia, nephritis (such as mesangium proliferative nephritis), cachexia (including cancerous cachexia), tumors, T cell mediated disease (e.g. uveitis, chronic thyroiditis, delayed hypersensitivity, contact dermatitis, or atopic dermatitis), lupus (including lupus nephritis and systemic lupus erythmatosus), inflammatory bowel disease (including Crohn's disease and ulcerative colitis), pancreatitis, psoriasis, osteoarthritis, adult-onset Still's disease, mesothelioma, vasculitis, islet transplantation (e.g. pancreatic islet transplantation), myocardial infarction (heart failure, ischemia-induced severe arrhythmia), heart transplantation, prostate cancer, choroidal neovascularization (e.g. age-related macular degeneration, idiopathic choroidal neovascularization, cyopic choroidal neovascularization, idiopathic choroidal neovascularization), muscle atrophy, chronic rejection, ocular inflammatory disease (e.g. panuveitis, anterior aveitis, intermediate uveitis, scleritis, keratitis, orbital inflammation, optic neuritis, dry eye, diabetic retinopathy, proliferative vitreoretinopathy, postoperative inflammation), graft versus host disease (GVHD), fibrotic disorders (such as systemic sclerosis), giant cell arteritis (GCA), and Takayasu's arteritis (TA), arteritis *nodosa*, ankylosing spondylitis, etc.

In one embodiment, the IL-6-mediated disorder is rheumatoid arthritis.

In one embodiment, the IL-6 mediated disorder is juvenile idiopathic arthritis (JIA). In one embodiment, the IL-6 mediated disorder is systemic JIA (sJIA).

In one embodiment, the IL-6 mediated disorder is polyarticular course JIA (pcJIA).

In one embodiment, the IL-6 mediated disorder is systemic sclerosis.

In one embodiment, the IL-6 mediated disorder is giant cell arteritis (GCA).

In one embodiment, the IL-6 mediated disorder is psoriatic arthritis.

In one embodiment, the IL-6 mediated disorder is uveitis.

As used herein, "rheumatoid arthritis" (abbreviated as "RA") refers to is a chronic, systemic inflammatory disorder that may affect many tissues and organs, but principally attacks synovial joints. RA diagnosed according to the RA must be diagnosed according to the 1987 or 2000 revised American College of Rheumatology (ACR; formerly American Rheumatism Association) criteria for the classification of rheumatoid arthritis, or any similar criteria. Physiological indicators of RA include, symmetric joint swelling which is characteristic though not invariable in rheumatoid arthritis. Fusiform swelling of the proximal interphalangeal (PIP) joints of the hands as well as metacarpophalangeal (MCP), wrists, elbows, knees, ankles and metatarsophalangeal (MTP) joints are commonly affected and swelling is easily detected. Pain on passive motion is the most sensitive test for joint inflammation, and inflammation and structural deformity often limits the range of motion for the affected joint. Typical visible changes include ulnar deviation of the fingers at the MCP joints, hyperextension or hyperflexion of the MCP and PIP joints, flexion contractures of the elbows, and subluxation of the carpal bones and toes.

A patient with "active rheumatoid arthritis" means a patient with active and not latent symptoms of rheumatoid arthritis. In one embodiment, such patient has moderate-to-severe active RA of ≥6 months disease duration at time of baseline visit. In one embodiment, such patients will have: (1) swollen joint count (SJC)≥4 (66 joint count), (2) tender joint count (TJC)≥4 (68 joint count), and/or C-reactive protein (CRP)≥upper limit of normal (ULN) at screening visit.

Examples of "disease-modifying anti-rheumatic drugs" or "DMARDs" include hydroxycloroquine, sulfasalazine, methotrexate, leflunomide, azathioprine, D-penicillamine, gold salts (oral), gold salts (intramuscular), minocycline, cyclosporine including cyclosporine A and topical cyclosporine, staphylococcal protein A, and TNF-inhibitors (see below), including salts, variants, and derivatives thereof, etc. Exemplary DMARDs herein are non-biological DMARDs, including, in particular, azathioprine, chloroquine, hydroxychloroquine, leflunomide, methotrexate and sulfasalazine, with methotrexate being the DMARD according to one embodiment of the invention.

For the purposes herein, "tumor necrosis factor" (abbreviated "TNF") refers to a human TNF-alpha molecule comprising the amino acid sequence as described in Pennica et al., *Nature,* 312:721 (1984) or Aggarwal et al., JBC, 260: 2345 (1985).

A "TNF-inhibitor" herein is an agent that inhibits, to some extent, a biological function of TNF-alpha, generally through binding to TNF-alpha and neutralizing its activity. Examples of TNF inhibitors specifically contemplated herein are etanercept (ENBREL®), infliximab (REMICADE®), and adalimumab (HUMIRA®), certolizumab pegol (CIMZIA®), and golimumab (SIMPONI®).

The subject who is a "DMARD inadequate responder" is one who has experienced an inadequate response to previous or current treatment with one or more DMARDs (including one or more TNF inhibitors) because of toxicity or inadequate efficacy.

The subject who is a "TNF inhibitor inadequate responder" has experienced an inadequate response to previous or current treatment with one or more TNF inhibitors because of toxicity or inadequate efficacy. In one embodiment, such patient has received, for example, etanercept for ≥3 months at 25 mg twice a week or at least 4 infusions of infliximab at ≥3 mg/kg but had an inadequate response thereto.

A "methotrexate inadequate responder" is a patient who has experienced an inadequate response to previous or current treatment with methotrexate because of toxicity or inadequate efficacy. In one embodiment, the patient has been on methotrexate (10-25 mg/week) for at least 12 weeks and still has active disease.

A "fixed dose" herein refers to a dosage of a drug, such as an anti-IL-6R antibody which is administered without regard to the patient's weight or body surface area (BSA), i.e. it is not administered as either a mg/kg or mg/m$^2$ dose.

"Treatment" of a subject herein refers to both therapeutic treatment and prophylactic or preventative measures.

The expression "effective amount" refers to an amount of the antibody that is effective for treating the IL-6 disorder. Where the disorder is RA, such effective amount can result in any one or more of reducing the signs or symptoms of RA (e.g. achieving ACR20, ACR50, or ACR70 response at week 24 and/or week 48), reducing disease activity (e.g. Disease Activity Score, DAS20), ACR-hybrid, slowing the progression of structural joint damage, improving physical function, etc. In one embodiment, such clinical response is comparable to that achieved with intravenously administered anti-IL-6R antibody.

The expression "inhibiting progression of structural joint damage" in a RA patient refers to preventing or slowing structural joint damage caused by RA, for example based on eroded joint count and/or joint damage score. Methods for measuring progression of structural joint damage are known to the skilled person, and include, without limitation Genant-modified Total Sharp Score (TSS), erosion score (ES), and/or joint space narrowing (JSN) score.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine antagonists such as cytokine antibodies or cytokine receptor antibodies including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists; anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodornase; RNA or DNA from the host; FK506; RS-61443; chlorambucil; deoxyspergualin; rapamycin; T-cell receptor (Cohen et al., U.S. Pat. No. 5,114,721); T-cell receptor fragments (Officer et al., Science, 251: 430-432 (1991); WO 90/11294; Ianeway, Nature, 341: 482 (1989); and WO 91/01133); BAFF antagonists such as BAFF antibodies and BR3 antibodies and zTNF4 antagonists (for review, see Mackay and Mackay, Trends Immunol., 23:113-5 (2002)); biologic agents that interfere with T cell helper signals, such as anti-CD40 receptor or anti-CD40 ligand (CD154), including blocking antibodies to CD40-CD40 ligand (e.g., Durie et al., Science, 261: 1328-30 (1993); Mohan et al., J. Immunol., 154: 1470-80 (1995)) and CTLA4-Ig (Finck et al., Science, 265: 1225-7 (1994)); and T-cell receptor antibodies (EP 340,109) such as T10B9. Some immunosuppressive agents herein are also DMARDs, such as methotrexate. Examples of immunosuppressive agents herein include cyclophosphamide, chlorambucil, azathioprine, leflunomide, MMF, or methotrexate.

The "CD20" antigen, or "CD20," is an about 35-kDa, non-glycosylated phosphoprotein found on the surface of greater than 90% of B cells from peripheral blood or lymphoid organs. CD20 is present on both normal B cells as well as malignant B cells, but is not expressed on stem cells. Other names for CD20 in the literature include "B-lymphocyte-restricted antigen" and "Bp35". The CD20 antigen is described in Clark et al., Proc. Natl. Acad. Sci. (USA) 82:1766 (1985), for example.

Examples of CD20 antibodies include: "C2B8," which is now called "rituximab" ("RITUXAN®/MABTHERA®") (U.S. Pat. No. 5,736,137); the yttrium-[90]-labelled 2B8 murine antibody designated "Y2B8" or "Ibritumomab Tiuxetan" (ZEVALIN®) commercially available from Biogen Idec, Inc. (e.g., U.S. Pat. No. 5,736,137; 2B8 deposited with ATCC under accession no. HB11388 on Jun. 22, 1993); murine IgG2a "B1," also called "Tositumomab," optionally labelled with $^{131}$I to generate the "131I-B1" or "iodine 1131 tositumomab" antibody (BEXXAR™) commercially available from Corixa (see, also, e.g., U.S. Pat. No. 5,595,721); murine monoclonal antibody "1F5" (e.g., Press et al. Blood 69(2):584-591 (1987) and variants thereof including "framework patched" or humanized 1F5 (e.g., WO 2003/002607, Leung, S.; ATCC deposit HB-96450); murine 2H7 and chimeric 2H7 antibody (e.g., U.S. Pat. No. 5,677,180); a humanized 2H7 (e.g., WO 2004/056312 (Lowman et al.) and as set forth below); HUMAX-CD20™ fully human, high-affinity antibody targeted at the CD20 molecule in the cell membrane of B-cells (Genmab, Denmark; see, for example, Glennie and van de Winkel, Drug Discovery Today 8: 503-510 (2003) and Cragg et al., Blood 101: 1045-1052 (2003)); the human monoclonal antibodies set forth in WO 2004/035607 and WO 2005/103081 (Teeling et al., GenMab/Medarex); the antibodies having complex N-glycoside-linked sugar chains bound to the Fc region described in US 2004/0093621 (Shitara et al.); monoclonal antibodies and antigen-binding fragments binding to CD20 (e.g., WO 2005/000901, Tedder et al.) such as HB20-3, HB20-4, HB20-25, and MB20-11; single-chain proteins binding to CD20 (e.g., US 2005/0186216 (Ledbetter and Hayden-Ledbetter); US 2005/0202534 (Hayden-Ledbetter and Ledbetter); US 2005/0202028 (Hayden-Ledbetter and Ledbetter); US 2005/0202023 (Hayden-Ledbetter and Ledbetter, Trubion Pharm Inc.); CD20-binding molecules such as the AME series of antibodies, e.g., AME-33™ antibodies as set forth, for example, in WO 2004/103404 and US 2005/0025764 (Watkins et al., Applied Molecular Evolution, Inc.) and the CD20 antibodies with Fc mutations as set forth, for example, in WO 2005/070963 (Allan et al., Applied Molecular Evolution, Inc.); CD20-binding molecules such as those described in WO 2005/016969 and US 2005/0069545 (Carr et al.); bispecific antibodies as set forth, for example, in WO 2005/014618 (Chang et al.); humanized LL2 monoclonal antibodies as described, for example, in US 2005/0106108 (Leung and Hansen; Immunomedics); chimeric or humanized B-Ly1 antibodies to CD20 as described, for example, in WO2005/044859 and US 2005/0123546 (Umana et al.; GlycArt Biotechnology AG); A20 antibody or variants thereof such as chimeric or humanized A20 antibody (cA20, hA20, respectively) and IMMUN-106 (e.g., US 2003/0219433, Immunomedics); and monoclonal antibodies L27, G28-2, 93-1B3, B-C1 or NU-B2 available from the International Leukocyte Typing Workshop (e.g., Valentine et al., In: Leukocyte Typing III (McMichael, Ed., p. 440, Oxford University Press (1987)). The preferred CD20 antibodies herein are chimeric, humanized, or human CD20 antibodies, more preferably rituximab, a humanized 2H7, chimeric or humanized A20 antibody (Immunomedics), HUMAX-CD20™ human CD20 antibody (Genmab), and immunoglobulins/proteins binding to CD20 (Trubion Pharm Inc.).

The terms "rituximab" or "RITUXAN®" herein refer to the genetically engineered chimeric murine/human monoclonal antibody directed against the CD20 antigen and designated "C2B8" in US Patent No. U.S. Pat. No. 7,381,560 (Anderson et. al.), including fragments thereof which retain the ability to bind CD20.

Examples of "non-steroidal anti-inflammatory drugs" or "NSAIDs" include aspirin, acetylsalicylic acid, ibuprofen, flurbiprofen, naproxen, indomethacin, sulindac, tolmetin, phenylbutazone, diclofenac, ketoprofen, benorylate, mefenamic acid, methotrexate, fenbufen, azapropazone; COX-2 inhibitors such as celecoxib (CELEBREX®; 4-(5-(4-methylphenyl)-3-(trifluoromethyl)-1H-pyrazol-1-yl) benzenesulfonamide, valdecoxib (BEXTRA®), meloxicam (MOBIC®), GR 253035 (Glaxo Wellcome); and MK966 (Merck Sharp & Dohme), including salts and derivatives thereof, etc. Preferably, they are aspirin, naproxen, ibuprofen, indomethacin, or tolmetin.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone, such as SOLU-MEDROL® methylprednisolone sodium succinate), dexamethasone or dexamethasone triamcinolone, hydrocortisone, and betamethasone. The preferred corticosteroids herein are prednisone, methylprednisolone, hydrocortisone, or dexamethasone.

A "medicament" is an active drug to treat the joint damage or its symptoms or side effects.

The term "pharmaceutical formulation" refers to a preparation which is in such form as to permit the biological activity of the active ingredient or ingredients to be effective, and which contains no additional components which are unacceptably toxic to a subject to which the formulation would be administered. Such formulations are sterile.

A "sterile" formulation is aseptic or free from all living microorganisms and their spores.

A "stable" formulation is one in which all the protein therein essentially retain their physical stability and/or chemical stability and/or biological activity upon storage at the intended storage temperature, e.g. 2-8° C. Preferably, the formulation essentially retains its physical and chemical stability, as well as its biological activity upon storage. The storage period is generally selected based on the intended shelf-life of the formulation. Furthermore, the formulation is preferably stable following freezing (to, e.g., −20° C.) and thawing of the formulation, for example following 1 or more cycles of freezing and thawing. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; SDS-PAGE analysis to compare reduced and intact antibody; evaluating biological activity or antigen binding function of the antibody; etc.

A "stabilizer" herein is an excipient, or mixture of two or more excipients, which stabilizes a pharmaceutical formulation. For example, the stabilizer can prevent instability due to freezing-thawing or other thermal-induced destabilization of the formulation. Exemplary excipients herein include surfactants, and amino acids, such as arginine or methionine (including derivatives thereof).

The term "surfactant" as used herein denotes a pharmaceutically acceptable surface-active agent. In the formulation of the invention, the amount of surfactant is described a percentage expressed in weight/volume. The most commonly used weight/volume unit is mg/mL. Suitable examples of pharmaceutically acceptable surfactants include polyoxyethylen-sorbitan fatty acid esters, polyethylene-polypropylene glycols, polyoxyethylene-stearates, polyoxyethylene alkyl ethers, e.g. polyoxyethylene monolauryl ether, alkylphenylpolyoxy-ethylene ethers (Triton-X), polyoxyethylene-polyoxypropylene copolymer (Poloxamer, Pluronic), and sodium dodecyl sulphate (SDS). Most suitable polyoxyethylenesorbitan-fatty acid esters are polysorbate 20 (sold under the trademark TWEEN 20®) and polysorbate 80 (sold under the trademark TWEEN 80®). Most suitable polyethylene-polypropylene copolymers are those sold under the names PLURONIC® F68 or POLOXAMER 188®. Preferred polyoxyethylene-stearates are those sold under the trademark MYRJ™. Most suitable polyoxyethylene alkyl ethers are those sold under the trademark BRIJ™. Most suitable alkylphenolpoly-oxyethylene ethers are sold under the trade name TRITON-X®.

The term "buffer" as used herein denotes a pharmaceutically acceptable buffer which resists changes in pH by the action of its acid/base conjugate components. Optionally, the pH of the formulation is in the range from 5 to 7, e.g. from 5.5 to 6.5, most preferably about pH 6, and the buffer employed achieves such desired pH for the formulation. Suitable pharmaceutically acceptable buffers according to the invention comprise but are not limited to histidine-buffers, citrate-buffers, gluconate-buffers, succinate-buffers, acetate-buffers glycylglycine and other organic acid buffers, and phosphate-buffers. Preferred buffers comprise L-histidine or mixtures of L-histidine with L-histidine hydrochloride with isotonicity agents and potentially pH adjustment with an acid or a base known in the art. Most preferred is histidine (e.g. L-histidine).

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

A "liquid formulation" or "aqueous formulation" according to the invention denotes a formulation which is liquid at a temperature of at least about 2 to about 8° C.

The term "lyophilized formulation" denotes a formulation which is dried by freezing the formulation and subsequently subliming the ice from the frozen content by any freeze-drying methods known in the art, for example commercially available freeze-drying devices. Such formulations can be reconstituted in a suitable diluent, such as water, sterile water for injection, saline solution etc, to form a reconstituted liquid formulation suitable for administration to a subject.

"Hyaluronan" (abbreviated "HA" and also called "hyaluronic acid" or "hyaluronate") is an anionic, nonsulfated glycosaminoglycan distributed widely throughout connective, epithelial, and neural tissues.

"Hyaluronidases" are enzymes that degrade hyaluronic acid. In humans, there are six associated genes, including HYALPI (pseudogene), HYAL1, HYAL2, HYAL3, HYAL4, and PH20/SPAM1. The term herein includes "acid-active" enzymes (such as HYAL1), and "neutral-active" enzymes (such as PH20). It also includes enzymes with or without a glycosylphosphtidy inositol anchor; preferably the hyaluronidase is soluble or lacks an anchor. Hyaluronidases can be included in a pharmaceutical formulation in order to: facilitate administration of the therapeutic drug into the hypodermis, reduce the viscosity of the interstitum, allow larger volumes to be administered SC, and/or increase absorption and dispersion of another injected drug. The hyaluronidase enzyme in a pharmaceutical formulation herein is characterized by having no adverse effect on the molecular integrity of the anti-IL-6R antibody in the formulation, and while it modifies the delivery of the anti-IL-6R antibody to the systemic circulation it does not possess any properties that could provide or contribute to the therapeutic effects of systemically absorbed anti-IL-6R antibody. See, also, WO 2004/078140, WO2006/091871 and U.S. Pat. No. 7,767,429 regarding hyaluronidases according to the present invention. Hyaluronidase products approved in EU countries include HYALASE®. Hyaluronidase products of animal origin approved in the US include VITRASE™, HYDRASE™ and AMPHADASE™. The preferred hyaluronidase herein is recombinant human PH20.

"Recombinant human PH20" (abbreviated "rHuPH20") refers to a soluble, neutral pH-active enzyme comprising a truncated human PH20 amino acid sequence. It can be synthesized with a 35 amino acid signal peptide that is removed from the N-terminus during the process of secretion so as to provide an N-terminal amino acid sequence found in some bovine hyaluronidase preparations. Preferably, rHuPH20 herein comprises the amino acid sequence available under CAS Registry No. 757971-58-7 or as disclosed in U.S. Pat. No. 7,767,429, expressly incorporated herein by reference, and has an approximate molecular weight of 61 kDa. See, also, Frost, G. I., "Recombinant human hyaluronidase (rHuPH20): an enabling platform for subcutaneous drug and fluid administration", *Expert Opinion on Drug Delivery* 4: 427-440 (2007)). The term herein includes rHuPH20 (HYLENEX®) commercially available from Halozyme Therapeutics Inc.

A "subcutaneous administration device" refers to a device, such as syringe, injection device, infusion pump, injector pen, needleless device, patch delivery system, etc, which is adapted or designed to administer a drug or pharmaceutical formulation by the subcutaneous route. In one embodiment, the device administers about 0.9 mL, 1.8 mL, or 3.6 mL of a pharmaceutical formulation.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

Herein, a "fibrotic disease" is one involving the formation of excess fibrous connective tissue in an organ and/or tissue. Examples of fibrotic diseases herein include: systemic sclerosis (scleroderma), keloids, hypertrophic scars, burn scars, liver fibrosis, liver cirrhosis, pulmonary hypertension, pulmonary fibrosis (including idiopathic pulmonary fibrosis, IPF), cardiac fibrosis, kidney fibrosis, hepatic fibrosis, etc. In one embodiment, the fibrotic disease is systemic sclerosis.

"Systemic sclerosis" (SSc) or "scleroderma" is a complex and heterogeneous disease with skin and tissue fibrosis, vascular alterations, and autoantibodies against various cellular antigens being amongst its principal features. The clinical manifestations of systemic sclerosis can range from limited skin involvement to severe internal organ dysfunction. Internal visceral organ pathology is a major factor contributing to the morbidity of this disease, with the kidneys, esophagus, heart, and lungs being the most frequently involved. There are two major subgroups in the commonly accepted classification of SSc: limited cutaneous SSC (lcSSc) and diffuse cutaneous SSC (dcSSc). Gabrielli et al. Mechanisms of disease. *Scleroderma. N Engl J Med* 360:1989-2003 (2009).

In one embodiment, the patient with systemic sclerosis has been classified according to the American College of Rheumatology (formerly, the American Rheumatism Association) criteria for the classification of systemic scleroderma based on:

major criterion: proximal diffuse (truncal) sclerosis (skin tightness, thickening, and non-pitting induration); and minor criteria: (1) sclerodactyly (only fingers and/or toes), (2) digital pitting scars or loss of substance of the digital finger pads (pulp loss), and (3) bilateral basilar pulmonary fibrosis, wherein a patient with systemic sclerosis should fulfill the major criterion or two of the three minor criteria. See Subcommittee for Scleroderma Criteria of the American Rheumatism Association, Diagnostic and Therapeutic Criteria Committee. Preliminary criteria for the classification of systemic sclerosis (scleroderma). *Arthritis Rheum* 23:581-90 (1980).

II. Production of Anti-IL-6R Antibodies

The methods and articles of manufacture of the present invention use, or incorporate, an antibody that binds to human IL-6R. IL-6R antigen to be used for production of, or screening for, antibodies may be, e.g., a soluble form of IL-6R or a portion thereof (e.g. the extracellular domain), containing the desired epitope. Alternatively, or additionally, cells expressing IL-6R at their cell surface can be used to generate, or screen for, antibodies. Other forms of IL-6R useful for generating antibodies will be apparent to those skilled in the art.

In one embodiment, the antibody is an antibody fragment, various such fragments being disclosed above.

In another embodiment, the antibody is an intact or full-length antibody. Depending on the amino acid sequence of the constant domain of their heavy chains, intact antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known. In a preferred embodiment, the anti-IL-6R antibody is an IgG1 or IgM antibody.

Techniques for generating antibodies are known and examples provided above in the definitions section of this document. In a preferred embodiment, the antibody is a chimeric, humanized, or human antibody or antigen-binding fragment thereof. Preferably the antibody is a humanized full-length antibody.

Various techniques are available for determining binding of the antibody to the IL-6R. One such assay is an enzyme linked immunosorbent assay (ELISA) for confirming an ability to bind to human IL-6R. See, for example, U.S. Pat. No. 5,795,965. According to this assay, plates coated with IL-6R (e.g. recombinant sIL-6R) are incubated with a sample comprising the anti-IL-6R antibody and binding of the antibody to the sIL-6R is determined.

Preferably, the anti-IL-6R antibody is neutralizes IL-6 activity, e.g. by inhibiting binding of IL-6 to IL-6R. An exemplary method for evaluating such inhibition is disclosed in U.S. Pat. Nos. 5,670,373, and 5,795,965, for example. According to this method, the ability of the antibody to compete with IL-6 to IL-6R is evaluated. For example, a plate is coated with IL-6R (e.g. recombinant sIL-6R), a sample comprising the anti-IL-6R antibody with labeled IL-6 is added, and the ability of the antibody to block binding of the labeled IL-6 to the IL-6R is measured. See, U.S. Pat. No. 5,795,965. Alternatively, or additionally, identification of binding of IL-6 to membrane-bound IL-6R is carried out according to the method of Taga et al. *J. Exp. Med.*, 166: 967 (1987). An assay for confirming neutralizing activity using the IL-6-dependent human T-cell leukemia line KT3 is also available, see, U.S. Pat. No. 5,670,373, and Shimizu et al. *Blood* 72: 1826 (1988).

Non-limiting examples of anti-IL-6R antibodies herein include PM-1 antibody (Hirata et al., *J. Immunol.* 143:2900-2906 (1989), AUK12-20, AUK64-7, and AUK146-15 antibody (U.S. Pat. No. 5,795,965), as well as humanized variants thereof, including, for example, tocilizumab. See, U.S. Pat. No. 5,795,965. Preferred examples of the reshaped human antibodies used in the present invention include humanized or reshaped anti-interleukin (IL-6) receptor antibodies (hPM-1 or MRA) (see U.S. Pat. No. 5,795,965).

The antibody herein is preferably recombinantly produced in a host cell transformed with nucleic acid sequences encoding its heavy and light chains (e.g. where the host cell has been transformed by one or more vectors with the nucleic acid therein). The preferred host cell is a mammalian cell, most preferably a Chinese Hamster Ovary (CHO) cells.

III. Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as TWEEN™, PLURONICS™ or polyethylene glycol (PEG).

The formulation herein may also contain more than one active compound as necessary, preferably those with complementary activities that do not adversely affect each other. The type and effective amounts of such medicaments depend, for example, on the amount of antibody present in the formulation, and clinical parameters of the subjects. Exemplary such medicaments are discussed below.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

In one embodiment, the anti-IL-6R antibody-containing liquid formulation according to the present invention contains a high concentration of the anti-IL-6R antibody, preferably from 50 to 300 mg/mL, more preferably from 100 to 300 mg/mL, still more preferably from 120 to 250 mg/mL, and yet more preferably from 150 to 200 mg/mL, for example about 180 mg/mL, of the anti-IL-6R antibody.

In one embodiment, the formulation with high anti-IL-6R antibody concentration includes arginine and/or methionine as stabilizers or excipients in the formulation.

As the arginine used in the present invention, any of the arginine compound per se, derivatives thereof and salts thereof can be used. L-arginine and salts thereof are preferred. As the methionine used in the present invention, any of the methionine compound per se, derivatives thereof and salts thereof can be used. L-methionine and salts thereof are preferred. In cases where the antibody-containing liquid formulation according to the present invention contains arginine and does not contain methionine, the concentration of arginine is preferably 50 to 1500 mM, more preferably 100 to 1000 mM, still more preferably 200 to 700 mM. In cases where the antibody-containing liquid formulation according to the present invention contains arginine and methionine, the total concentration of arginine and methionine is preferably 50 to 1200 mM, for example, preferably, the arginine concentration is 40 to 1000 mM and the methionine concentration is 10 to 200 mM; more preferably, the arginine concentration is 50 to 700 mM and the methionine concentration is 10 to 100 mM; and still more preferably, the arginine concentration is 100 to 300 mM, and the methionine concentration is 10 to 50 mM.

The buffer solution is prepared using a buffering agent which is a substance for maintaining a pH of the solution. In a high concentration antibody-containing liquid formulation according to the present invention, a pH of the formulation is preferably 5 to 7, more preferably 5.5 to 6.5, and most preferably pH 6. A buffering agent which can be used in the present invention is one which can adjust the pH in this range and which is pharmaceutically acceptable. Such a buffering agent is known by those skilled in the art, and examples thereof include inorganic salts such as phosphoric acid salts (sodium or potassium) and sodium hydrogen carbonate; organic acid salts such as citric acid salts (sodium or potassium), sodium acetate and sodium succinate; and acids such as phosphoric acid, carbonic acid, citric acid, succinic acid, malic acid and gluconic acid. Further, Tris buffers, Good's buffers such as MES, MOPS and HEPES, histidine (e.g., histidine hydrochloric acid salt) and glycine can also be used. The buffer is preferably a histidine buffer or glycine buffer, and a histidine buffer is especially preferred. The concentration of the buffer solution is generally 1 to 500 mM, preferably 5 to 100 mM, still more preferably 10 to 20 mM. In cases where a histidine buffer is used, the buffer solution contains histidine at a concentration of preferably 5 to 25 mM, more preferably 10 to 20 mM.

The formulation according to the present invention can further contain a surfactant. Typical examples of the surfactant include nonionic surfactants, for example, sorbitan fatty acid esters such as sorbitan monocaprylate, sorbitan monolaurate and sorbitan monopalmitate; glycerin fatty acid esters such as glycerol monocaprylate, glycerol monomyristate and glycerol monostearate; polyglycerol fatty acid esters such as decaglyceryl monostearate, decaglyceryl distearate and decaglyceryl monolinoleate; polyoxyethylene sorbitan fatty acid esters such as polyoxyethylene sorbitan monolaurate, polyoxyethylene sorbitan monooleate, polyoxyethylenesorbitan monostearate, polyoxyethylene sorbitan monopalmitate, polyoxyethylene sorbitan trioleate and polyoxyethylene sorbitan tristearate; polyoxyethylene sorbitol fatty acid esters such as polyoxyethylene sorbitol tetrastearate and polyoxyethylene sorbitol tetra oleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether and polyoxyethylene polyoxypropylene cetyl ether; polyoxyethylene alkyl phenyl ethers such as polyoxyethylene nonylphenyl ether; polyoxyethylene hardened castor oils such as polyoxyethylene castor oil and polyoxyethylene hardened castor oil (polyoxyethylene hydrogenated castor oil); polyoxyethylene bees wax derivatives such as polyoxyethylene sorbitol bees wax; polyoxyethylene lanolin derivatives such as polyoxyethylene lanolin; surfactants having an HLB of 6 to 18 such as polyoxyethylene fatty acid amides, for example, polyoxyethylene octadecanamide; anionic surfactants, for example, alkyl sulfate salts having a $C_{10}$-$C_{18}$ alkyl group, such as sodium cetyl sulfate, sodium lauryl sulfate and sodium oleyl sulfate; polyoxyethylene alkyl ether sulfate salts in which the average number of moles of the added ethylene oxide units is 2 to 4 and the number of carbon atoms of the alkyl group is 10 to 18, such as polyoxyethylene sodium lauryl sulfate; alkyl sulfosuccinate salts having a $C_8$-$C_{18}$ alkyl group, such as sodium lauryl sulfosuccinate; natural surfactants such as lecithin and glycerophospholipids; sphingophospholipids such as sphingomyelin; and sucrose esters of $C_{12}$-$C_{18}$ fatty acids. These surfactants can be added to the formulation of the present invention individually, or two or more of these surfactants can be added in combination.

Preferred surfactants are polyoxyethylene sorbitan fatty acid esters and polyoxyethylene polyoxypropylene alkyl ethers, and especially preferred are polysorbates 20, 21, 40, 60, 65, 80, 81 and 85, and Pluronic type surfactants, and most preferred are polysorbates 20 and 80, and Pluronic F-68 (Poloxamer 188).

The amount of the surfactant(s) to be added to the antibody formulation according to the present invention is generally 0.0001 to 10% (w/v), preferably 0.001 to 5%, more preferably 0.005 to 3%.

In one embodiment, the formulation according to the present invention comprises: (a) anti-IL-6 receptor antibody; (b) buffering agent(s) (e.g. histidine buffer); (c) one or more amino acids as stabilizers (e.g. arginine and/or methionine); and (d) one or more surfactant(s).

In one embodiment, the formulation additionally includes one or more hyaluronidases (e.g. rHuPH20) in an amount which allows the administration of higher volumes of drug product and/or for enhancing absorption of subcutaneously administered anti-IL-6R antibody into the systemic circulation of a patient treated with the formulation.

According to this embodiment of the invention, a pharmaceutical composition is provided comprising: an anti-IL-6R antibody (e.g. tocilizumab) in an amount from about 100 mg/mL to about 300 mg/mL (e.g. 180 mg/mL), and hyaluronidase enzyme in an amount from about 1,400 to about 1,600 U/mL (e.g. about 1,500 U/mL). Preferably the composition further comprises a buffer (for instance, wherein the buffer is histidine, pH 5.5 to 6.5) and/or one or more stabilizers (for example, methionine, arginine, and polysorbate).

The concentration of the hyaluronidase enzyme in the formulation is provided in sufficient amount so that an increase in the dispersion and absorption of the co-administered anti-IL-6R antibody is achieved. The effective amount of the hyaluronidase enzyme is preferably about 1,000 to 16,000 U/ml, whereby the amount corresponds to about 0.01 mg to 0.15 mg protein based on an assumed specific activity of 100,000 U/mg. The preferred concentration of the hyaluronidase enzyme in the formulation is about 1,400 U/mL to 1,600 U/mL, most preferred is a concentration of about 1,500 U/mL.

The hyaluronidase enzyme may be derived from animals, human samples or manufactured based on recombinant DNA technology. Most preferred is recombinant human PH20 (rhPH20).

Preferably the formulation is isotonic.

IV. Therapeutic Uses of Anti-IL-6R Antibodies

In one aspect, the invention provides a method of treating an IL-6-mediated disorder in a patient comprising subcutaneously administering an anti-IL-6 receptor (IL-6R) antibody to the patient, wherein the anti-IL-6R antibody is administered as a fixed dose of 162 mg per dose (e.g every week, every two weeks, or every ten days).

Examples of IL-6-mediated disorders to be treated herein include: autoimmune diseases, osteoporosis, neoplasia, aging, rheumatoid arthritis (RA), juvenile idiopathic arthritis (JIA) (including systemic JIA (sJIA) and polyarticular course JIA (pcJIA)), psoriatic arthritis, Castleman's disease, Crohn's disease, multiple myeloma, polymyalgia rheumatica, glomerulonephritis, plasmacytoma or plasmacytosis, myeloma (including multiple myeloma), hyperimmunoglobulinemia, anemia, nephritis (such as mesangium proliferative nephritis), cachexia (including cancerous cachexia), tumors, T cell mediated disease (e.g. uveitis, chronic thyroiditis, delayed hypersensitivity, contact dermatitis, or atopic dermatitis), lupus (including lupus nephritis and systemic lupus erythmatosus), inflammatory bowel disease (including Crohn's disease and ulcerative colitis), pancreatitis, psoriasis, osteoarthritis, adult-onset Still's disease, mesothelioma, vasculitis, islet transplantation (e.g. pancreatic islet transplantation), myocardial infarction (heart failure, ischemia-induced severe arrhythmia), heart transplantation, prostate cancer, choroidal neovascularization (e.g. age-related macular degeneration, idiopathic choroidal neovascularization, cyopic choroidal neovascularization, idiopathic choroidal neovascularization), muscle atrophy, chronic rejection, ocular inflammatory disease (e.g. panuveitis, anterior aveitis, intermediate uveitis, scleritis, keratitis, orbital inflammation, optic neuritis, dry eye, diabetic retinopathy, proliferative vitreoretinopathy, postoperative inflammation), graft versus host disease (GVHD), fibrotic disorders (such as systemic sclerosis), giant cell arteritis (GCA), ankylosing spondylitis, and Takayasu's arteritis (TA), arteritis nodosa, etc.

In one embodiment, the IL-6-mediated disorder is rheumatoid arthritis.

In one embodiment, the IL-6 mediated disorder is juvenile idiopathic arthritis (JIA).

In one embodiment, the IL-6 mediated disorder is systemic JIA (sJIA).

In one embodiment, the IL-6 mediated disorder is polyarticular course JIA (pcJIA).

In one embodiment, the IL-6 mediated disorder is systemic sclerosis.

In one embodiment, the IL-6 mediated disorder is giant cell arteritis (GCA).

In one embodiment, the IL-6 mediated disorder is psoriatic arthritis.

In one embodiment, the IL-6 mediated disorder is uveitis.

In one embodiment, the patient to be treated has rheumatoid arthritis, with such patients including DMARD-inadequate responder patients, TNF-inhibitor-inadequate responder patients, patients who are methotrexate (MTX) naive or have discontinued MTX, patients with active disease, patients with moderate-severe RA etc.

In one embodiment, the method comprises treating rheumatoid arthritis in a patient by subcutaneously administering tociluzumab to the patient, wherein the tociliuzmab is administered as a fixed dose of 162 mg per dose every week or every two weeks. Optionally, the patient is additionally treated with one or more non-biological disease modifying anti-rheumatic drugs (DMARDs), such as methotrexate etc.

The invention also concerns a method of inhibiting progression of structural joint damage in a rheumatoid arthritis (RA) patient by subcutaneously administering a fixed dose of 162 mg of an anti-IL-6R antibody to the patient every two weeks. According to this method, structural joint damage can be assessed at week 24 (or 6 months) and/or week 48 (or 1 year) and found to be inhibited (e.g. relative to a patient not treated with the anti-IL-6R antibody).

The invention additionally provides a method of treating an IL-6-mediated disorder (such as RA) in a patient comprising subcutaneously administering an anti-IL-6R antibody (e.g. tocilizumab) and a hyaluronidase enzyme (e.g., rhPH20) to a patient, wherein the anti-IL-6R antibody is administered as a fixed dose of 324 mg per dose or 648 mg per dose. Preferably, the fixed dose is administered every four weeks or once a month. Optionally, the anti-IL-6R antibody and hyaluronidase enzyme are co-formulated or combined into a single pharmaceutical composition which is subcutaneously administered to the patient.

According to the present invention, the anti-IL-6R antibody may be administered with a hyaluronidase enzyme, such as rHuPH20. The final dose of the rHuPH20 depends on the volume of formulation administered. Exemplary doses of the hyaluronidase administered are in the range from 1,000 to 10,000 U, e.g. about 1,350 U, about 2,700 U, or about 5,400 U. For example, 1,350 U of rHuPH20 is administered in 0.9 mL; 2,700 U of rHuPH20 in 1.8 mL; or 5,400 U of rHuPH20 in 3.6 mL. The anti-IL-6R antibody and hyaluronidase enzyme may be administered concurrently or sequentially, in the same, or separate formulations. Preferably the antibody and enzyme are co-formulated and administered concurrently, e.g. via a single SC administration device. In one embodiment, the anti-IL-6R antibody (e.g. tocilizumab) is subcutaneously administered to a patient with juvenile idiopathic arthritis (JIA) in an amount effective to treat the JIA.

In one embodiment, the patient has systemic JIA (sJIA). Such sJIA patient is optionally treated with 162 mg of the antibody (e.g. of tocilizumab) every week if the patient's weight is ≥30 kilograms, and with 162 mg of the antibody (e.g. of tociliumab) every 10 (±1) days if the patient's weight is <30 kilograms. In an alternative embodiment, the sJIA patient whose weight is <30 kilograms is treated with 162 mg of the antibody (e.g. of tocilizumab) every week or every two weeks. In yet another embodiment, the sJIA patient whose weight is <30 kilograms is treated with 108 mg of the antibody (e.g. of tocilizumab) every week.

In another embodiment, the patient has polyarticular course (pcJIA). Such patient is optionally treated with 162 mg of the antibody (e.g. of tocilizumab) every two weeks.

In another embodiment, the anti-IL-6R antibody is subcutaneously administered to a patient with a fibrotic disease (such as systemic sclerosis) in an amount effective to treat the fibrotic disease. Where the disorder is systemic sclerosis, the treatment optionally improves cutaneous sclerosis (e.g. as assessed by modified Rodnan skin score (mRSS)), improves physical function (e.g. as assessed by Scleroderma Health Assessment Questionnaire-Disability Index (HAQ-DI)), and/or slows progression of organ damage, relative to placebo. For treatment of fibrotic disease, such as systemic sclerosis, the antibody (e.g. tocilizumab) is optionally administered as a fixed dose of 162 mg per dose, for instance every week, or every two weeks.

In a further embodiment, the anti-IL-6R antibody is subcutaneously administered to treat giant cell arteritis (GCA) in an amount effective to treat the GCA. Optionally, the antibody is administered to the GCA patient as a fixed dose of 162 mg per dose (e.g. every week. or every two weeks). The GCA patient optionally is further treated with an initial (short) course or corticosteroid. Such treatment of GCA may reduce signs and symptoms of GCA, maintain clinical remission, and/or reduce or stop corticosteroid use in the GCA patient. The GCA herein includes new onset GCA and refractory GCA, optionally in adult patients.

In one embodiment of all the methods herein, no other medicament than the anti-IL-6R antibody (optionally co-formulated with the hyaluronidase enzyme) is administered to the subject to treat the IL-6-mediated disorder.

In another embodiment of any of the methods herein, one may administer to the subject along with the anti-IL-6R antibody an effective amount of one or more additional drug that treats the disorder. The additional drug may be one or more medicaments, and include, for example, immunosuppressive agents, non-steroidal anti-inflammatory drugs (NSAIDs), disease modifying anti-rheumatic drugs (DMARDs), methotrexate (MTX), anti-B-cell surface marker antibodies, anti-CD20 antibodies, rituximab, TNF-inhibitors, corticosteroids, and co-stimulatory modifiers, or any combination thereof.

Examples of such additional drugs include an immunosuppressive agent (such as mitoxantrone (NOVANTRONE®), methotrexate, cyclophosphamide, chlorambucil, leflunomide, and azathioprine), intravenous immunoglobulin (gamma globulin), lymphocyte-depleting therapy (e.g., mitoxantrone, cyclophosphamide, CAMPATH™ antibodies, anti-CD4, cladribine, a polypeptide construct with at least two domains comprising a de-immunized, autoreactive antigen or its fragment that is specifically recognized by the Ig receptors of autoreactive B-cells (WO 2003/68822), total body irradiation, bone marrow transplantation), integrin antagonist or antibody (e.g., an LFA-1 antibody such as efalizumab/RAPTIVA® commercially available from Genentech, or an alpha 4 integrin antibody such as natalizumab/ANTEGREN® available from Biogen, or others as noted above), steroid such as corticosteroid (e.g., prednisolone, methylprednisolone such as SOLU-MEDROL™ methylprednisolone sodium succinate for injection, prednisone such as low-dose prednisone, dexamethasone, or glucocorticoid, e.g., via joint injection, including systemic corticosteroid therapy), non-lymphocyte-depleting immunosuppressive therapy (e.g., MMF or cyclosporine), cholesterol-lowering drug of the "statin" class (which includes cerivastatin (BAYCOL™), fluvastatin (LESCOL™), atorvastatin (LIPITOR™), lovastatin (MEVACOR™), pravastatin (PRAVACHOL™), and simvastatin (ZOCOR™)), estradiol, testosterone (optionally at elevated dosages; Stuve et al. Neurology 8:290-301 (2002)), androgen, hormone-replacement therapy, a TNF inhibitor such as an antibody to TNF-alpha, DMARD, NSAID, plasmapheresis or plasma exchange, trimethoprim-sulfamethoxazole (BACTRIM™, SEPTRA™), mycophenolate mofetil, H2-blockers or proton-pump inhibitors (during the use of potentially ulcerogenic immunosuppressive therapy), levothyroxine, cyclosporin A (e.g. SANDIMMUNE®), somatastatin analogue, a DMARD or NSAID, cytokine antagonist such as antibody, anti-metabolite, immunosuppressive agent, rehabilitative surgery, radioiodine, thyroidectomy, BAFF antagonist such as BAFF or BR3 antibodies or immunoadhesins, anti-CD40 receptor or anti-CD40 ligand (CD154), B-cell antagonists or antibodies, including anti-CD20 antibodies such as rituximab or ofatumumab; IL-1 blockers, such as rHUIL-1Ra (Anakira, Amgen-Synergen) and tiaprofenic acid I-1B inhibitor (Hoechst); and co-stimulatory modifiers, such as CTLA-4-Ig fusion protein ORENCIA® (abatacept) (Bristol-Myers Squibb); enlimomab (anti-ICAM-1 monoclonal antibody); CDO-855 (humanized antibody, which binds specifically to a region of the Class II MHC complex, Celltech); CH-3298 (Chiroscience); acemetacin (Merck); GW353430 (anti-CD23 monoclonal antibody, Glaxo Wellcome); GR 252025 (COX02 inhibitor, Glaxo Wellcome); 4162W94 (anti-CD4 humanized antibody; Glaxo Wellcome); azathioprine (DMARD, Glaxo Welcome); penicilamine and fenoprofen (Eli Lilly); etc.

Optionally, the second or additional drug is selected from the group consisting of non-biological DMARDS, NSAIDs, and corticosteroids.

These additional drugs as set forth herein are generally used in the same dosages and with administration routes as used hereinbefore or about from 1 to 99% of the heretofore-employed dosages. If such additional drugs are used at all, preferably, they are used in lower amounts than if the first medicament were not present, especially in subsequent dosings beyond the initial dosing with the first medicament, so as to eliminate or reduce side effects caused thereby.

The combined administration of an additional drug includes co-administration (concurrent administration), using separate formulations or a single pharmaceutical formulation, and consecutive administration in either order, wherein preferably there is a time period while both (or all) active agents (medicaments) simultaneously exert their biological activities.

In one embodiment, before or after the SC doses are administered, the patient may be treated with anti-IL-6R antibody which is administered IV.

V. Articles of Manufacture

In another embodiment of the invention, articles of manufacture containing materials useful for the treatment of IL-6-mediated disorders described above are provided. The invention, in particular, provides an article of manufacture comprising a subcutaneous administration device, which delivers to a patient a fixed dose of an anti-IL-6 receptor (IL-6R) antibody, wherein the fixed dose is selected from the group consisting of 162 mg, 324 mg, and 648 mg of the anti-IL-6R antibody. Preferably the anti-IL-6R antibody is tocilizumab. Preferably, the concentration of the antibody in the device is from 150 to 200 mg/mL, for example 180 mg/mL. The antibody in the syringe is preferably formulated in a buffer (e.g. histidine, pH 6) and other excipients (such as methionine, arginine, and polysorbate) such that it is provided in a stable pharmaceutical formulation in the syringe. Optionally, a hyaluronidase, such as rHuPH20, is included in the formulation, for example, in an amount from about 1,400 U/mL to about 1,600 U/mL (e.g. about 1,500 U/mL). Optionally, the device delivers 0.9 mL, 1.8 mL, or 3.6 mL of the formulation to a subject.

Devices suitable for SC delivery include: a syringe (including a pre-filled syringe); an injection device (e.g. the INJECT-EASE™ and GENJECT™ device); an infusion pump (such as e.g. Accu-Chek™); an injector pen (such as the GENPEN™); a needleless device (e.g. MEDDECTOR™ and BIOJECTOR™); an autoinjector, a subcutaneous patch delivery system, etc.

The article of manufacture optionally further comprises a package insert with instructions for treating an IL-6-mediated disorder (e.g. RA) in a subject, wherein the instructions indicate that treatment with the antibody as disclosed herein treats the IL-6-mediated disorder, and optionally inhibits progression of structural joint damage (e.g. in a RA patient).

Further details of the invention are illustrated by the following non-limiting Examples. The disclosures of all citations in the specification are expressly incorporated herein by reference.

Example 1

Clinical Studies Identifying Fixed Dose of Anti-IL-6R Antibody for Subcutaneous (SC) Administration The selection of 162 mg anti-IL-6R antibody (tocilizumab, TCZ) subcutaneously administered every week (SC QW) was based on results from four phase 1/2 studies, including two phase 1 studies in healthy subjects (WP18097 and BP22065), one phase 1/2 study in Japanese RA patients (MRA227), and one phase 1b study in Caucasian RA patients (NP22623). Further details regarding these SC studies and the four studies from which data are drawn for comparison are provided in Table 1.

These studies used a TCZ formulation with 180 mg/mL TCZ and no hyaluronidase (see Table 2 in Example 4).

In the Japanese RA study MRA227, all (32) patients were randomized into one of 3 study arms: 81 mg SC Q2W/QW, 162 mg SC Q2W, and 162 mg SC QW. In the Caucasian RA study NP22623, a total of 29 patients were randomized into one of 2 treatment arms: 162 mg SC Q2W (N=15) and 162 mg SC QW (N=14).

The observed data from the two RA patient studies form the primary basis on which the dose rationale has been built.

Figure 1:
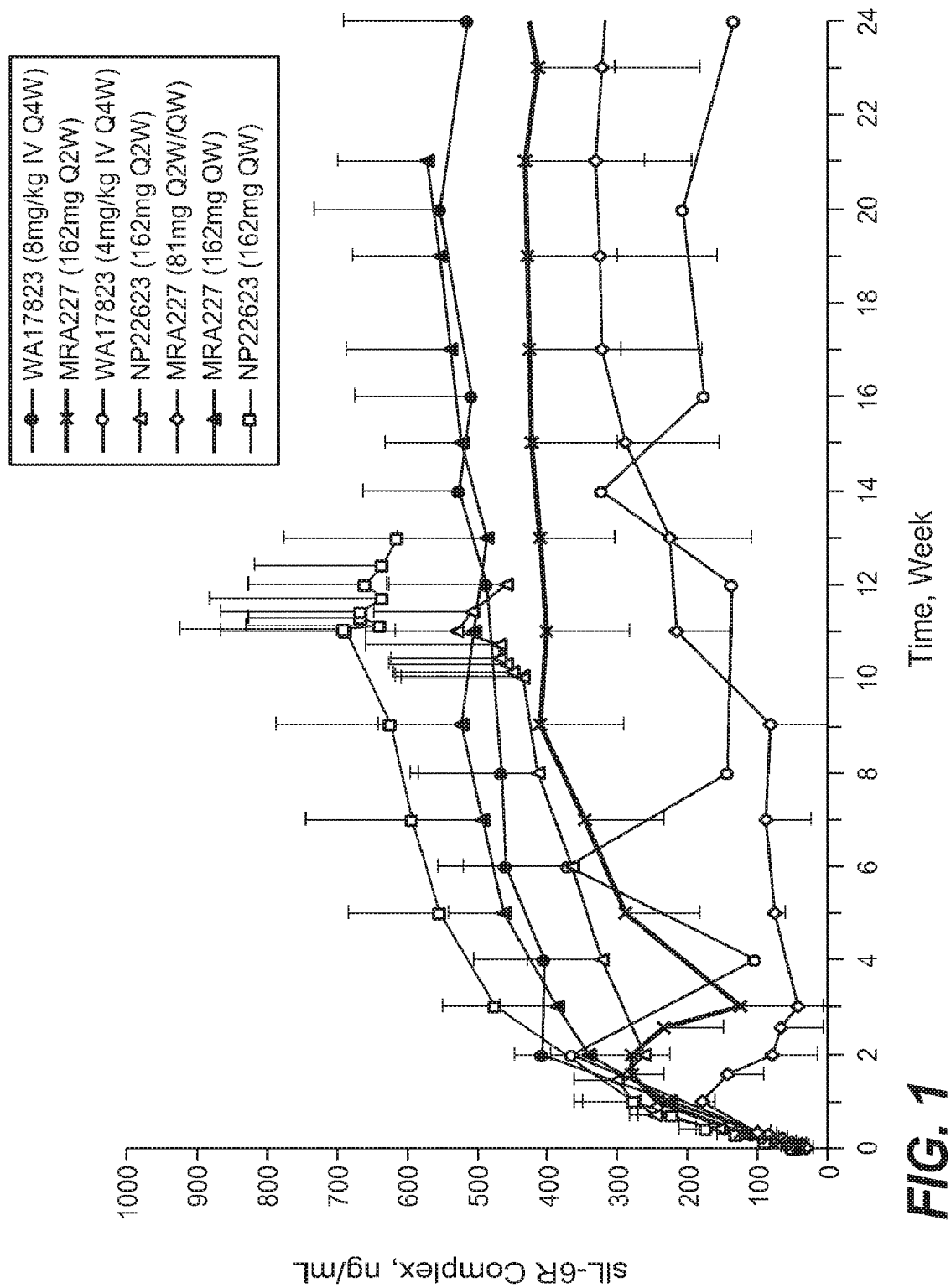
FIG. 1 depicts mean sIL-6R concentration-time profiles following administration of TCZ 162 mg SC QW/Q2W in Japanese (MRA227) and Caucasian (NP22623) RA patients compared with TCZ 4 & 8 mg IV Q4W (WA17823). Key: Japanese RA patients MRA227 study: N=12 for the 162 mg QW group, N=12 for 162 mg Q2W group and N=6 to 8 for the 81 mg QW/Q2W group which had a single dose part of 3 weeks. For the 81 mg group, the regimen was switched from Q2W to QW at week 9; Caucasian RA patients in NP22623 study: N=13 for 162 mg Q2W and N=14 for QW group. WA17823 study: N=146 for 4 mg/kg IV Q4W and N=532 or 8 mg/kg IV in combination with MTX. Error bar denotes standard deviation.

The selection of this 162 mg QW dose regimen was driven by three key elements:

The sIL-6R-bound TCZ complex (PD biomarker of TCZ mechanism of action; Nishimoto et al., *Blood* 112(10): 3959-3964 (2008) increases more rapidly and to a greater magnitude for 162 mg QW than for other SC dose regimens tested (FIG. 1)

Figure 2:
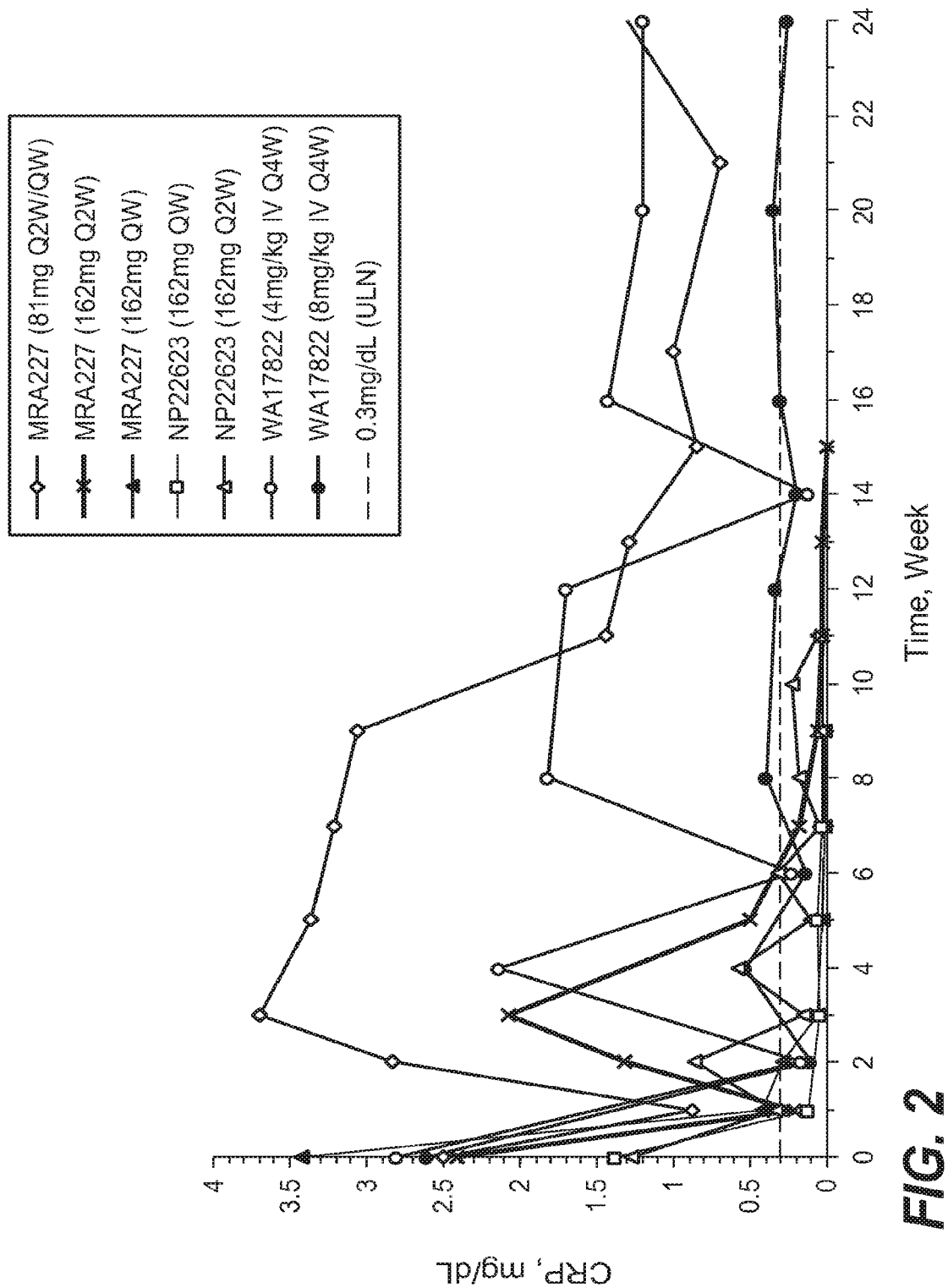
FIG. 2 depicts mean CRP-time profiles following administration of TCZ 162 mg QW/Q2W SC in Japanese (MRA227) and Caucasian (NP22623) RA patients compared with the profile of 4 & 8 mg/kg IV Q4W (WA17822). Key: Japanese RA patients in MRA227 study: N=12 for the 162 mg QW group, N=12 for the 162 mg Q2W group and N=8 up to week 11 and N=7 thereafter for the 81 mg Q2W/QW group including the single dose part of 3 weeks. For the 81 mg group, the regimen was switched from Q2W to QW at week 9; Caucasian RA patients in NP22623 study: N=13 for 162 mg Q2W and N=14 for QW group. WA17822 study: N=152 to 211 for 4 mg/kg IV Q4W and N=167 to 206 for 8 mg/kg IV in combination with MTX. ULN-Upper limit of normal range.

CRP is reduced more rapidly and consistently with the 162 mg QW than with the other SC dose regimens tested (FIG. 2)

The safety profile for the SC treatment arms do not appear to be different from each other or from 8 mg/kg IV Q4W.

In general, the SC dose regimens tested have been well tolerated in the MRA227 and NP22623 studies.

Notably there have been no deaths and only one SAE (pyelonephritis) in the SC treatment arms.

Figure 4:
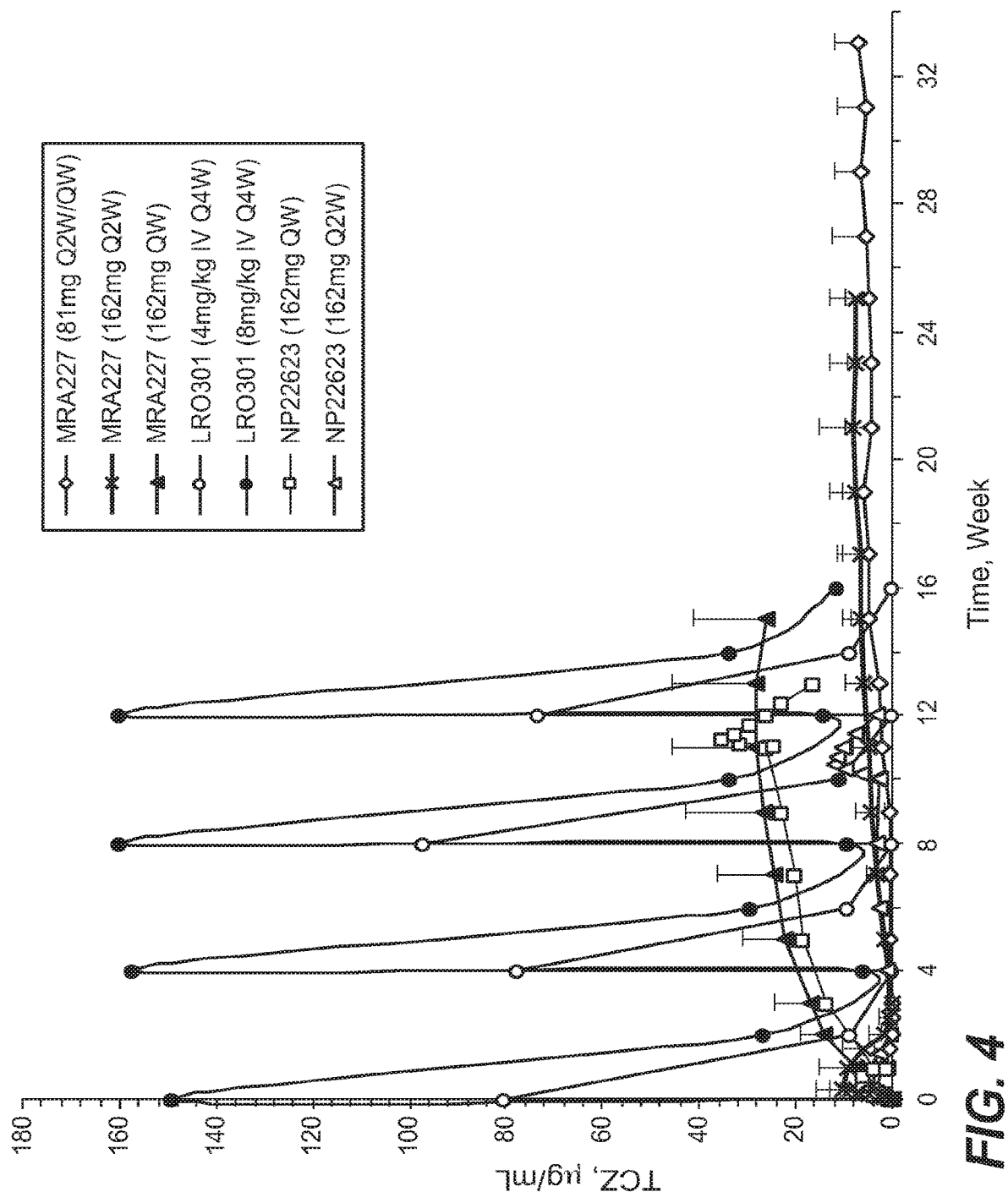
FIG. 4 depicts mean±SD serum TCZ concentrations following administration of 162 mg SC QW and Q2W in Study MRA227 and 4 & 8 mg/kg IV Q4W in Study LRO301. Key: Group 1 (N=8 up to week 11 and N=7 thereafter): patients received 81 mg SC single dose at week 1, started QW dosing at week 3, and switched to Q2W dosing at week 9; Group 2 (162 mg Q2W, N=12): patients received single 162 mg SC dose at week 1 and started Q2W dosing at week 3.

Given that mean exposure (AUC, $C_{max}$) is generally higher for 8 mg/kg IV Q4W than for any of the SC dose regimens, the safety profile for 162 mg QW is expected to be similar to that of 8 mg/kg IV (FIG. 4).

sIL-6R

FIG. 1 demonstrates sIL-6R profiles following both SC and IV regimens. sIL-6R profiles for RA patients receiving

TABLE 1

Clinical Pharmacology Studies Following SC Administration of TCZ in Healthy Subjects and RA Patients

| Study No. Country | Objectives | Design and Population | TCZ Treatment/ Dose | Duration | Sample Size | Status |
|---|---|---|---|---|---|---|
| WP18097 France | PK from a pilot SC formulation, absolute bioavailability, tolerability and immunogenicity | Single center, single-blind, placebo-controlled, randomized, 2 groups study in Healthy Volunteers | Group 1: 160 mg SC Group 2: 160 mg IV | Single dose, PK sampling up to Day 14, one-week follow-up, TCZ antibody at baseline, day 14 and follow-up | N = 20 total and n = 12 for SC group and 8 for IV group | Completed |
| BP22065 UK | PK, PD, safety, tolerability, immunogenicity and absolute bioavailability using SC formulation of TCZ | Open-label, single-center study to characterize the PK and PD of TCZ following single dose administration by SC and IV routes to Healthy Volunteers | SC injection in abdominal region: Group 1: 162 mg Group 2: 81 mg IV infusion: Group 3: 162 mg Group 4: 81 mg | Single dose for each group, PK and PD sampling up to Day 25, one week follow up. TCZ antibody at baseline, day 25 and follow-up | N = 48 total and n = 12 for each group | Completed |
| NP22623 Spain, New Zealand, and Canada | PK, PD, safety, immunogenicity and efficacy | Open label, multicenter, randomized, parallel study in RA patients | Group 1: TCZ 162 mg QW Group 2: 162 mg TCZ Q2W in combination with MTX in patients with active RA | 12 weeks of treatment. PK/PD sampling from baseline to the end of study. Patients have option to be rolled over to a provisional care program for one year treatment (8 mg/kg IV) | N = 29 total and n = 14 for TCZ QW and n = 15 for TCZ Q2W | 29 enrolled, study ongoing Preliminary data summary for efficacy and safety are available |
| MRA227 Japan | PK, PD, safety, immunogenicity and efficacy | Combined single- and multi-dosing study in RA patients. 3 Groups. Dose escalation is based on the safety and efficacy from previous group. | Group 1: TCZ 81 mg single dose followed by Q2W Group 2: TCZ 162 mg single dose followed by Q2W Group3: TCZ 162 mg QW | Single dose in Group 1 and 2 is followed by 3 weeks PK and PD sampling Multi-dosing for all 3 groups is for 3 doses (6 weeks for Q2W and 3 weeks for QW) followed by 24 weeks of extension | N = 32 total n = 8 in Group 1 and n = 12 each for Groups 2 and 3 | 32 enrolled, study ongoing Preliminary data summary for PK/PD/ efficacy and for safety are available |

162 mg QW most closely mirrors that observed with 8 mg/kg IV Q4W, both with respect to the rapidity and magnitude of rise. The other dose regimens (81 mg Q2W/QW or 162 mg Q2W) tested did not reach levels comparable to 8 mg/kg IV Q4W.

CRP

FIG. 2 displays the CRP profile following the 162 mg SC QW and 8 mg/kg IV Q4W dose regimens in RA patients. 162 mg QW has the most rapid and sustained reduction of CRP levels of the SC dose regimens tested.

DAS28-ESR

Figure 3:
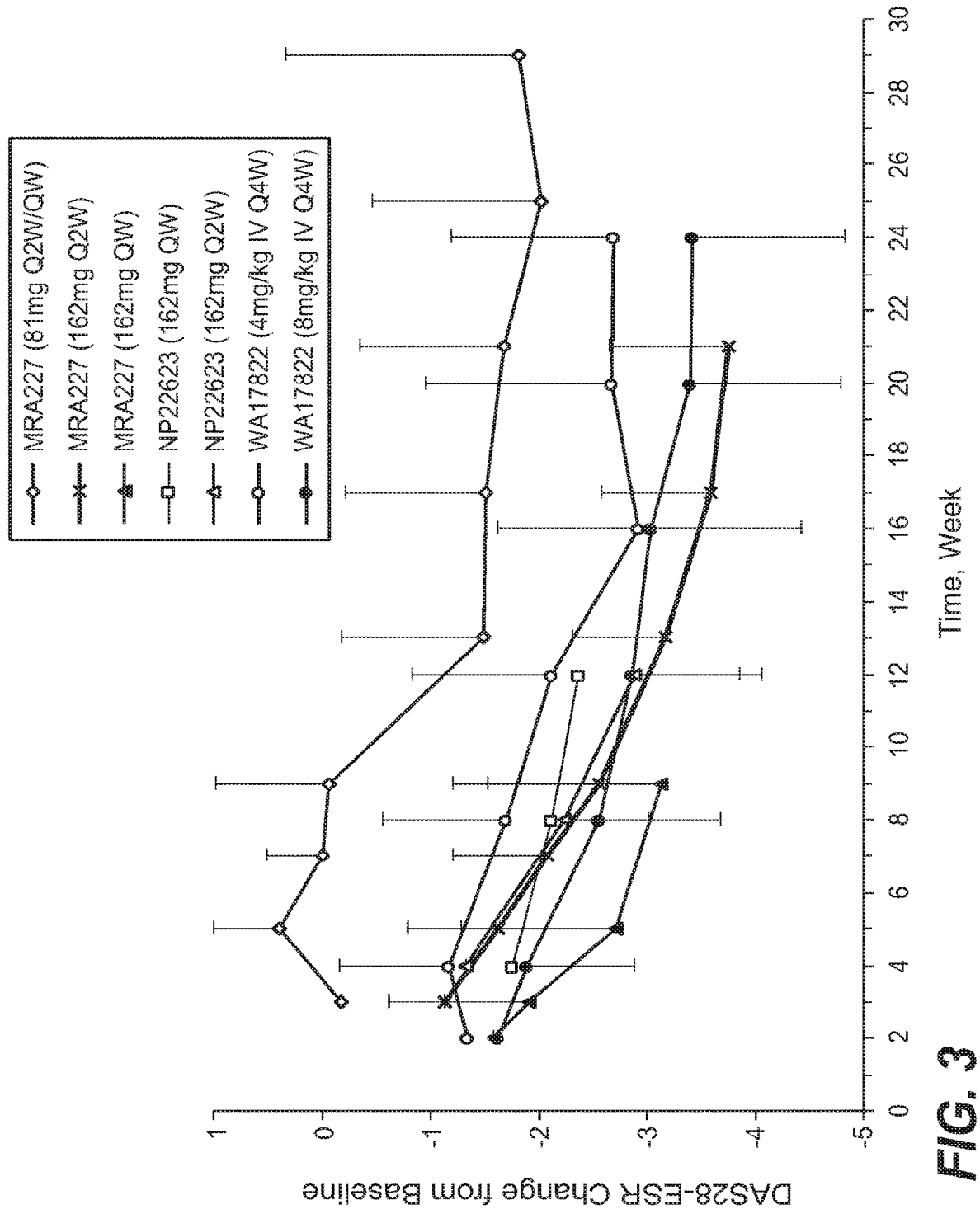
FIG. 3 depicts change in DAS28-ESR from baseline following administration of TCZ in SC studies (MRA227 and NP22623) and in IV Study (WA17822). Key: Japanese SC study in RA patients (MRA227): N=12 for the 162 mg QW group, N=12 for 162 mg Q2W group and N=8 up to week 11 and N=7 thereafter for the 81 mg Q2W/QW group including the single dose part of 3 weeks. For the 81 mg group, the regimen was switched from Q2W to QW at week 9; Caucasian SC study in RA patients (NP22623): N=11 for the 162 mg Q2W group+MTX QW and N=12 for the 162 mg QW+MTX QW group. Comparator study WA17822: N=152 to 211 for the 4 mg/kg Q4W+MTX QW group, and N=167 to 206 for 8 mg/kg Q4W+MTX QW group.

Disease activity (as measured by DAS28-ESR) appears to decrease from baseline more rapidly and to a greater magnitude with the 162 mg SC QW as compared to the other SC dose regimens tested (FIG. 3).

Safety: Observed Data

No deaths and only one SAE (pyelonephritis in the 81 mg dose group) have been reported in the 4 TCZ SC studies. AEs observed following single or multiple SC doses for either healthy subjects or RA patients were generally consistent with the types and severity of AEs observed in Phase 3 RA IV studies. Data from NP22623 did not demonstrate different AE profiles between the 162 mg QW and Q2W dose groups. The magnitude of mean changes in laboratory values for both Japanese RA and Caucasian RA patients receiving SC TCZ resembled that of RA patients from the IV program. One Japanese RA patient who received 162 mg QW experienced neutropenia and the dose was reduced to 162 mg Q2W. One patient who received 81 mg Q2W experienced neutropenia and was not dosed further when switched to 81 mg QW at week 11. The SC injection was generally well tolerated. The SC injection was not perceived as more painful than the subcutaneous placebo injection.

In study MRA227, none of the patients tested positive for anti-TCZ antibodies from the 162 mg QW group. Four patients from the lower dose groups were anti-TCZ antibody positive (all from the 81 mg QW/Q2W dose group, one patient prior to TCZ administration); five patients were anti-TCZ IgE antibody positive (3 patients in the 81 mg Q2W/QW dose group and 2 patients in the 162 mg Q2W dose group). Among those with positive antibody tests, the patient positive at baseline experienced grade 1 eczema which was considered as unrelated (food allergy), one patient experienced grade 1 urticaria, and another patient experienced injection site bruising. No other AEs were reported in the "Skin and Subcutaneous Tissue" and "General Disorders and administration site conditions" classes in patients who tested positive for anti-TCZ antibodies.

PK-Safety Relationship

On visual inspection of steady state PK profiles between SC and IV regimens from study MRA227 and LRO301, respectively, there appears to be in general higher exposure (mean AUC, $C_{max}$) with the 8 mg/kg IV regimen as compared to the 162 mg QW SC regimen (FIG. 4). The exception is the mean $C_{trough}$ for which the 162 mg QW regimen results in a higher level than for the 8 mg/kg IV regimen (26±15 µg/mL at week 15 and 16±11 µg/mL at week 16, respectively). Other lower dose groups did not achieve $C_{trough}$ concentrations similar to 8 mg/kg IV at steady state. Inter-subject variability for $C_{trough}$ for the 162 mg SC regimen is high (58%). It is anticipated that since the exposure is generally higher for the 8 mg/kg IV Q4W dose regimens than any of the SC dose regimens, the safety profile for 162 mg SC QW would be similar to that of 8 mg/kg IV Q4W.

A single fixed dose (162 mg QW dose) is administered for all RA patients, irrespective of body weight. This approach is supported by the fact that even after accounting for differences in exposure that could result from the full range of body weights on a fixed dose, the highest exposure for all 3 categories ($C_{max}$, $C_{trough}$ and AUC) with the 162 mg QW dose regimen that has been observed is within the range that has been described for the IV program.

Additionally this approach is supported by analyses of safety data (SAEs, AEs, laboratory) from the IV program. There is no apparent relationship between TCZ exposure and the occurrence of adverse events by class and especially for the most frequent adverse events in the "Infections and Infestations" and "Skin and Subcutaneous Tissue" classes. There is no apparent relationship between exposure of TCZ and the occurrence of serious adverse events. Except for neutropenia, there was no obvious increase in the frequency of laboratory abnormalities with increasing exposure. A slightly greater proportion of patients experienced Grade 3 or higher events of neutropenia in the higher TCZ exposure categories. In addition, there were single Grade 3 events of thrombocytopenia in the higher TCZ exposure categories. With respect to triglycerides, total cholesterol, and LDL-cholesterol levels, a slightly greater proportion of patients developed an increase in levels in the higher TCZ exposure categories. Taken altogether, these data suggest that use of a fixed dose regimen is acceptable.

In summary, the 162 mg SC QW dose regimen has been selected on the basis of: 1) sIL-6R-bound TCZ complex for 162 mg SC QW increased more rapidly and to a greater magnitude for 162 mg SC QW, most similar to 8 mg/kg IV Q4W of the dose regimens tested; 2) CRP is reduced more rapidly and consistently with the 162 mg SC QW than the other SC dose regimens tested; 3) the safety profile for the SC treatment arms do not appear to be different from each other or from 8 mg/kg IV Q4W; and 4) given that the total exposure for 8 mg/kg IV Q4W is generally higher than for any of the SC dose regimens tested, the safety profile for 162 mg SC QW should be similar to 8 mg/kg IV Q4W.

Example 2

Clinical Study of SC Anti-IL-6 Receptor Antibody in RA

This is a Phase 3, 2-arm, 2-year, randomized, double-blind, double-dummy, active controlled, parallel group multicentre trial in patients with moderate to severe, active RA who currently have an inadequate response to a stable dose of DMARDs that may include one or more anti-TNF biological agent. The primary endpoint will be evaluated at 24 weeks. The overall design of this example is shown in FIG. 5. The formulation is that as in Example 1.

The screening visit can occur up to 21 days (or up to 56 days if a washout period is required for longer than 21 days) prior to the baseline randomization visit. Patient eligibility will be determined at the screening and baseline visits, at which time the patient will be randomized. The number of patients that have failed previous anti-TNF treatment will be limited to approximately 20% of the total study population.

Inclusion Criteria

1. Age ≥18 years
2. Rheumatoid arthritis of ≥6 months duration, diagnosed according to the revised 1987 American College of Rheumatology (ACR; formerly American Rheumatism Association) criteria
3. Swollen joint count (SJC)≥4 (66 joint count) and tender joint count (TJC)≥4 (68 joint count) at screening and baseline.

4. Prior to randomization, will have discontinued etanercept for ≥2 weeks, infliximab, certolizumab, golimumab, abatacept or adalimumab for ≥8 weeks, anakinra for ≥1 week.
5. Have received permitted DMARDs at a stable dose for at least 8 weeks prior to baseline.
6. At screening either CRP≥1 mg/dL (10 mg/L) or ESR≥28=AIL
7. Oral corticosteroids (≤10 mg/day prednisone or equivalent) and NSAIDs (up to the maximum recommended dose) are permitted if on a stable dose regimen for ≥4 weeks prior to baseline.

In the double-blind period, at baseline visit, patients will be randomized in a 1:1 ratio to receive either TCZ 162 mg SC weekly and placebo IV Q4W (Group A), or TCZ 8 mg/kg IV Q4W with placebo SC QW (Group B) for 24 weeks. The primary analysis will occur when all patients reach Week 24.

At Week 24, all patients will be re-randomized for the open-label period as follows:
  Group A: patients will be re-randomized in an 11:1 ratio to receive TCZ 162 mg SC weekly (group A1), or 8 mg/kg IV every four weeks (group A2).
  Group B: patients will be re-randomized in a 2:1 ratio to receive 8 mg/kg IV every four weeks (group B1), or TCZ 162 mg SC weekly (group B2).

Prior to the first dose of double-blind study medication (baseline visit), patient-reported outcomes and efficacy assessments should be performed within 24 hours (up to 72 hours will be allowed when necessary). There will be a one-week dose interruption period between Week 24 and 25 before the first treatment for the open-label period at Week 25.

The efficacy parameters will be assessed at baseline, Week 2, Week 4 and then every 4 weeks up to Week 24 and then Week 37, 49, 73 and 97 or early withdraw (WD) visit.

Each treatment group is allowed background therapy with non-biological DMARD(s), corticosteroids and/or NSAIDs that were initiated prior to the start of dosing with TCZ. Dosages of NSAIDs, corticosteroids, and non-biological DMARDs should remain stable during the core study period (up to Week 24). However, reductions in these treatments will be allowed if required for safety reasons.

Assessment of Efficacy
ACR20

The American College of Rheumatology (ACR) core set of outcome measures and their definition of improvement includes a ≥20% improvement compared to baseline in both SJC and TJC as well as in 3 out of 5 additional parameters: physician's global assessment of disease activity, patient's global assessment of disease activity, patient's assessment of pain, HAQ, and acute phase reactant (either CRP or ESR). Achievement of an ACR50 requires a ≥50% improvement in the same parameters and an ACR70 requires a ≥70% improvement.

Disease Activity Score 28 (DAS28)—ESR

The DAS28 is a combined index for measuring disease activity in RA. The index includes swollen and tender joint counts, acute phase response (ESR or CRP), and general health status. For this study ESR will be used to calculate the DAS28 score. The index is calculated using the following formula:

$$DAS28=0.56\times\sqrt{(TJC28)}+0.28\times\sqrt{(SJC28)}+0.36\times\ln(ESR+1)+0.014\times GH+0.96$$

Where, TJC28=tender joint count on 28 joints, SJC28=swollen joint count on 28 joints, ln =natural log, ESR=Erythrocyte sedimentation rate (mm/hr), and GH=general health, i.e., patient's global assessment of disease activity (100-mm VAS). The DAS28 scale ranges from 0 to 10, where higher scores represent higher disease activity.

ACR-Hybrid

ACR-hybrid is a measure that combines the percent improvement of ACR core parameters with the status of ACR20, ACR50 or ACR70.

It is anticipated that treatment with 162 mg TCZ given subcutaneously (SC) weekly as disclosed in this example will have comparable safety and efficacy as compared to 8 mg/kg TCZ given intravenously (IV) every 4 weeks based on any one or more of the above efficacy criteria.

Example 3

Anti-IL-6R Antibody SC for Inhibiting Progression of Joint Damage

This is a Phase 3, 2-arm, 2-year, randomized, double-blind, placebo-controlled, parallel group multicenter trial in patients with moderate to severe, active RA who currently have an inadequate response to DMARD(s) that may include one or more anti-TNF-α agent. The primary endpoint will be evaluated at Week 24.

The overall design is shown in FIG. 6. The screening visit can occur up to 21 days (or up to 56 days if a washout period is required for longer than 21 days) prior to the baseline randomization visit. Patient eligibility will be determined at the screening and baseline visits. At baseline, patients will be randomized. The number of patients that have failed previous anti-TNF-α treatment will be limited to approximately 20% of the total study population. The formulation is that as in Example 1. The formulation is administered using a pre-filled syringe (PFS) or auto-injector (AI) device.

TCZ Q2W Dosing

In this study, 162 mg of TCZ is administered every 2 weeks (Q2W) rather than every week (QW). Compared with the response seen with 162 mg SC QW, 162 mg SC Q2W appears to be a lower SC dose option that, as described below, increases sIL-6R-bound TCZ complex, achieves CRP normalization and results in a DAS-ESR reduction from baseline. Further, the PD responses and the preliminary efficacy readout for the 162 mg SC Q2W regimen are superior to other lower SC regimens tested (81 mg Q2W/QW).

The sIL-6R Complex which is a PD biomarker of TCZ mechanism of action increases with 162 mg SC Q2W less than with 162 mg SC QW but increases to a greater magnitude as compared to other lower SC regimens (81 mg Q2W/QW) (FIG. 1)
  CRP normalization is reached with 162 mg SC Q2W; lower SC regimens did not result in CRP normalization (FIG. 2)
  Disease activity score DAS28-ECR appears to decrease from baseline to a greater magnitude with 162 mg SC QW and 162 mg SC Q2W as compared to the other SC dose regimens tested (81 mg SC Q2W/QW). (FIG. 3)

Safety:

Based on available observed safety data, the safety profile for the SC treatment arms do not appear to be different from each other or from the IV program.
  162 mg SC QW and Q2W have been well tolerated in MRA227 and NP22623 studies.
  There have been no deaths in any of the SC treatment arms. One SAE of pyelonephritis occurred in the 81 mg SC dose group.

Given that mean exposure (AUC, $C_{max}$, $C_{trough}$) is generally higher for the 8 mg/kg IV dose than for 162 mg SC Q2W, the safety profile for 162 mg SC Q2W is expected to be similar to the IV program (FIG. 4).

sIL-6R Complex

The sIL-6R-bound TCZ complex is a PD biomarker of TCZ mechanism of action. FIG. 1 demonstrates sIL-6R profiles following both SC and IV regimens. sIL-6R profiles for RA patients receiving 162 mg SC QW most closely mirrors that observed with 8 mg/kg IV q4w, both with respect to the rapidity and magnitude of rise. The other dose regimens (81 mg Q2W/QW and 162 mg Q2W) tested did not reach levels comparable to 8 mg/kg IV q4w. The dose of 162 mg every other week (Q2W) shows a response that is lower than what is seen with 162 mg QW and 8 mg/kg IV. sIL-6R complex increases to a greater magnitude with 162 mg SC Q2W than with other lower SC regimens tested and with 4 mg/kg IV.

CRP

FIG. 2 displays the CRP profile following both SC and IV dose regimens in RA patients. 162 mg SC QW has the most rapid and sustained reduction of CRP levels of the SC dose regimens tested. Among lower SC regimens, CRP normalization is reached with 162 mg SC Q2W (please note that in MRA227, patients were given a single dose (SD) on week 0 followed by multiple dosing starting on week 3; dose was switched from 81 mg Q2W to QW at week 9, see FIG. 2). Lower SC regimens (81 mg QW/Q2W) did not seem to result in CRP normalization. Therefore, 162 mg SC Q2W appears to be a lower SC dose option resulting in CRP normalization.

DAS28-ESR

FIG. 3 displays the DAS28-ESR change following both SC and IV dose regimens in RA patients. Although DAS28-ESR data for SC regimens are limited, disease activity appears to decrease from baseline more rapidly and to a greater magnitude with 162 mg SC QW and 162 mg SC Q2W as compared to the other SC dose regimens tested (81 mg SC Q2W/QW) (FIG. 3). Compared with the response seen with 162 mg SC QW, 162 mg SC Q2W appears to be a lower SC dose option that achieves a DAS-ESR reduction from baseline.

PK & PK-Safety Relationship

Following multiple dose administration of TCZ to RA patients (MRA227), mean exposure (AUC, $C_{max}$, $C_{trough}$) is generally higher for the 4 & 8 mg/kg IV q4w dose than for 162 mg SC Q2W, with the exception of the trough level for 4 mg/kg IV q4w which is lower than the $C_{trough}$ observed with 162 mg SC Q2W (FIG. 4). The safety profile for the IV program has been extensively studied. Taken altogether and compared to 162 mg SC QW, the dose of 162 mg SC Q2W appears to be a lower SC dose option with an acceptable safety profile based on drug exposure.

Mean exposure (AUC, $C_{max}$, $C_{trough}$) is generally higher for the 4 & 8 mg/kg IV q4w dose than for 162 mg SC Q2W, with the exception of the $C_{trough}$ level for 4 mg/kg IV q4w which is lower than the $C_{trough}$ observed with 162 mg SC Q2W (FIG. 4). The safety profile for the IV program has been extensively studied. Taken altogether and compared to 162 mg SC QW, the dose of 162 mg SC Q2W appears to be a lower SC dose option with an acceptable safety profile based on drug exposure.

A single fixed dose (162 mg SC Q2W and 162 mg SC QW for escape therapy) will be administered for all RA patients, irrespective of body weight. This approach is supported by the fact that even after accounting for differences in exposure that could result from the full range of body weights on a fixed dose, the highest exposure defined by 3 parameters ($C_{max}$, $C_{trough}$ and AUC) with the 162 mg SC QW and Q2W dose regimen that has been observed or predicted is within the range that has been described for the IV program. Additionally this approach is supported by analyses of safety data (SAEs, AEs, laboratory) from the IV program. There is no apparent relationship between TCZ exposure and the occurrence of adverse events by class, especially for the most frequent adverse events in the "Infections and Infestations" and "Skin and Subcutaneous Tissue" classes. There is no apparent relationship between exposure of TCZ and the occurrence of serious adverse events. Except for neutropenia, there was no obvious increase in the frequency of laboratory abnormalities with increasing exposure; a slightly greater proportion of patients experienced Grade 3 or higher events of neutropenia in the higher TCZ exposure categories. In addition, there were single Grade 3 events of thrombocytopenia in the higher TCZ exposure categories. With respect to triglycerides, total cholesterol, and LDL-cholesterol levels, a slightly greater proportion of patients developed an increase in levels in the higher TCZ exposure categories. Taken altogether, these data suggest that use of a fixed dose regimen is acceptable. The effect of body weight on PK will be further assessed in this study.

Observed Safety Data from SC Studies in RA Patients (MRA227 and NP22623)

All (32) patients have enrolled in the MRA227 study and 29 patients have enrolled in the NP22623 study and received TCZ SC treatments including 81 mg QW/Q2W (MRA227 only), 162 mg Q2W and 162 mg QW. The subcutaneous administrations have been well tolerated in RA patients up to 33 weeks in the MRA227 study and up to 12 weeks in the NP22623 study. AEs observed following administration of SC doses in RA patients were generally consistent with the types and severity of those observed in the TCZ IV Phase 3 studies.

No deaths have been reported in the 4 SC TCZ studies. One SAE of pyelonephritis was reported in the 81 mg dose group. Limited data from NP22623 did not demonstrate different AE profiles between the 162 mg SC QW and Q2W dose groups. The magnitude of mean changes in laboratory values for both Japanese RA and Caucasian RA patients receiving SC TCZ resembled that of RA patients from the IV program. One Japanese RA patient who received 162 mg SC QW experienced neutropenia and the dose was reduced to 162 mg SC Q2W. One patient who received 81 mg SC Q2W experienced neutropenia and was not dosed further at week 11. The SC TCZ injection was generally well tolerated and not perceived as more painful than the SC placebo injection.

In study MRA227, none of the patients from the 162 mg QW group tested positive for anti-TCZ antibodies. Four patients from the lower dose group were anti-TCZ antibody positive (all from the 81 mg QW/Q2W dose group, one patient prior to TCZ administration); five patients were anti-TCZ IgE antibody positive (3 patients in the 81 mg Q2W/QW dose group and 2 patients in the 162 mg Q2W dose group). Among those with positive antibody tests, the patient positive at baseline experienced grade 1 eczema which was considered as unrelated (food allergy), one patient experienced grade 1 urticaria, and another patient experienced injection site bruising. No other AEs were reported in the "Skin and Subcutaneous Tissue" and "General Disorders and administration site conditions" classes in patients who tested positive for anti-TCZ antibodies. In NP22623, three patients tested anti-TCZ antibody positive with the screening assay, but none were positive with the confirmatory assay.

SUMMARY

Previously, TCZ 162 mg SC weekly (QW) was selected as a comparator dose regimen for TCZ 8 mg/kg IV q4w. Of the remaining SC doses tested, observed PK, PD, efficacy, and safety data from RA patients demonstrate that 162 mg SC every other week (Q2W) is an appropriate lower SC dose option for this study NA25220B.

At the baseline visit, patients will be randomized in a 2:1 ratio to receive either TCZ 162 mg SC Q2W (group A), or placebo SC Q2W (group B) for 24 weeks. The primary analysis will occur when all patients have reached Week 24.

Starting from Week 24, all patients will receive open-label treatment with TCZ 162 mg SC Q2W and no patient will receive placebo injection.

In addition, at the Week 24 visit, patients will be re-randomized for the open-label period as follows:
Group A: patients will be re-randomized at a 1:1 ratio to receive TCZ 162 mg SC every other week, either using autoinjector (AI) (group A1) or pre-filled syringe (PFS) (group A2).
Group B: patients will be re-randomized at a 1:1 ratio to receive TCZ 162 mg SC every other week, either using AI (group B1) or PFS (group B2).

Prior to the first dose of double-blind study medication (baseline visit), patient-reported outcomes and efficacy assessments should be performed within 24 hours (up to 72 hours will be allowed when necessary).

Efficacy parameters will be assessed at baseline, Week 2, Week 4 and then every 4 weeks up to Week 40 and then Week 48, 60, 72, 84 and 96 or early withdraw (WD) visit. Separate radiographs of each hand and foot will be taken at screening, Weeks 24 and 48.

Treatment Groups

The individual treatment groups are:
Group A: ~400 patients, TCZ 162 mg SC Q2W using PFS in the 24-week double-blind period, and then re-randomized to:
Group A1: ~200 patients, TCZ 162 mg SC q2w, using AI in the open-label period.
Group A2: ~200 patients, TCZ 162 mg SC q2w, using PFS in the open-label period.
Group B: ~200 patients, placebo SC Q2W using PFS in the 24-week double-blind period, and then re-randomized to:
Group B1: ~100 patients, TCZ 162 mg SC q2w, using AI in the open-label period.
Group B2: ~100 patients, TCZ 162 mg SC q2w, using PFS in the open-label period.

Patients, site personnel, and sponsor will not know whether TCZ or placebo is received in the double-blind period until all patients have completed the double-blind treatment period at Week 24 and all data for all patients up to that time point have been collected, locked and reported.

Each treatment group is required to receive background therapy with non-biological DMARD(s) that are initiated and at a stable dose 8 weeks prior to the first dosing of TCZ. Dosages of non-biological DMARDs, NSAIDs and corticosteroids should remain stable during the core study period (up to Week 248). Dosage of NSAIDs should remain stable up to week 24. However, reductions in these treatments will be allowed if required for safety reasons. Patients may also receive intra-articular steroids and/or an increase in oral corticosteroid dosage (maximum dose of 10 mg total dose/day).

Primary and Secondary Study Endpoints
Primary Endpoints

The primary endpoint is the proportion of patients with an ACR20 response at Week 24.

Secondary Endpoints

Excluding the change from baseline in van der Heijde modified Sharp radiographic score to Week 48 all secondary endpoints will be formally tested. To ensure the alpha level is maintained at 5%, the secondary endpoints will be tested using a pre-specified fixed sequence method. This method will be described in detail in the DAP.

1. Change from baseline* in the van der Heijde modified Sharp radiographic score to Week 24.
2. Change from baseline* in the van der Heijde modified Sharp radiographic score to Week 48.
3. Proportion of Patients with ACR50 responses at Week 24.
4. Proportion of Patients with ACR70 responses at Week 24.
5. Mean changes from baseline in the individual parameters of the ACR core set Week 24.
6. Major clinical response (ACR70 response maintained over 24 weeks of treatment) at Week 48.
7. Change in Disease Activity Score (DAS28) from baseline at Week 24.
8. Change from baseline in HAQ-DI at Week 24.
9. Proportion of Patients classified as Categorical DAS28 responders (EULAR response) at Week 24.
10. Proportion of patients achieving DAS28 low disease activity (DAS≤3.2) at Week 24.
11. Proportion of patients with change from baseline in HAQ≥0.3 at Week 24.
12. Proportion of patients with DAS28 score <2.6 (DAS remission) at Week 24.
13. Change in SF-36 subscale and summary scores from baseline to Week 24.
14. Time to onset of ACR20, 50, 70 by treatment group.
15. Change from baseline in haemoglobin level at Week 24.
The assessment taken prior to receiving first dose of study medication is considered baseline.

Radiographic Assessments

Separate radiographs of each hand (posterior-anterior, PA) and each foot (anterior-posterior, AP) will be taken at screening, Weeks 24 and 48. Radiographs will be assessed using van der Heijde modified method according to Sharp (van der Heijde, D. "How to read radiographs according to the Sharp/van der Heijde method." *J Rheumatol* 27: 261-263 (2000)).

All non-escape patients will receive TCZ SC Q2W starting from week 24. The radiographic analysis at Week 48 will compare patients randomized at baseline to placebo with patients randomized to TCZ SC Q2W, both groups receiving active drug starting from week 24. It will be explored whether the rate of progression of structural damage differs between both periods. This will be particularly relevant in the group of patients randomized to placebo at baseline.

Treatment with SC anti-IL-6R antibody (TCZ), in combination with DMARDs, as disclosed in this example is anticipated to be effective (based on Week 24 ACR20 data) and safe (with respect to AEs and laboratory assessments). Moreover, treatment with SC anti-IL-6R antibody (TCZ) can inhibit progression of structural joint damage at Week 24 and Week 48, and improve physical function in RA patients.

Example 4

Anti-IL-6R Antibody Composition Including Hyaluronidase Enzyme

This example describes the development of a stable pharmaceutical formulation including anti-IL-6R antibody (tocilizumab) and hyaluronidase enzyme (recombinant human PH20, rHuPH20).

Drug Substance

The anti-IL-6R antibody tocilizumab (see, e.g. U.S. Pat. No. 5,795,965) is an active ingredient in the formulation, used to treat RA or other IL-6-mediated disorders.

The recombinant human PH20 (rHuPH20), see, e.g. U.S. Pat. No. 7,767,429, is included to increase the dispersion area of the SC injected TCZ thereby allowing the SC injection of volumes greater than 2 mL as well as potentially increasing the bioavailability compared to the SC formulation without hyaluronidase (see Example 5).

Selection of pH/Buffer

A pH for stabilizing tocilizumab SC vials 162 mg was found to be approximately pH 6.0. The pH of 6.0±0.5 was therefore selected for the current formulation. L-histidine/L-histidine monohydrochloride is added to the formulation as buffering agent at a concentration of 20 mM, which is within the normal concentration range of 10-100 mM for parenteral buffers. The pH of approximately 6.0 achieved by using a predefined ratio of buffer salt and base and optionally, sodium hydroxide or hydrochloric acid can be used for pH adjustment.

Stabilizing Agents

Polysorbate 80 is added at a concentration of 0.2 mg/mL as a stabilizing agent to prevent potential mechanical stress (agitation)-induced and potential freeze and thaw-induced instabilization of the protein.

L-arginine hydrochloride and L-methionine are added at a concentration of 100 mM and 30 mM as stabilizing agents to prevent potential thermal stress-induced instabilization of the protein.

Formulation Development

The goal was to develop a stable and sterile liquid solution for subcutaneous injection of tocilizumab.

Due to the higher concentration of tocilizumab, 180 mg/mL versus 20 mg/mL used in the IV formulation, the SC formulation was developed with regard to the effect of protein concentration on the ejection force and the viscosity on a standard syringe. Volume of subcutaneous injection is ideally 1 mL or less, so that high concentration of protein is needed in drug product. On the other hand, high viscosity which is caused by high concentration of protein, increase injection force. From correlation between protein concentration and viscosity, the target tocilizumab concentration was 180 mg/mL.

Table 2 compares exemplary tocilizumab SC-formulations with a tocilizumab IV-formulation. The lyophilized SC-formulation with 114.3 mg/mL TCZ was used in a previous human pharmacokinetic clinical study conducted in France using 20 healthy volunteers. The purpose of this early study was to investigate the absolute bioavailability and tolerability of the subcutaneous route of administration.

TABLE 2

Comparison of anti-IL-6R Antibody Formulations

| Ingredient | Tocilizumab IV-formulation[a] | Tocilizumab SC Lyo Vials 80 mg Reconstitute Solution[c] | Tocilizumab SC Vials 162 mg/0.9 mL for phase 1 & 2 | Tocilizumab SC Syringes 162 mg/0.9 mL for phase 3 | Tocilizumab Co-formulated with rHuPH20 | Function |
|---|---|---|---|---|---|---|
| Tocilizumab concentration (Drug substance process) | 20 mg/mL | 114.3 mg/mL | 180 mg/mL | 180 mg/mL | 180 mg/mL | Active ingredient |
| pH buffer | Phosphate[b] | Phosphate[d] | Histidine[e] | Histidine[e] | Histidine[e] | pH buffer |
| Polysorbate 80 | 0.5 mg/mL | 1.4 mg/mL | 0.2 mg/mL | 0.2 mg/mL | 0.2 mg/mL | Stabilizing agent |
| Sucrose | 50 mg/mL | 100 mg/mL | — | — | — | Osmolality adjustment Bulking Agent |
| L-Arginine | — | — | — | 0.147 mg/mL[f] | — | Stabilizing agent |
| L-Arginine hydrochloride | — | — | 21.1 mg/mL[f] | 20.9 mg/mL[f] | 21.1 mg/mL[f] | Stabilizing agent |
| L-Methionine | — | — | 4.48 mg/mL[g] | 4.48 mg/mL[g] | 4.48 mg/mL[g] | Stabilizing agent |
| Total volume adjusted with Water for Injection | q.s.[h] | q.s.[h] | q.s.[h] | q.s.[h] | q.s.[h] | Diluent |
| Hyaluronidase (rHuPH20) | — | — | — | — | 1,500 U/mL | Increase dispersion and/or bioavailability |

[a] Currently available Tocilizumab IV-strengths are: Vials 80 mg/4 mL, Vials 200 mg/10 mL and Vials 400 mg/20 mL with different fill volume of the same formulation with the same concentration of the drug substance.
[b] pH of solution 6.5 and 15 mmol/L for phosphate buffer
[c] Each concentration of ingredient is calculated from actual reconstituted volume (0.7 mL).
[d] pH of solution 7.0 and 42.9 mmol/L for phosphate buffer
[e] pH of solution 6.0 and 20 mmol/L for histidine buffer
[f] corresponds to a concentration of 100 mmol/L L-Arginine hydrochloride
[g] corresponds to a concentration of 30 mmol/L L-Methionine
[h] q.s. = quantum satis (as much as may suffice)

Overages

No concentration overages are used in the formulation.

Formulation with Hyaluronidase Enzyme

The following table summarizes the ingredients and concentrations thereof in an exemplary formulation including both anti-IL-6R antibody (TCZ) and hyaluronidase (rHuPH20):

TABLE 3

| SC Formulation | |
|---|---|
| Ingredient | Concentration |
| Tocilizumab | 180 mg/mL |
| rHuPH20 | 1,500 U/mL |
| Polysorbate 80 | 0.2 mg/mL |
| L-Arginine hydrochloride | 21.1 mg/mL[a] |
| L-Methionine | 4.5 mg/mL[b] |
| L-Histidine | 1.5 mg q.s.[c,d] |
| L-Histidine monohydrochloride | 2.1 mg q.s.[c,d] |
| Total volume adjusted with Water for Injection (WFI) | 1 mL q.s.[d] |

[a] corresponds to a concentration of 100 mmol/L L-arginine hydrochloride
[b] corresponds to a concentration of 30 mmol/L L-methionine
[c] pH of solution 6.0 and 20 mmol/L for histidine buffer; sodium hydroxide or dilute hydrochloric acid can optionally be used for pH adjustment.
[d] q.s = quantum satis (as much as may suffice)
(L-Histidine, L-Histidine monohydrochloride, and WFI are potential amounts to achieve pH 6.0)

Physicochemical and Biological Properties

The formulation demonstrates good stability at the recommended storage condition of 2-8° C. when protected from light.

PK Studies

Two non-clinical PK studies with the TCZ SC formulation including hyaluronidase have been conducted; one in mini-pigs, and one in Cynomolgus monkeys (Table 4):

The study in Cynomolgus monkey provided information about repeat-dose toxicity with the TCZ SC formulation in the same species (Table 4). Plasma levels of TCZ following a single dose of 50 mg/kg of the TCZ SC formulation were assessed. Results demonstrate that after SC administration maximum serum concentrations of TCZ (mean±SD: 822±230 µg/mL) were reached after 48 hours (median). The results of this study are available except for the animals which are currently in the treatment-free recovery period. Subcutaneous weekly dosing of tocilizumab in a formulation containing recombinant hyaluronidase (rHuPH20) to Cynomolgus monkeys at 100 mg/kg for 13 weeks was systemically and locally well tolerated, without any test item induced finding. The no adverse effect limit (NOAEL) was considered to be at the dose level of 100 mg/kg.

Example 5

Clinical Study with SC Formulation Including Anti-IL-6R Antibody and Haluronidase Enzyme Tocilizumab (TCZ) is a recombinant humanized, IgG1 monoclonal antibody directed against the soluble and membrane-bound interleukin 6 receptor (IL-6R). Hyaluronidase enzyme (rHuPH20) is used to facilitate injection of subcutaneous (SC) formulations by cleaving the hyaluronic acid chain in the SC interstitial matrix at the injection site. The aim of the study was to evaluate pharmacokinetic (PK), pharmacodynamic (PD), and safety following single ascending doses of TCZ with rHuPH20.

Materials and Methods

This was a phase 1 ascending dose (162 mg TCZ alone, 162 mg, 324 mg, and 648 mg TCZ+rHuPH20) study in healthy subjects. The formulation of Example 4, Table 3 was used in this study.

TABLE 4

| | | | | PK studies | | | | |
|---|---|---|---|---|---|---|---|---|
| | | | TCZ | rHuPH20 Dose in SC Formulation | | | | |
| Study type | Species | Dosing regimen | dose (mg) | mg/mL | U/mL | Volume (mL) | Total Units | Endpoints |
| PK (non GLP) | Mini-pig | TCZ SC single dose | 180 | 0 | 0 | 1.0 | 0 | TCZ in plasma— Absolute bioavailability |
| | | | 180 | 0.02 | 2000 | 1.0 | 2000 | |
| | | | 180 | 0.06 | 6000 | 1.0 | 6000 | |
| | | | 540 | 0.06 | 6000 | 3.0 | 18000 | |
| | | TCZ IV** single dose | 20* | 0 | 0 | ca. 1.0 | 0 | |
| PK (non-GLP) | Cynomolgus monkey | TCZ SC single Dose | 50* | 0.06 | 6000 | ca. 3 | 1800 | TCZ in plasma |

*dose level in mg/kg
**IV administration of TCZ to allow calculation of absolute bioavailability.

The mini-pig was chosen for rHuPH20 dose selection because its skin and the texture of SC tissue are considered to be similar to those of humans. The mini-pig study utilized two SC dose levels of TCZ formulations with various concentrations of rHuPH20 as well as an IV dosing arm with TCZ alone (Table 4) to allow estimation of absolute bioavailability/fraction absorbed. Study results indicated a more rapid absorption of SC administered TCZ from rHuPH20 containing formulations. Thus, median time to maximum plasma levels of TCZ was shortened from 48 hours without rHuPH20 to 24 hours for all rHuPH20 containing formulations. The fraction absorbed of SC administered TCZ was estimated at around 80% for all dose groups.

The objectives of the study were:

Primary Objective:

1. To investigate the effect of rHuPH20 on the exposure of different SC doses of TCZ.

Secondary Objectives:

1. To explore the safety and tolerability of a single SC dose of TCZ containing rHuPH20 in healthy volunteers.
2. To investigate the PK/pharmacodynamic (PD) relationship of TCZ (with or without rHuPH20) following SC administration by measuring IL-6, sIL-6R, and C-reactive protein (CRP) in healthy volunteers.

Overall Study Design

This was a phase 1, single-dose, open-label, parallel group for Cohorts 1 and 2 and sequential for the rest of the cohorts, single-center study in healthy males and females 18 to 65 years of age, inclusive, of non-child-bearing potential. Table 5 provides an overview of the study design.

TABLE 5

Overview of Study Design

| Screening | Assessments | Study drug administration/ assessments | Assessments continued | Safety follow-up |
|---|---|---|---|---|
| Days −28 to −2 | Day −1 | Day 1 Single dose of study drug administration In-clinic stay from day −1 (evening) to day 2 (morning) | Days 2 to 36 | Between days 40 and 43 |

Eligible subjects were assigned to one of four cohorts listed in Table 6. The concentration of rHuPH20 used in this study was guided by data from the mini-pig study in Example 4 above in which TCZ was administered SC in the presence and in the absence of either 2,000 or 6,000 U/mL (nominal concentrations) of rHuPH20. Results demonstrated a more rapid absorption of TCZ administered SC from rHuPH20 containing TCZ formulations. This effect on the absorption rate of TCZ was comparable with both rHuPH20 concentrations. Analytical quantification of the dosing solution revealed an actual rHuPH20 concentration of 1,356 U/mL (instead of the nominal 2,000 U/mL). Therefore, a rHuPH20 concentration of 1,500 U/mL was selected for the proposed clinical study.

TABLE 6

TCZ Dosage and Schedule

| Cohort | IMP |
|---|---|
| 1 | TCZ (180 mg/mL) SC formulation single dose of 0.9 mL corresponding to a dose of TCZ 162 mg TCZ |
| 2 | TCZ (180 mg/mL)/rHuPH20 (1,500 U/mL) SC formulation, single dose of 0.9 mL corresponding to a dose of 162 mg TCZ and 1,350 U rHuPH20 |
| 3 | TCZ (180 mg/mL)/rHuPH20 (1,500 U/mL) SC formulation, single dose of 3.6 mL corresponding to a dose of 648 mg TCZ and 5,400 U rHuPH20 |
| 4 | TCZ (180 mg/mL)/rHuPH20 (1,500 U/mL) SC formulation, single dose of 1.8 mL corresponding to a dose of 324 mg TCZ and 2,700 U rHuPH20 |

The study consisted of a screening period (days −28 to −2), an in-clinic period (days −1 evening to 2 morning) with a single dose of study drug given on day 1 and a follow-up period (between days 40 and 43).

Eligible subjects were admitted to the clinical research unit on day −1 and predose assessments and procedures were performed. After a minimum fast of 4 hours, blood and urine samples were taken. After a light, standardized breakfast on the morning of day 1, subjects received their TCZ SC injection in the right or left anterior thigh (midway between the anterior iliac crest and the cephalad border of the patella). Start and end time of each SC injection was recorded and individual injection sites were photographed before and after injection.

After placement of the injection device, but before study drug injection, subjects had their pain assessed according to a 100 mm horizontal visual analogue scale (VAS) and a categorical 6-point pain self-assessment.

Subjects remained in the unit until the 24-hour PK assessments were complete and returned for PK and safety assessments as specified. Blood samples were drawn pre-dose and at 2, 8, 12, 24 and 36 hours post-dose for the analysis of serum TCZ levels. Additional blood samples were collected on days 3, 4, 5, 8, 11, 15, 18, 22, 29, 36 and at follow up. Blood samples for assessments of IL-6, sIL-6R, and CRP were drawn at the same time points as samples for the PK analyses.

Subjects returned to the clinic between days 40 and 43 for follow-up procedures including a physical examination, three serial 12-lead ECGs, vital signs and clinical laboratory tests.

Safety (clinical laboratory tests and vital signs) and PK/PD assessments were performed at regular intervals during the study. Spontaneous adverse events were recorded throughout the study. Subjects remained in the unit until the 24-hour PK assessments were complete. Subjects returned for PK and safety assessments on specified days afterwards.

PK and PD samples were collected intensively. PK and PD parameters were estimated with non-compartmental methods. A one way ANOVA was used to assess the effect of rHuPH20 on TCZ exposure. Safety and tolerability was monitored throughout the study.

Results

Results of this study are depicted in FIGS. 8-13.
Pharmacodynamic Results:
CRP:

Following administration of SC TCZ across all cohorts, mean CRP values decreased rapidly and reached a nadir at nominal times 168 and 240 hours in Cohorts 1 and 2 and at 336 hours in Cohorts 3 and 4, although by the nominal time 168 hours nadir was approximately reached in all cohorts. Thereafter, mean CRP values increased toward baseline values by nominal time 504 hours in Cohorts 1 and 2 and by 672 hours in Cohort 4. Mean CRP values remained suppressed through 672 hour time point in Cohort 3, however the unscheduled follow-up sample revealed mean values which returned toward baseline. Cohorts 1 and 2 revealed a similar change from baseline in mean CRP values while in Cohort 4 CRP values revealed a delay in time to return to baseline. In Cohort 3 mean change from baseline values remained below baseline. A dose dependent effect on mean CRP noncompartmental parameters was observed with a dose dependent decrease in mean $AUC_{0-D29}$ for CRP observed across cohorts. Dose dependent changes in CRP $T_{min}$ were also observed where a delay in mean $T_{min}$ was observed with increasing dose. See FIG. 10.

IL-6:

Following administration of SC TCZ with and without rHuPH20, mean IL-6 serum concentrations increased rapidly in all four cohorts and subsequently declined gradually over time. In Cohorts 1 and 2, mean IL-6 concentrations reached approximate baseline levels by nominal sample time of 504 hours while in Cohort 4 mean IL-6 serum concentrations reached approximately baseline values by the follow-up sample on days 40-43. In Cohort 3, mean IL-6 values were elevated through the nominal time 672 hours, but concentrations returned to approximate baseline values at the unscheduled follow-up sample. See FIG. 11.

sIL-6R:

Following administration of SC TCZ with and without rHuPH20, mean sIL-6R serum concentration increased rapidly in all cohorts. Following maximal concentrations reached at nominal sampling time 240 hours in Cohorts 1 and 2, mean sIL-6R concentrations subsequently declined to approximately baseline levels by nominal time 672 hours. In Cohort 4, mean sIL-6R serum concentrations decreased following maximal concentration at nominal time 408 hours toward baseline values by the follow-up sample on days 40-43. In Cohort 3, mean sIL-6R serum concentrations increased rapidly following TCZ administrations and continued to increase across all sampling points reaching an observed maximal concentration at the sampling time of 672 hours. See FIG. 12.

For IL-6 and sIL-6R noncompartmental parameters, mean $AUC_{0-D29}$ increased with increasing dose across cohorts. Mean $C_{max}$ revealed a similar dose dependent increase. Observed time to maximum concentration ($T_{max}$) was prolonged with increasing dose.

In comparing the effect of rHuPH20 on PD response between Cohort 1 (162 mg TCZ) and Cohort 2 (162 mg TCZ/1350U rHuPH20), the concentration-time profiles were similar between the two groups for all three PD parameters (CRP, IL-6, and sIL-6R). Mean PD (CRP, IL-6, and sIL-6R) $AUC_{0-D29}$ parameters were similar between Cohorts 1 and 2 with $AUC_{0-D29}$ ratios of 99.6%, 100%, and 97.4% for CRP, IL-6, and sIL-6R, respectively.

Pharmacokinetic Results:

Results from Cohorts 1 and 2 (162 mg TCZ with and without PH20) indicate a trend towards an earlier $T_{max}$ and slightly higher exposure (GMR [90% confidence intervals] for $C_{max}$ and $AUC_{0-inf}$ were 1.45 [1.24-1.70] and 1.20 [1.00-1.44], respectively) in the presence of rHuPH20 while TCZ serum concentrations in the elimination phase were superimposable for the two formulations. With the addition of rHuPH20 in Cohort 2, there was a clear trend towards reduced variability (CV %) in the PK parameters of TCZ (17.4 vs. 32.4 for $C_{max}$ and 16.4 vs. 42.0 $AUC_{0-inf}$ with and without rHuPH20, respectively).

In Cohort 3 following administration of 648 mg TCZ/PH20, mean $C_{max}$ and $AUC_{0-inf}$ of TCZ were approximately 6.95- and 12.55-fold higher than in Cohort 1 (162 mg TCZ), while the total dose administered was only 4-fold higher, reflecting the non-dose proportionality in the PK of TCZ. The unscheduled follow-up sample taken for subjects in Cohort 3 (mean actual time 1909±66.1 hours) revealed TCZ serum concentrations below the limit of quantification for all subjects indicating the complete elimination of the single TCZ SC dose.

In Cohort 4 following administration of 324 mg TCZ/PH20, mean $C_{max}$ and $AUC_{0-inf}$ of TCZ were approximately 3.85- and 4.44-fold higher than in Cohort 1 (162 mg TCZ), while the total dose administered was only 2-fold higher.

Plasma rHuPH20 concentrations were below the limit of quantification for all sampling points in all subjects indicating the use of the enzyme as a local permeation enhancer for the co-administered drug does not result in quantifiable systemic exposures of the enzyme.

Pharmacokinetic/Pharmacodynamic Relationships:

sIL-6R and TCZ:

The sIL-6R concentrations reached $C_{max}$ after TCZ reached its $C_{max}$ for all 4 cohorts, with a delayed increase in sIL-6R levels as the TCZ concentration increased creating a counter-clockwise hysteresis relationship. The TCZ $C_{max}$ was reached at times ranging from 36 to 96 hours after administration of TCZ across all cohorts, while sIL-6R reached $C_{max}$ at nominal time 240 hours for Cohorts 1 and 2, nominal time 672 hours for Cohort 3, and nominal time 408 hours for Cohort 4.

C-Reactive Protein and TCZ:

As with sIL-6R, TCZ administration resulted in a delayed decrease of CRP, ie, the CRP nadir was reached after the $C_{max}$ of TCZ. The CRP nadir was reached at nominal times 168 and 240 hours in Cohorts 1 and 2 and by 336 hours in Cohorts 3 and 4 while the TCZ $C_{max}$ occurred at times ranging from 36 to 96 hours after administration of TCZ across all cohorts, creating a clockwise hysteresis relationship Safety Results:

Sixty-one of the 68 reported adverse events were considered by the investigator to be possibly or remotely related to treatment with the study drug. Most were injection site adverse events, which were reported only by subjects who received TCZ with rHuPH20. There were no deaths, no serious adverse events, and no subjects withdrew from the study due to an adverse event. There did not appear to be a relationship between the number of subjects reporting adverse events, the presence or absence of rHuPH20, or the dose of TCZ.

With the exception of mean white blood cell counts and neutrophil counts, mean hematology parameters remained in the normal range throughout the study, as did mean total bilirubin, ALAT, and ASAT concentrations. Mean white blood cell counts and neutrophil counts were back within reference ranges at the end of the study. Low neutrophil count was also the most common marked laboratory abnormality reported during the study, reported by a total of 30 subjects across all treatment groups. Eight of the subjects with markedly low neutrophil counts also reported infections, which resolved with no sequelae. ECG readings and vital signs were normal throughout the study for most subjects. There were no clinically relevant changes in serum IgE, IgG, IgM, and IgA levels. Neutralizing anti-TCZ antibodies were confirmed in two subjects receiving 648 mg TCZ/rHuPH20. No subjects developed neutralizing anti-rHuPH20 antibodies. The SC injections were well tolerated in all cohorts, as evaluated by the Visual Analog Scale and patient categorical self-assessment.

CONCLUSIONS

Pharmacokinetic and Pharmacodynamic Conclusions
  Administration of TCZ with rHuPH20 resulted in a slightly increased exposure with geometric mean ratios (90% confidence intervals) for $AUC_{0-inf}$ and $C_{max}$ of 1.20 (1.00-1.44) and 1.45 (1.24-1.70), respectively, for Cohort 2 (162 mg TCZ/rHuPH20) to Cohort 1 (162 mg TCZ) supporting the hypothesis that rHuPH20 acts as a local permeation enhancer.
  A clear trend towards lower PK variability in the presence of rHuPH20 was observed.
  A four-fold increase in administered TCZ dose in Cohort 3 (648 mg TCZ/PH20) resulted in 12.55-fold higher $AUC_{0-inf}$ and 6.96-fold higher $C_{max}$ with 648 mg TCZ/PH20 compared to 162 mg TCZ in Cohort 1
  A two fold increase in administered TCZ dose in Cohort 4 (324 mg TCZ/PH20) resulted in 4.44-fold higher $AUC_{0-inf}$ and 3.85-fold higher $C_{max}$ with 324 mg TCZ/PH20 compared to 162 mg TCZ in Cohort 1.
  The single SC TCZ doses assessed in Cohort 4 (324 mg) provided mean $AUC_{0-inf}$ of 10800±3220 μg·hr/mL and CD29 of 1.6±2.4 μg/mL and provided a $C_{max}$ of 43.8±12.4 μg/mL.

The single SC TCZ doses assessed in Cohort 3 (648 mg) provided mean $AUC_{0-inf}$ of 29900±5280 μg·hr/mL and CD29 of 12.6±5.0 μg/mL and provided a $C_{max}$ of 77.8±14.5 μg/mL.

The impact on the PD markers sIL-6R, IL-6 and CRP are comparable for SC formulations containing 162 mg TCZ with and without rHuPH20. Dose dependent changes in PD markers were observed with increased doses from 162 mg to 648 mg TCZ/rHuPH20.

Safety Conclusions

Serious adverse events were not reported with SC doses of TCZ with or without rHuPH20.

Tocilizumab-treatment was associated with a decrease in neutrophils within 2 to 5 days of treatment. Mean neutrophil counts returned to baseline from day 15 to follow-up in a dose dependent manner Most other laboratory parameters ECGs, immunoglobulin levels and vital signs recordings remained within the normal range throughout the study.

Two subjects developed neutralizing anti-TCZ antibodies

No subjects developed neutralizing anti-rHuPH20 antibodies.

SC injections were well tolerated based on the Visual Analog Scale and subject categorical self-assessment.

Example 6

SQ Administered Anti-IL-6R Antibody for sJIA

This example describes the use of subcutaneously administered anti-IL-6R antibody (TCZ) to treat systemic juvenile idiopathic arthritis (sJIA). A TCZ formulation with 180 mg/mL TCZ and no hyaluronidase (see Table 2 in Example 4) is subcutaneously administered in this example.

This is a phase 1b open label multi-center study to investigate pharmacokinetics, pharmacodynamics, efficacy and safety of tocilizumab following subcutaneous administration in patients with active sJIA. Patients to be treated in this study will be children age 2 up to and including age 17 sJIA≥6 months persistent activity who have had an inadequate clinical response to NSAIDs and corticosteroids (CS) due to toxicity or lack of efficacy will be treated herein.

Figure 23A:
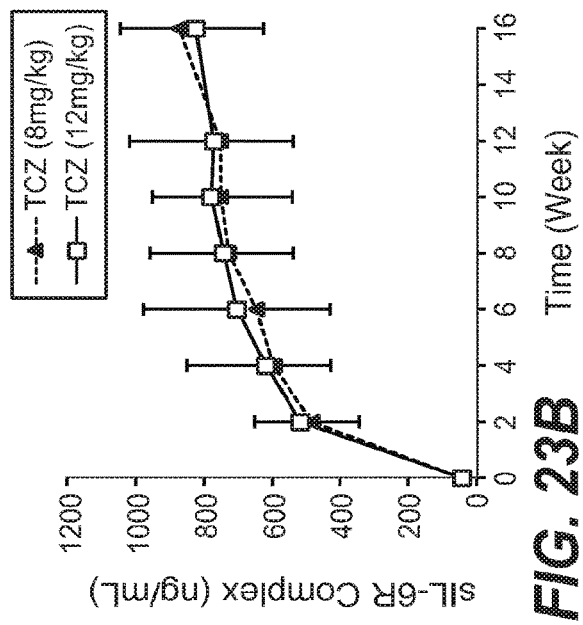
Figure 23B:
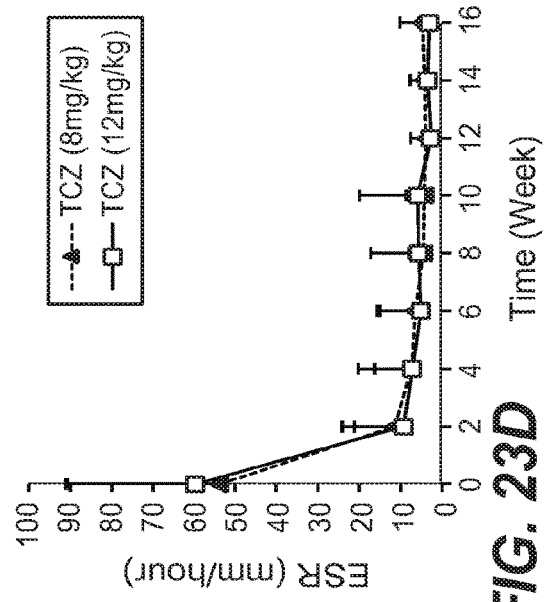
Figure 23C:
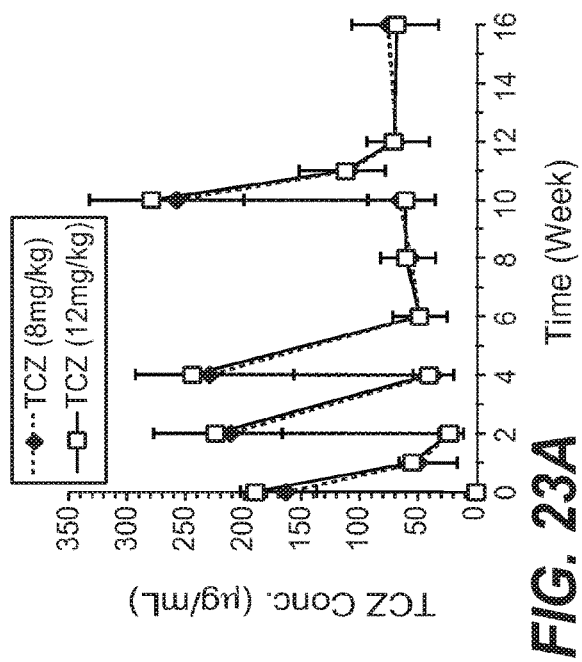
Figure 23D:
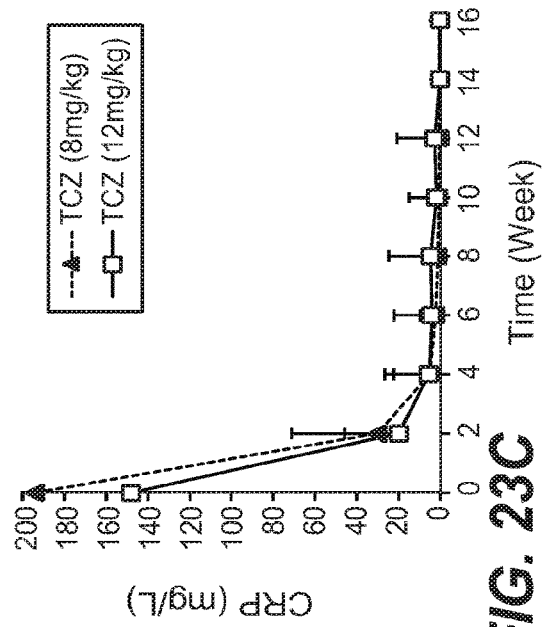

In WA18221 study, TCZ was given at 12 mg/kg in patients with BW<30 kg and 8 mg/kg in patients with BW≥30 kg every 2 weeks for 12 weeks. Comparable PK exposures were achieved for two body weight groups (FIG. 23A). Comparable sIL-6R profiles (FIG. 23B), CRP normalization pattern (FIG. 23C), and ESR profile (FIG. 23D) were observed for two BW groups. The comparable PK-PD profiles from WA18221 study resulted in acceptable efficacy and safety across the entire body weight range. Of all TCZ treated patients, 85.3% patients met primary endpoint of a JIA ACR30 response and absence of fever at Week 12 in contrast to 24.3% of the placebo patients demonstrating a statistically significant difference (p<0.0001). At week 12, JIA ACR 30, 50, 70 and 90 responses were 90.7%, 85.3%, 70.7% and 37.7%, respectively, compared to 24.3%, 10.8%, 8.1% and 5.4% from placebo group, respectively.

To further examine if dose was adequate in WA18221 study, the PK exposure-efficacy relationship was analysed by PK exposure quartiles. At week 12, $AUC_{2week}$ increased by 2.3-fold from quartile 1 (849±147 μs·day/ml) to quartile 4 (1,925±187 μg·day/ml) (Table 7). At week 52, Cmin in quartile 4 (108±12 μg/ml) was 3.6-fold greater than in quartile 1 (30±16 μg/ml) (Table 7). Although the study was not powered to compare efficacy in each of the 4 quartiles, proportions of patients who achieved JIA ACR30/50/70/90 responses appear comparable across 4 quartiles (Table 7), suggesting the exposures were at the plateau of the exposure-response curve. Limited data in each quartile did not show clear trend towards a higher incidence of AEs or serious AEs with higher TCZ exposure from quartile 1 to quartile 4 ($AUC_{2week}$, $C_{max}$ or $C_{min}$) (Table 8).

TABLE 7

Efficacy End Points by PK Quartile at Week 12 and Week 52 in Patients Assigned to TCZ at Baseline

| | Week 12 | | | |
|---|---|---|---|---|
| | Quartile 1 n = 19 | Quartile 2 n = 19 | Quartile 3 n = 19 | Quartile 4 n = 18 |
| $AUC_{2\ weeks}$ (μg · d/ml)$^2$ | 849 ± 147 | 1,178 ± 68.4 | 1,445 ± 105 | 1,925 ± 187 |
| JIA ACR30, n (%) | 16 (84.2) | 17 (89.5) | 18 (94.7) | 17 (94.4) |
| JIA ACR50, n (%) | 15 (78.9) | 16 (84.2) | 16 (84.2) | 16 (94.4) |
| JIA ACR70, n (%) | 9 (47.4) | 15 (78.9) | 14 (73.7) | 15 (83.3) |
| JIA ACR90, n (%) | 5 (26.3) | 7 (36.8) | 10 (52.6) | 16 (33.3) |

| | Week 52 | | | |
|---|---|---|---|---|
| | Quartile 1 n = 15 | Quartile 2 n = 14 | Quartile 3 n = 16 | Quartile 4 n = 13 |
| $C_{min}$ (μg/ml) | 30.0 ± 16.3 | 62.5 ± 4.1 | 81.9 ± 6.0 | 108 ± 12.0 |
| JIA ACR30, n (%) | 15 (100) | 14 (100) | 16 (100) | 13 (100) |
| JIA ACR50, n (%) | 13 (86.7) | 14 (100) | 16 (100) | 13 (100) |
| JIA ACR70, n (%) | 11 (73.3) | 11 (78.6) | 16 (100) | 13 (100) |
| JIA ACR90, n (%) | 8 (53.3) | 8 (57.1) | 13 (81.3) | 8 (61.5) |

Quartiles are defined as those patients falling within 0%-≤25%, >25%-≤50%, >50%-≤75%, and >75%-100% of exposures. Patients who were randomly assigned to placebo treatment in study part 1 are excluded. Patients who had missing PK samples at week 52 were excluded from the summary. Mean ± SD for $AUC_{2\ weeks}$ and $C_{min}$ are presented.

TABLE 8

Percentage of patients reporting adverse events by body system and preferred term to week 12 by $AUC_{2weeks}$ and to Week 52 by $C_{min}$ exposure quartiles

| Week 12 | Quartile 1[1] (n = 19) | Quartile 2[1] (n = 19) | Quartile 3[1] (n = 19) | Quartile 4[1] (n = 18) |
|---|---|---|---|---|
| $AUC_{2weeks}$ (μg · d/ml)$^2$ | 849 ± 147 | 1,178 ± 68 | 1,445 ± 105 | 1,925 ± 187 |
| All body systems[3] | 19 (100%) | 16 (84%) | 17 (865%) | 14 (78%) |
| Infections and infestation | 11 (58%) | 8 (42%) | 6 (32%) | 9 (50%) |
| Gastrointestinal disorders | 3 (16%) | 5 (26%) | 2 (11%) | 4 (22%) |
| Skin and subcutaneous tissue disorders | 4 (21%) | 1 (5%) | 3 (16%) | 4 (22%) |

TABLE 8-continued

Percentage of patients reporting adverse events by body system and preferred term to week 12 by $AUC_{2weeks}$ and to Week 52 by $C_{min}$ exposure quartiles

| | | | | |
|---|---|---|---|---|
| Nervous system disorders | 3 (16%) | 1 (5%) | 2 (11%) | 2 (11%) |
| Respiratory, thoracic, and mediastinal disorders | 3 (16%) | 1 (5%) | 2 (11%) | 1 (6%) |
| Serious adverse events | 3 (16%) | 0 (0%) | 0 (0%) | 0 (0%) |

| Week 52 | Quartile 1 (n = 15) | Quartile 2 (n = 14) | Quartile 3 (n = 16) | Quartile 4 (n = 13) |
|---|---|---|---|---|
| $C_{min}$ (µg · d/ml)[2,4] | 30 ± 16 | 63 ± 4 | 82 ± 6 | 108 ± 12 |
| All body systems[3] | 15 (100) | 14 (100) | 16 (100) | 11 (85) |
| Infections and Infestation | 10 (67) | 12 (86) | 15 (94) | 8 (62) |
| Gastrointestinal disorders | 7 (47) | 3 (21) | 5 (31) | 5 (39) |
| Skin and subcutaneous tissue disorders | 5 (33) | 3 (21) | 7 (44) | 7 (54) |
| Nervous system disorders | 4 (27) | 3 (21) | 3 (19) | 4 (31) |
| Respiratory, thoracic, and mediastinal disorders | 5 (33) | 2 (14) | 5 (31) | 6 (46) |
| Serious adverse events | 4 (27) | 1 (7) | 2 (13) | 1 (8) |

$AUC_{2weeks}$, area under the serum concentration-time profile over 2 weeks of the dosing interval at steady state;
$C_{min}$, minimum concentration of drug at week 52 (predose concentration).
Values are n (%) unless indicated otherwise. Patients who were assigned to placebo treatment in study part 1 were excluded. Patients who had missing PK samples at week 52 were excluded from the summary.
[1]Quartiles 1, 2, 3, and 4 are the first (0-<25%), second (>25-<50%), third (>50-<75%), and fourth (>75-100%) quartiles of individual exposure parameters as listed.
[2]Mean ± standard deviation, $AUC_{2weeks}$, and $C_{min}$ are presented.
[3]Total patients with at least one adverse event are included. Only the most frequent adverse events are presented.
[4]$C_{min}$ quartiles include only patients with nonmissing serum concentrations randomly assigned to TCZ at baseline In study WA18221, TCZ 12 mg/kg for patients <30 kg and 8 mg/kg for patients ≥30 kg, was given as an IV infusion every 2 weeks. The scatter plots of $C_{min}$ at steady state (Week 12) across body weight from 10.0-112.7 kg showed that TCZ exposures are independent of body weight (FIG. 15). The mean PK model predicted Cmin is summarized in Table 9.

TABLE 9

Model simulated PK exposures for various dose regimens

| Dose Regimen (route) | Body weight (sample size), kg | $AUC_{4week}$, µg · d/mL | $C_{min}$, µg/mL |
|---|---|---|---|
| 12 mg/kg Q2W (IV)[a] | <30 (38) | 2692 ± 852 (1116-4354) | 61 ± 26 (17-117) |
| 8 mg/kg IV Q2W (IV)[a] | ≥30 (37) | 2674 ± 818 (1144-4824) | 55 ± 21 (10.9-100) |
| All patients in WA18221[a] | All body weight | 2682 ± 830 (1116-4354) | 58 ± 23 (10.9-117) |
| 162 mg QW (SC)[b] | ≥30 (37) | 1810 ± 600 (816-3244) | 58 ± 20 (22-107) |
| 162 mg Q2W (SC)[b] | <30 (38) | 1398 ± 424 (798-2202) | 29 ± 13 (12-61) |
| 162 mg QW (SC)[b] | <30 (38) | 3092 ± 1020 (1416-5628) | 100 ± 35 (45-188) |
| 162 mg Q10D (SC)[b] | <30 (38) | 1784 ± 581 (825-3231) | 58 ± 22 (25-112) |

[a]Summary of PK parameters estimated by population analysis of data from study WA18221 follwing IV dosing; $AUC_{2week}$ was multiplied by 2 in order to compare with other SC regimens.
[b]Summary of simulated PK parameters for individual patients from Study WA18221 following SC dosing Available subcutaneous formulation is in a 1 mL prefilled syringe delivering 0.9 mL 162 mg TCZ per injection. Thus the SC dose in the present study is a flat dose regimen across wide BW range. The initial dose for the present study has been selected based on the modeling and simulation and explained below.

In study WA18221, pharmacokinetic profile following IV administration was described by a 2-compartment model with both a saturable (Michaelis-Menten elimination) and a non-saturable first order elimination pathway from central compartment. The PK disposition parameters were well characterized (total clearance (CL; L/d), volume of distribution of the central compartment (Vc; L), volume of distribution of the peripheral compartment (Vp; L), inter-compartmental clearance (Q; L/d), the Michaelis-Menten constant (Km; mg/L) and the maximum rate of the saturable elimination process (Vmax; mg/d)). In study NP22623, 162 mg TCZ was administered in the adult RA patients as either weekly (QW) and every other week (Q2W) dosing for 12 weeks in a total of 29 patients. Empirical modeling of the PK data from NP22623 provided subcutaneous absorption PK parameters (absorption rate constant Ka and bioavailability F) in RA patients. Under the assumption that these absorption PK parameters are similar to the absorption PK parameters in pediatric sJIA patients, and disposition PK parameters from WA18221 study are independent of the route of administration, the PK exposures were simulated for sJIA patients <30 kg and ≥30 kg following multiple dose administration up to a steady state. The simulated PK profiles for IV and SC administration are illustrated in FIG. 14. The PK model simulated $C_{min}$ values versus body weight are shown in FIGS. 15 to 18. Calculated PK parameters based on the simulated PK profiles are summarized in Table 9.

As expected, IV dosing regimen exhibited more fluctuation between the peak and the trough concentration during a dosing interval, whereas for SC dosing, fluctuation between peak and trough is much smaller (FIGS. 14A and 14B).

Based on PK simulation, for sJIA patients weighing ≥30 kg, 162 mg QW provided mean±SD $C_{min}$ (58±20) which is comparable to 58±23 from WA18221 study (Table 9). Individual Cmin data are also within 90% confidence limit from WA18221 study (FIGS. 16 to 18).

Based on PK simulation, for patients with BW<30 kg, 162 mg Q2W or 162 mg QW resulted in the mean±SD Cmin lower (29±13) or higher (100±35) than the average Cmin (58±23) from study WA18221, respectively. For 162 mg Q2W dosing, although all data are with min-max range from WA18221, 26% (10 of 38) Cmin values are below the lower 90% confidence bound from WA18221 study (FIG. 16). For 162 mg QW dosing, 21% (8 of 38) Cmin data are above the upper 90% confidence bound from WA18221 study (FIG. 17).

Based on PK model simulation, for patients with BW<30 kg, 162 mg SC injection every 10 days (Q10D) is predicted to provide mean±SD Cmin (58±22) being comparable to the data (58±23) from WA18221 study (Table 9). There are only 2 of 38 (5%) $C_{min}$ values outside of the 90% confidence bound (FIG. 18).

Thus, the following treatment protocols will be used:

Group 1:
Patients with body weight (BW)≥30 kg will receive 162 mg TCZ subcutaneous (SC) injections weekly (QW) for 14 weeks (13 doses). N=12

Group 2:
Patients with BW<30 kg will receive 162 mg TCZ SC injections every 10 days (Q10D) for 14 weeks (9 doses). N=12

The treatment period will last for 14 weeks. During the treatment period, stable NSAIDs and MTX will be continued unchanged throughout 14 weeks of the study. Oral steroid dose will remain stable up to 6 weeks from first dose of TCZ at baseline. Steroid tapering will be allowed from week 6 onwards at discretion of the investigator. For CS reduction, no more than 20% reduction per week is recommended. The investigator may adjust or discontinue concomitant MTX, CS and/or NSAIDs treatment according to standard of care for reasons of safety at any time. The follow-up visit will be performed at 2, 4 and 8 weeks after last SC dosing.

Pharmacokinetic parameters will include $C_{max}$, $C_{min}$, $T_{max}$, $T_{1/2}$, and $AUC_\tau$ at steady state.

Pharmacodynamic paramaters will include sIL-6R, CRP, and/or ESR concentration.

Efficacy will be evaluated by the following:
Proportion of patients with JIA ACR30/50/70/90 responses at Week 14 with and without absence of fever; and other efficacy parameters as appropriate.

It is anticipated that the anti-IL-6R antibody (TCZ) will be effective in sJIA patients with body weight ≥30 kg when administered as a fixed dose of 162 mg every week (QW) by SQ administration, e.g., for up to 14 weeks.

It is further anticipated that the anti-IL-6R antibody (TCZ) will be effective in sJIA patients with body weight <30 kg when administered as a fixed dose of 162 mg every 10±1 days (Q10D) by SQ administration, e.g., for up to 14 weeks. Alternative dosing regimens include 162 mg every week (QW) or every two weeks (Q2W).

Example 7

SQ Administered Anti-IL-6R Antibody for pCJIA

Anti-IL-6R antibody (TCZ) is subcutaneously administered to patients with polyarticular course juvenile idiopathic arthritis (pcJIA). The formulation with 180 mg/mL TCZ and no hyaluronidase disclosed in Table 2 in Example 4 is administered herein.

This is a phase Ib open label multi-center study to investigate pharmacokinetics, pharmacodynamics, efficacy and safety of tocilizumab following subcutaneous administration in patients with active pcJIA. Patients to be treated in this study will be children aged 2-17 years with at least 6 months active pcJIA (including either rheumatoid factor (RF)-positive or RF-negative polyarthritis subsets, or the extended oligoarticular JIA subset), with at least 5 joints with active arthritis (at least 3 of the active joints having limitation of motion) who have had an inadequate clinical response to methotrexate (MTX) due to lack of efficacy or toxicity, who are receiving standard of care, either with or without NSAIDs, low dose corticosteroids or concomitant MTX.

Up to 30% of patients enrolled in this study may have had previous treatment with a biologic disease modifying anti-rheumatic drug (biologic DMARD).

TCZ has been approved for treatment of pcJIA in Japan based on the phase 3 study MRA318JP conducted in Japanese patients. Objectives of the study were to determine the efficacy, safety, PK and PD of TCZ following 8 mg/kg TCZ infusion every 4 weeks for 12 weeks (3 infusions).

It was observed, that the clinical response, expressed as probability to reach a pcJIA50 or pcJIA70 score, was lower in children with a lower bodyweight compared to patients with a higher body weight. After 12 weeks of treatment with TCZ 8 mg/kg every 4 weeks: 88% of patients weighing <30 kg vs 100% of the patients weighing ≥30 kg reached a pcJIA50 score (FIG. 19A); and 38% of patients weighing <30 kg vs 80% of patients weighing ≥30 kg reached pcJIA70score (FIG. 19B).

This noticeable difference in JIA ACR response rate was associated with a visible trend towards lower systemic exposure ($AUC_{4week}$) to TCZ in subjects with lower body weight, particularly below a body weight of approximately 30 kg. In contrast, in patients with a body weight higher than 30 kg exposure appeared to be more or less independent of body weight (FIG. 20A). The PK of TCZ from MRA318 TCZ was described by a two-compartment disposition model with parallel first-order (linear CL) and Michaelis-Menten elimination (nonlinear or concentration-dependent CL) kinetics. For the dose of 8 mg/kg administered every 4 weeks, the contribution of nonlinear CL to AUC was small and had no relevant impact on $C_{max}$. The most pronounced impact of the concentration-dependent CL component on the PK of TCZ was observed for $C_{min}$. The $C_{min}$ values were close to the mean $K_M$ value of the nonlinear CL component. Thus, $C_{min}$ values were in a concentration range where small changes in serum TCZ concentrations result in a relative large change in nonlinear CL.

Figure 24A:
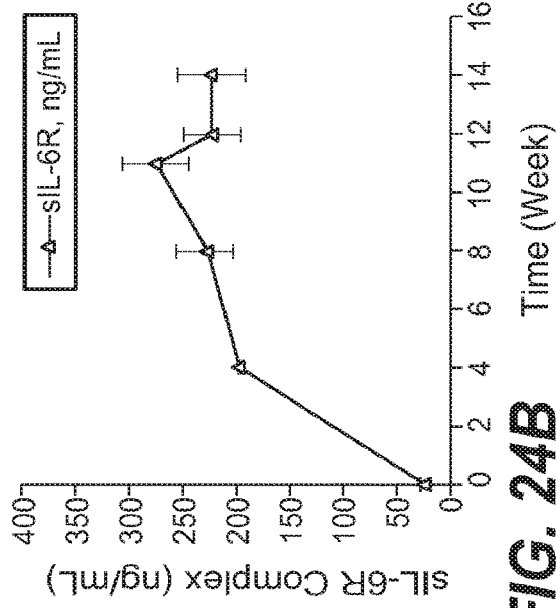
Figure 24B:
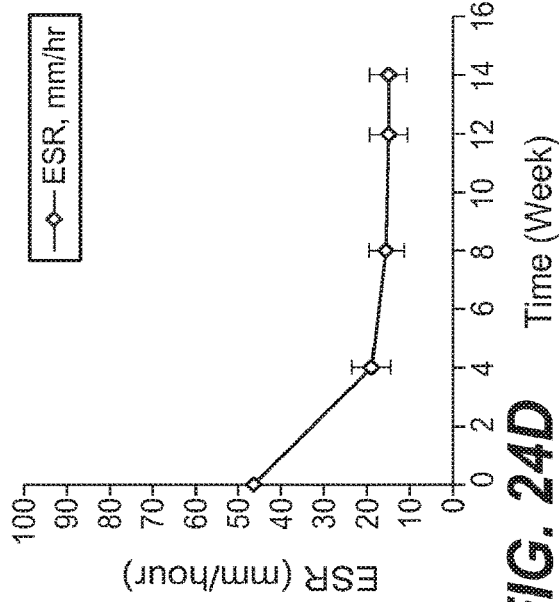
Figure 24C:
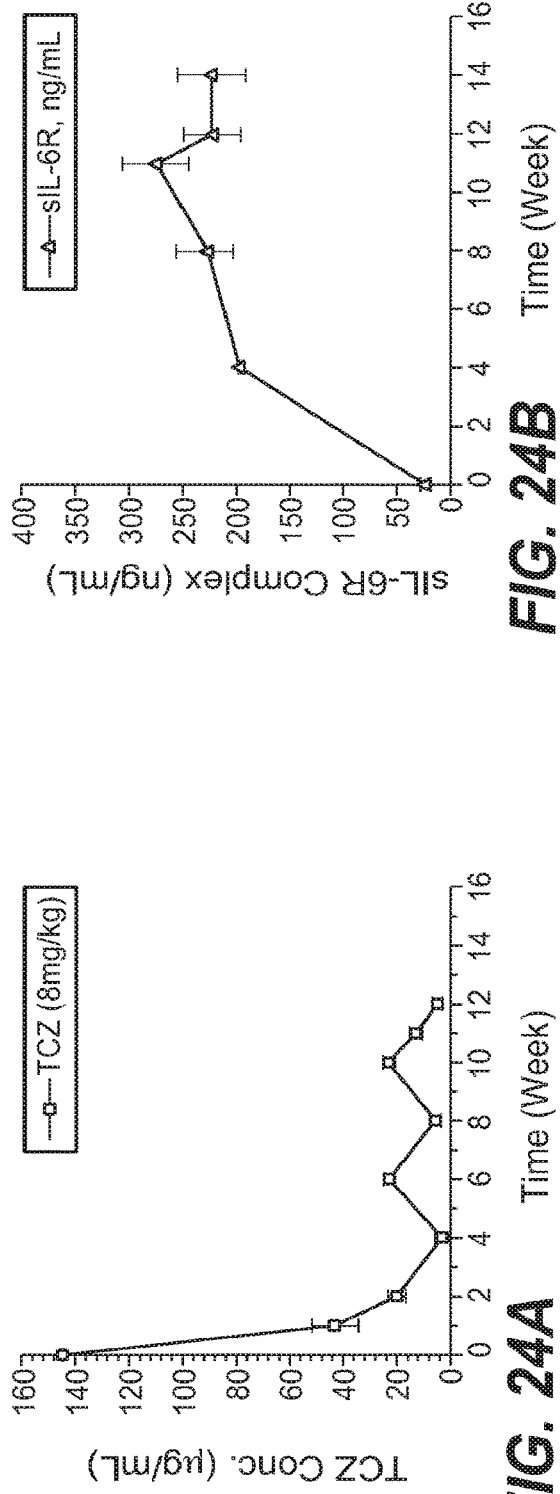
Figure 24D:
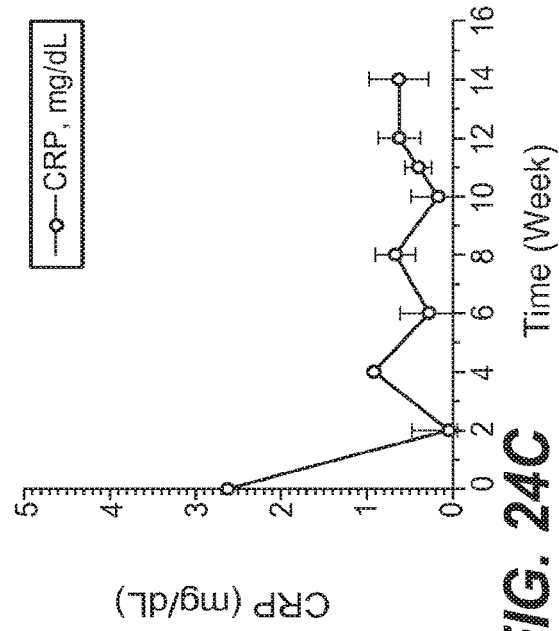

FIGS. 24A-D show the PK, sIL-6R, CRP and ESR profiles over time during 12 weeks of treatment. sIL-6R levels increased over time and reached stable condition at week 12 (FIG. 24B). CRP levels fluctuated during a dosing interval with elevation prior to next dose (FIG. 24C). ESR decreased by week 4 and stay low after week 8 (FIG. 24D). Analysis of PK-PD relationship indicated that when the serum TCZ concentration was at or above (1 μg/mL), CRP and ESR were low and sIL-6R saturation was high.

Following administration of TCZ 8 mg/kg IV Q4W to pcJIA patients in study MRA318JP, prior to the next infusion at weeks 4, 8 and 12, approximately 35 to 39% of patients had TCZ $C_{min}$<1 μg/mL (Table 10). Although most children in MRA318JP reached the ACR30 endpoint at Week 12, children with non-measurable TCZ levels at $C_{min}$ were much less likely to achieve JIA ACR 70 than those with measurable $C_{min}$ TCZ levels (25% vs 73%). The majority of children with non-measurable TCZ at $C_{min}$, and not achieving the best efficacy responses had lower body weights (<30 kg).

TABLE 10

Mean ± SD Serum TCZ Concentrations and % of Patients in Serum TCZ Concentration Less than 1 μg/mL

| Time of Visit | Mean ± SD TCZ, μg/mL | % of patients with TCZ <1 μg/mL |
|---|---|---|
| 0 (pre dose) | 0 | NA |
| 0 (post dose) | 145 ± 37.5 | 0 |
| 1 | 42.9 ± 13.3 | 0 |
| 2 | 20.2 ± 8.75 | 0 |
| 4 | 3.83 ± 3.47 | 38.9 |
| 6 | 22.6 ± 8.59 | 5.6 |
| 8 | 5.71 ± 5.71 | 35.3 |
| 10 | 22.8 ± 9.23 | 5.9 |
| 11 | 12.7 ± 7.01 | 17.6 |
| 12 | 4.88 ± 4.68 | 38.9 |

The population PK analysis was developed based data from MRA318JP and interim PK data from WA19977 (117 patients). In study NP22623, 162 mg TCZ was administered in the adult RA patients as QW or Q2W dosing for 12 weeks in a total of 29 patients. Empirical modeling of the PK data from NP22623 provided subcutaneous absorption PK parameters (absorption rate constant Ka and bioavailability F) in RA patients. Under the assumption that these absorption PK parameters are similar to the absorption PK parameters in pediatric pcJIA patients, and disposition PK parameters from WA19977 study are independent of the route of administration, the PK exposures were simulated for pcJIA patients <30 kg and ≥30 kg following multiple dose administration up to a steady state. The simulated PK profiles for IV and SC administration are illustrated in FIGS. 21A and 21B, respectively. TCZ concentrations following IV and SC administration during a dosing interval of 4 weeks at steady state appear to be approximately at similar levels. The model simulated TCZ exposure parameters ($AUC_{4week}$, $C_{min}$ and $C_{max}$) are shown in Table 11. SC dose of 162 mg Q2W for both BW<30 kg and BW≥30 kg patients appear to be appropriate to produce comparable $AUC_{4week}$ to the WA19977 study (Table 11). Therefore, the proposed SC dose for Group 1 is 162 mg Q2W for all patients.

TABLE 11

Model Simulated Serum TCZ PK Exposure Parameters for SC and IV Dosing Regimens for Patients in WA19977 Study

| WA19977 | BW, kg | N | $AUC_{4\ week}$, μg · d/mL | $C_{max}$, μg/mL | $C_{min}$, μg/mL |
|---|---|---|---|---|---|
| 8 mg/kg Q4W[a] | <30 | 20 | 424 ± 143 (205-754) | 113 ± 24 (74-164) | 0.3 ± 0.6 (0-2.6) |
| 10 mg/kg Q4W[a] | <30 | 19 | 825 ± 226 (328-1359) | 185 ± 36 (132-249) | 2.4 ± 2.5 (0-9.2) |
| 8 mg/kg Q4W[a] | ≥30 | 78 | 1031 ± 359 (485-2058) | 171 ± 38 (79-265) | 5.3 ± 6.4 (0.1-29) |
| 162 mg Q2W[b] | <30 | 39 | 945 ± 377 (299-2111) | 43 ± 14 (19-87) | 20 ± 12 (1.8-57) |
| 162 mg Q2W[b] | ≥30 | 78 | 604 ± 178 (148-985) | 28 ± 7 (11-42) | 12 ± 5 (0.6-28) |

Mean ± SD (min-max) presented
[a]Summary of PK parameters estimated by population analysis of data from study WA19977 follwing IV dosing; $AUC_{2\ week}$ was multiplied by 2 in order to compare with other SC regimens.
[b]Summary of simulated PK parameters for individual patients from Study WA19977 following SC dosing.

Thus, 162 mg of TCZ is administered subcutaneously every 2 weeks (Q2W) to patients with pcJIA (N=24). The treatment period will last for 14 weeks. During the treatment period, stable NSAIDs and MTX will be continued unchanged throughout 14 weeks of the study. No tapering of corticosteroids, NSAIDs or methotrexate can occur during the study except for safety reasons. PK, PD, efficacy parameters will be assessed at the scheduled time points. The follow-up visit will be performed at 4 and 8 weeks after last SC dosing.

It is anticipated that the anti-IL-6R antibody (TCZ) will be effective in pcJIA patients when administered as 162 mg dose every 2 weeks (Q2W) by SQ administration, e.g., for up to 14 weeks.

Example 8

SQ Administered Anti-IL-6R Antibody for Systemic Sclerosis

This is a Phase 2/3, multicenter, randomized, double-blind, placebo-controlled, two-arm, parallel-group trial in patients with systemic sclerosis (SSc). A TCZ formulation with 180 mg/mL TCZ and no hyaluronidase (see Table 2 in Example 4) is subcutaneously administered to SSC patients in this study. The primary endpoint, the change in modified Rodnan skin score (mRSS) from baseline at Week 24, will be evaluated at Week 24. There will be a 48-week blinded period followed by a 48-week open-label period.

Patients will be randomized in a 1:1 ratio to receive either 162 mg of SC TCZ weekly (QW) (Group A) or SC placebo QW (Group B) for 48 weeks. The primary analysis will occur when all patients have reached Week 24.

Starting at Week 48, all patients will receive open-label treatment with 162 mg of TCZ subcutaneously QW and no patient will receive a placebo injection.

Efficacy parameters will be assessed, starting at baseline to Week 96, as described in the schedule of assessments.

Target Population

Patients must meet the following criteria for study entry:
    Ability and willingness to give written informed consent and comply with the requirements of the study protocol
    Diagnosis of SSc, as defined using the American College of Rheumatology criteria (1980)
    Disease duration of ≤60 months (defined as time from the first non-Raynaud phenomenon manifestation)

Age ≥18 years at baseline
≥15 and ≤40 mRSS units at the screening visit
Uninvolved skin at one of the following locations:
  Front of the middle region of the thighs
  Lower part of the abdomen below the navel except for the 2-inch area directly around the navel
  Outer area of the upper arms (if a caregiver is giving the patient injections)
Active disease defined as at least one A criterion and one B criterion each:
  Criteria A at screening
    Increase ≥3 in mRSS units at screening compared with the last visit within previous 1-6 months
    Involvement of one new body area with ≥2 mRSS units at screening compared with the last visit within the previous 1-6 months
    Involvement of two new body areas with ≥1 mRSS units at screening compared with the last visit within the previous 1-6 months
    Other documentation of worsening skin thickening at screening compared with the last visit within the previous 1-6 months consistent with the progression of skin thickening described in the above criteria using mRSS
    Presence of 1 or more TFRs at screening
  Criteria B at screening
    High-sensitivity C-reactive protein ≥1 mg/dL
    Erythrocyte sedimentation rate ≥28 mm/hr
    Platelet count (≥330×10³/μL)
Treatment with oral corticosteroids (≤10 mg/day of prednisone or equivalent) is permitted if the patient is on a stable dose regimen for ≥2 weeks prior to and including at baseline.
Treatment with non-steroidal anti-inflammatory drugs (NSAIDs) is permitted if the patient is on a stable dose regimen for ≥2 weeks prior to and including at baseline.
Angiotensin-converting enzyme inhibitors, calcium-channel blockers, protein-pump inhibitors, and/or oral vasodilators are permitted if the patient is on a stable dose for ≥4 weeks prior to and including at baseline.
If female of childbearing potential, the patient must have a negative pregnancy test at screening and the baseline visit.

Efficacy Outcome Measures

The primary efficacy endpoint is the change in modified Rodnan skin score (mRSS) from baseline at Week 24. Skin thickness will be assessed by palpation and rated using a score from 0 (normal) to 3 (severe skin thickening) across 17 different sites. The total score is the sum of the individual skin scores in the 17 body areas (e.g., face, hands, fingers; proximal area of the arms, distal area of the arms, thorax, abdomen; proximal area of the legs, and distal area of the legs, feet), giving a range of 0-51 units. The instrument has been validated for patients with SSc.

The secondary efficacy endpoints for this study are as follows:
  Change in Scleroderma Health Assessment Questionnaire-Disability Index (SHAQ-DI) score from baseline at Weeks 24 and 48
  Change in 28 tender joint count (TJC) from baseline at Weeks 24 and 48 in patients with joint involvement at baseline
  Change in the patient's global assessment from baseline at Weeks 24 and 48
  Change in the clinician's global assessment from baseline at Weeks 24 and 48
  Change in Functional Assessment of Chronic Illness Therapy—Fatigue (FACIT)-Fatigue score from baseline at Weeks 24 and 48
  Change in Pruritus 5-D Itch Scale from baseline at Weeks 24 and 48
  Change in mRSS from baseline at Week 48
  Proportion of patients with change from baseline in the mRSS at Week 48 greater than or equal to the change from baseline in the mRSS at Week 24

It is anticipated that subcutaneously administered TCZ as disclosed herein will improve cutaneous sclerosis, improve physical function, and/or slow progression of organ damage in SSc patients treated as disclosed, relative to placebo-treated patients. For example, the TCZ shall achieve the primary efficacy endpoint (change in mRSS at week 24) and/or any one or more of the secondary endpoints.

Example 9

SQ Administered Anti-IL-6R Antibody for Giant Cell Arteritis

This example describes the use of subcutaneously administered anti-IL-6R antibody (TCZ) to treat giant cell arteritis (GCA). The TCZ formulation with 180 mg/mL TCZ and no hyaluronidase described in Table 2 in Example 4 is used to treat patients with GCA (new onset or refractory GCA).

The protocol for treating patients with GCA is shown in FIG. 22. The proposed study is multicentre, randomized, double-blind, placebo-controlled in patients diagnosed with GCA. Patients may be either new onset or refractory (i.e. GCA patients who have responded inadequately to previous therapy with corticosteroids (CS)). The primary endpoint will be CS free sustained remission at 9 months. Remission is defined as absence of signs and symptoms and normalization of acute phase response. Sustained is defined as absence of flare following induction of remission. Patients achieving the primary endpoint at 9 months will have achieved remission within 3 months and maintained their remission for at least 6 months whilst being able to taper off their CS. Secondary endpoints at 9 months include time to GCA disease flare after clinical remission, cumulative CS dose, quality of life and change in acute phase reactant and hemoglobin.

Two doses of subcutaneously administered TCZ will be used:
  162 mg every week (qw); and
  162 mg every other week (q2w).

Patients will be randomized in a 2:1:1 ratio (100:50:50) to receive either 162 mg of SC TCZ qw, 162 mg of SC TCZ q2w or SC placebo for 9 months in a double blind fashion. In addition, all patients will receive background CS therapy and follow a CS tapering regimen over a 6 month period (see Table 12). Refractory subjects will enter the study at 10 mg higher than the dose that previously controlled the disease and continue the trial glucocorticoid taper outlined from the prednisone dose at entry. In the absence of relapse, this schedule will result in a glucocorticoid dosage below 5 mg after 4 months and no glucocorticoid use after 6 months.

TABLE 12

Prednisone Schedule: New Onset Patients

| Week | Daily prednisone dose, both arms (mg/day) |
| --- | --- |
| 1 | 60 |
| 2 | 60 |

TABLE 12-continued

Prednisone Schedule: New Onset Patients

| Week | Daily prednisone dose, both arms (mg/day) |
|---|---|
| 3 | 50 |
| 4 | 40 |
| 5 | 30 |
| 6 | 25 |
| 7 | 20 |
| 8 | 17.5 |
| 9 | 15 |
| 10 | 12.5 |
| 11 | 10 |
| 12 | 9 |
| 13 | 8 |
| 14 | 7 |
| 15 | 6 |
| 16 | 5 |
| 17 | 4 |
| 18 | 4 |
| 19 | 3 |
| 20 | 3 |
| 21 | 2 |
| 22 | 2 |
| 23 | 1 |
| 24 | 1 |

At month 9, all patients may enter part 2 (open label extension) of the study. Patients who meet the primary endpoint will be required to stop their subcutaneous injections and be followed for maintenance of response. Patients who do not meet the primary endpoint, will have the option to escape to investigator-led therapy that can include open label TCZ. The purpose of the open label extension is to describe the long term safety and efficacy of a course of TCZ in GCA, to describe long term steroid sparing effect of TCZ and its sequelae in terms of CS related adverse events, and to describe a potential requirement for maintenance of TCZ therapy beyond 9 months.

The target population for this study is adult patients with GCA. New onset and relapsed/refractory GCA patients will be eligible.

Diagnosis of GCA is according to the following criteria
Westergreen erythrocyte sedimentation rate (ESR)>40 mm/hour
Unequivocal cranial symptoms of GCA (new onset localized headache, scalp or temporal artery tenderness, ischemia-related vision loss, or otherwise unexplained mouth or jaw pain upon mastication)
At least one of the following:
  Temporal artery biopsy revealing features of GCA
  Symptoms of polymyalgia rheumatica (PMR), defined as shoulder and/or hip girdle pain associated with inflammatory morning stiffness
  Evidence of large-vessel vasculitis by angiography or cross-sectional imaging study such us magnetic resonance angiography (MRA), computed tomography angiography (CTA), or positron emission tomography-computed tomography angiography (PET-CTA)
New Onset or refractory GCA is classified according to the following criteria
New onset: active GCA diagnosis (clinical signs or symptoms and ESR≥40 mm/hr) made within 4 weeks of baseline visit (irrespective of whether CS initiated or active disease activity at baseline visit)
Refractory: diagnosis made ≥4 weeks prior to baseline visit and active GCA (clinical signs and symptoms and ESR≥40 mm/hr) within 4 weeks baseline irrespective of CS treatment It is anticipated that subcutaneously administered TCZ as disclosed herein will effectively treat GCA, for example by reducing GCA signs and symptoms, maintaining clinical remission, and/or reducing or stopping corticosteroid use in the patient with GCA.

What is claimed is:

1. An article of manufacture comprising a subcutaneous administration device, which contains and delivers to a patient a 162 mg fixed dose of tocilizumab.

2. The article of manufacture of claim 1, wherein the subcutaneous administration device is selected from the group consisting of a syringe, an injection device, an infusion pump, an injector pen, a needleless device, an autoinjector, and a subcutaneous patch delivery system.

3. The article of manufacture of claim 2, wherein the subcutaneous administration device is a syringe, including a pre-filled syringe.

4. The article of manufacture of claim 2, wherein the subcutaneous administration device is an autoinjector.

5. An article of manufacture comprising a subcutaneous administration device, which contains and delivers to a patient a 162 mg fixed dose of an anti-IL-6R antibody, wherein the anti-IL-6R antibody comprises the light chain and heavy chain amino acid sequences of SEQ ID NOs:1 and 2, respectively.

6. The article of manufacture of claim 5, wherein the subcutaneous administration device is selected from the group consisting of a syringe, an injection device, an infusion pump, an injector pen, a needleless device, an autoinjector, and a subcutaneous patch delivery system.

7. The article of manufacture of claim 6, wherein the subcutaneous administration device is a syringe, including a pre-filled syringe.

8. The article of manufacture of claim 6, wherein the subcutaneous administration device is an autoinjector.

* * * * *

(12) INTER PARTES REVIEW CERTIFICATE (3504th)
United States Patent
Zhang et al.

(10) Number: US 10,874,677 K1
(45) Certificate Issued: Mar. 19, 2024

(54) SUBCUTANEOUSLY ADMINISTERED ANTI-IL-6 RECEPTOR ANTIBODY

(71) Applicants: Hoffmann-La Roche Inc.; CHUGAI SEIYAKU KABUSHIKI KAISHA

(72) Inventors: Xiaoping Zhang; Kimio Terao

(73) Assignees: Hoffmann-La Roche Inc.; CHUGAI SEIYAKU KABUSHIKI KAISHA

Trial Number:
IPR2022-00579 filed Feb. 21, 2022

Inter Partes Review Certificate for:
Patent No.: 10,874,677
Issued: Dec. 29, 2020
Appl. No.: 16/254,105
Filed: Jan. 22, 2019

The results of IPR2022-00579 are reflected in this inter partes review certificate under 35 U.S.C. 318(b).

INTER PARTES REVIEW CERTIFICATE
U.S. Patent 10,874,677 K1
Trial No. IPR2022-00579
Certificate Issued Mar. 19, 2024

AS A RESULT OF THE INTER PARTES REVIEW PROCEEDING, IT HAS BEEN DETERMINED THAT:

Claims 1-8 are cancelled.

\* \* \* \* \*